(12) United States Patent
Servidio et al.

(10) Patent No.: US 12,262,899 B2
(45) Date of Patent: Apr. 1, 2025

(54) SYSTEMS AND METHODS FOR PREPARING BONE VOIDS TO RECEIVE A PROSTHESIS

(71) Applicant: Howmedica Osteonics Corp., Mahwah, NJ (US)

(72) Inventors: Damon J. Servidio, Towaco, NJ (US); Carlos E. Collazo, Old Greenwich, CT (US); Sujit Sivadas, Bridgewater, NJ (US)

(73) Assignee: Howmedica Osteonics Corp., Mahwah, NJ (US)

( * ) Notice: Subject to any disclaimer, the term of this patent is extended or adjusted under 35 U.S.C. 154(b) by 0 days.

(21) Appl. No.: 18/535,031

(22) Filed: Dec. 11, 2023

(65) Prior Publication Data
US 2024/0099730 A1 Mar. 28, 2024

Related U.S. Application Data

(63) Continuation of application No. 17/496,996, filed on Oct. 8, 2021, now Pat. No. 11,877,757, which is a continuation of application No. 16/274,684, filed on Feb. 13, 2019, now Pat. No. 11,172,940, which is a continuation of application No. 15/597,851, filed on
(Continued)

(51) Int. Cl.
A61B 17/16 (2006.01)
A61B 17/17 (2006.01)
A61F 2/38 (2006.01)
A61F 2/30 (2006.01)

(52) U.S. Cl.
CPC ........ A61B 17/1662 (2013.01); A61B 17/164 (2013.01); A61B 17/1668 (2013.01); A61B 17/1675 (2013.01); A61B 17/1717 (2013.01); A61B 17/1739 (2013.01); A61B 17/175 (2013.01); A61B 17/1764 (2013.01); A61F 2/38 (2013.01); A61F 2/3859 (2013.01); A61F 2/389 (2013.01); A61B 17/1615 (2013.01); (Continued)

(58) Field of Classification Search
CPC .............. A61B 17/1615; A61B 17/164; A61B 17/1662; A61B 17/1668; A61B 17/1675
See application file for complete search history.

(56) References Cited

U.S. PATENT DOCUMENTS 3,859,669 A 1/1975 Shersher et al.
3,924,274 A 12/1975 Heimke et al.
(Continued)

FOREIGN PATENT DOCUMENTS

DE 7634751 U1 5/1977
DE 2842847 A1 4/1980
(Continued)

OTHER PUBLICATIONS

Extended European Search Report including Search Opinion from 24172684.3, dated Jul. 10, 2024, pp. 1-7.
(Continued)

Primary Examiner — Samuel S Hanna
(74) Attorney, Agent, or Firm — Lerner David LLP

(57) ABSTRACT

A method of implant a knee prosthesis includes forming a bone void at an end of a bone, implanting a void filler in the bone void, and implanting a knee prosthesis onto the end of the bone so that a stem of the knee prosthesis is received by the void filler.

17 Claims, 52 Drawing Sheets

Related U.S. Application Data

May 17, 2017, now Pat. No. 10,265,083, which is a continuation of application No. 14/837,437, filed on Aug. 27, 2015, now Pat. No. 10,213,215, which is a continuation of application No. 13/730,082, filed on Dec. 28, 2012, now Pat. No. 9,149,282.

(60) Provisional application No. 61/581,736, filed on Dec. 30, 2011.

(52) U.S. Cl.
CPC ............ *A61F 2002/30604* (2013.01); *A61F 2002/30736* (2013.01); *A61F 2002/30884* (2013.01)

(56) References Cited

U.S. PATENT DOCUMENTS

| | | |
|---|---|---|
| 3,979,778 A | 9/1976 | Stroot |
| 3,986,212 A | 10/1976 | Sauer |
| 4,045,825 A | 9/1977 | Stroot |
| 4,045,826 A | 9/1977 | Stroot |
| 4,065,817 A | 1/1978 | Branemark et al. |
| 4,158,893 A | 6/1979 | Swanson |
| 4,301,553 A | 11/1981 | Noiles |
| 4,306,550 A | 12/1981 | Forte |
| 4,341,206 A | 7/1982 | Perrett et al. |
| 4,355,427 A | 10/1982 | Schneider |
| 4,463,444 A | 7/1984 | Daniels et al. |
| 4,549,319 A | 10/1985 | Meyer |
| 4,681,589 A | 7/1987 | Tronzo |
| 4,693,721 A | 9/1987 | Ducheyne |
| 4,714,471 A | 12/1987 | Grundei |
| 4,714,475 A | 12/1987 | Grundei et al. |
| 4,728,335 A | 3/1988 | Jurgutis |
| 4,735,625 A | 4/1988 | Davidson |
| 4,738,256 A | 4/1988 | Freeman et al. |
| 4,751,922 A | 6/1988 | DiPietropolo |
| 4,777,942 A | 10/1988 | Frey et al. |
| 4,790,852 A | 12/1988 | Noiles |
| 4,822,366 A | 4/1989 | Bolesky |
| 4,846,839 A | 7/1989 | Noiles |
| 4,944,757 A | 7/1990 | Martinez et al. |
| 4,950,298 A | 8/1990 | Gustilo et al. |
| 4,997,448 A | 3/1991 | Filer |
| 5,006,121 A | 4/1991 | Hafeli |
| 5,011,496 A | 4/1991 | Forte et al. |
| 5,035,717 A | 7/1991 | Brooks |
| 5,047,033 A | 9/1991 | Fallin |
| 5,049,157 A | 9/1991 | Mittelmeier et al. |
| 5,061,271 A | 10/1991 | Van Zile |
| 5,061,287 A | 10/1991 | Feiler |
| 5,080,685 A | 1/1992 | Bolesky et al. |
| 5,089,004 A | 2/1992 | Averill et al. |
| 5,108,398 A | 4/1992 | McQueen et al. |
| 5,122,134 A | 6/1992 | Borzone et al. |
| 5,152,797 A | 10/1992 | Luckman et al. |
| 5,169,402 A | 12/1992 | Elloy |
| 5,190,548 A | 3/1993 | Davis |
| 5,192,283 A | 3/1993 | Ling et al. |
| 5,342,363 A | 8/1994 | Richelsoph |
| 5,342,366 A | 8/1994 | Whiteside et al. |
| 5,358,526 A | 10/1994 | Tornier |
| 5,387,218 A | 2/1995 | Meswania |
| 5,403,320 A | 4/1995 | Luman et al. |
| 5,411,505 A | 5/1995 | Mumme |
| 5,441,501 A | 8/1995 | Kenyon |
| 5,445,642 A | 8/1995 | McNulty et al. |
| 5,480,453 A | 1/1996 | Burke |
| 5,489,311 A | 2/1996 | Cipolletti |
| 5,496,324 A | 3/1996 | Barnes |
| 5,507,832 A | 4/1996 | Michielli et al. |
| 5,527,316 A | 6/1996 | Stone et al. |
| 5,534,005 A | 7/1996 | Tokish, Jr. et al. |
| 5,540,694 A | 7/1996 | DeCarlo, Jr. et al. |
| 5,591,233 A | 1/1997 | Kelman et al. |
| 5,609,641 A | 3/1997 | Johnson et al. |
| 5,634,927 A | 6/1997 | Houston et al. |
| 5,649,299 A | 7/1997 | Battin et al. |
| 5,674,223 A * | 10/1997 | Cipolletti ........... A61B 17/1675 606/88 |
| 5,702,486 A | 12/1997 | Craig et al. |
| 5,741,335 A | 4/1998 | Gerber et al. |
| 5,755,720 A | 5/1998 | Mikhail |
| 5,755,793 A | 5/1998 | Smith et al. |
| 5,766,261 A | 6/1998 | Neal et al. |
| 5,782,921 A | 7/1998 | Colleran et al. |
| 5,824,097 A | 10/1998 | Gabriel et al. |
| 5,906,644 A | 5/1999 | Powell |
| 5,931,841 A | 8/1999 | Ralph |
| 5,944,758 A | 8/1999 | Mansat et al. |
| 5,951,603 A | 9/1999 | O'Neil et al. |
| 5,957,925 A | 9/1999 | Cook et al. |
| 5,976,145 A | 11/1999 | Kennefick, III |
| 5,976,147 A | 11/1999 | LaSalle et al. |
| 5,984,968 A | 11/1999 | Park |
| 5,989,257 A | 11/1999 | Tidwell et al. |
| 5,989,261 A | 11/1999 | Walker et al. |
| 5,993,455 A | 11/1999 | Noble |
| 6,010,534 A | 1/2000 | O'Neil et al. |
| 6,045,556 A | 4/2000 | Cohen |
| 6,053,945 A | 4/2000 | O'Neil et al. |
| 6,071,311 A | 6/2000 | O'Neil et al. |
| 6,127,596 A | 10/2000 | Brown et al. |
| 6,139,584 A | 10/2000 | Ochoa et al. |
| 6,152,963 A | 11/2000 | Noiles et al. |
| 6,171,342 B1 | 1/2001 | O'Neil et al. |
| 6,197,065 B1 | 3/2001 | Martin et al. |
| 6,214,052 B1 | 4/2001 | Burkinshaw |
| 6,214,053 B1 | 4/2001 | Ling et al. |
| 6,228,120 B1 | 5/2001 | Leonard et al. |
| 6,241,722 B1 | 6/2001 | Dobak et al. |
| 6,245,113 B1 | 6/2001 | Revie et al. |
| 6,264,699 B1 | 7/2001 | Noiles et al. |
| 6,283,999 B1 | 9/2001 | Rockwood, Jr. |
| 6,398,812 B1 | 6/2002 | Masini |
| 6,406,496 B1 | 6/2002 | Ruter |
| 6,440,171 B1 | 8/2002 | Doubler et al. |
| 6,494,913 B1 | 12/2002 | Huebner |
| 6,508,841 B2 | 1/2003 | Martin et al. |
| 6,520,994 B2 | 2/2003 | Nogarin |
| 6,558,425 B2 | 5/2003 | Rockwood, Jr. |
| 6,592,622 B1 | 7/2003 | Ferguson |
| 6,702,822 B1 | 3/2004 | Noiles et al. |
| 6,712,855 B2 | 3/2004 | Martin et al. |
| 6,887,276 B2 | 5/2005 | Gerbec et al. |
| 6,902,583 B2 | 6/2005 | Gerbec et al. |
| 6,905,513 B1 | 6/2005 | Metzger |
| 6,945,556 B2 | 9/2005 | Maertens |
| 7,001,429 B2 | 2/2006 | Ferguson |
| 7,070,622 B1 | 7/2006 | Brown et al. |
| 7,074,224 B2 | 7/2006 | Daniels et al. |
| 7,090,677 B2 | 8/2006 | Fallin et al. |
| 7,108,719 B2 | 9/2006 | Horber |
| 7,112,203 B2 | 9/2006 | Le Beguec et al. |
| 7,141,073 B2 | 11/2006 | May et al. |
| 7,175,664 B1 | 2/2007 | Lakin |
| 7,255,702 B2 | 8/2007 | Serra et al. |
| 7,291,174 B2 | 11/2007 | German et al. |
| 7,297,163 B2 | 11/2007 | Huebner |
| 7,338,528 B2 | 3/2008 | Stone et al. |
| 7,393,355 B2 | 7/2008 | Tulkis et al. |
| 7,462,197 B2 | 12/2008 | Tornier et al. |
| 7,476,254 B2 | 1/2009 | White et al. |
| 7,481,814 B1 | 1/2009 | Metzger |
| 7,481,841 B2 | 1/2009 | Hazebrouck et al. |
| 7,507,256 B2 | 3/2009 | Heck et al. |
| 7,537,664 B2 | 5/2009 | O'Neill et al. |
| 7,556,652 B2 | 7/2009 | Angibaud et al. |
| 7,615,080 B2 | 11/2009 | Ondrla |
| 7,632,273 B2 | 12/2009 | Schnieders et al. |
| 7,670,383 B1 | 3/2010 | Brown et al. |
| 7,722,678 B2 | 5/2010 | Brown et al. |
| 7,785,328 B2 | 8/2010 | Christie et al. |

(56) References Cited

U.S. PATENT DOCUMENTS

| | | |
|---|---|---|
| 7,799,085 B2 | 9/2010 | Goodfried et al. |
| 7,806,936 B2 | 10/2010 | Wright |
| 7,832,405 B1 | 11/2010 | Schlueter et al. |
| 7,833,228 B1 | 11/2010 | Hershberger |
| 7,892,288 B2 | 2/2011 | Blaylock et al. |
| 7,892,290 B2 | 2/2011 | Bergin et al. |
| 7,918,892 B2 | 4/2011 | Huebner |
| 7,942,879 B2 | 5/2011 | Christie et al. |
| 7,976,545 B2 | 7/2011 | Hershberger et al. |
| 7,998,217 B1 | 8/2011 | Brown |
| 8,029,573 B2 | 10/2011 | Podolsky |
| 8,048,166 B2 | 11/2011 | Brown et al. |
| 8,052,687 B2 | 11/2011 | Sackett et al. |
| 8,105,385 B2 | 1/2012 | Maroney et al. |
| 8,118,868 B2 | 2/2012 | May et al. |
| 8,147,498 B2 | 4/2012 | Schlueter et al. |
| 8,147,861 B2 | 4/2012 | Jones et al. |
| 8,157,869 B2 | 4/2012 | Metzger et al. |
| 8,167,882 B2 | 5/2012 | Sackett et al. |
| 8,177,788 B2 | 5/2012 | McLean et al. |
| 8,177,849 B2 | 5/2012 | Meyers et al. |
| 8,182,542 B2 | 5/2012 | Ferko |
| 8,187,336 B2 | 5/2012 | Jamali |
| 8,192,497 B2 | 6/2012 | Ondrla |
| 8,226,725 B2 | 7/2012 | Ferko |
| 8,273,091 B2 | 9/2012 | Elghazaly |
| 8,337,498 B2 | 12/2012 | Rasmussen |
| 8,350,186 B2 | 1/2013 | Jones et al. |
| 8,372,157 B2 | 2/2013 | Petersen et al. |
| 8,382,849 B2 | 2/2013 | Thomas |
| 8,424,183 B2 | 4/2013 | Thomas |
| 8,444,699 B2 | 5/2013 | Metzger et al. |
| 8,460,393 B2 | 6/2013 | Smith et al. |
| 8,506,645 B2 | 8/2013 | Blaylock et al. |
| 8,535,385 B2 | 9/2013 | Hanssen et al. |
| 8,585,770 B2 | 11/2013 | Meridew et al. |
| 8,636,800 B2 | 1/2014 | Ferko et al. |
| 8,696,757 B2 | 4/2014 | Brown et al. |
| 8,715,356 B2 | 5/2014 | Porter et al. |
| 8,728,387 B2 | 5/2014 | Jones et al. |
| 8,790,402 B2 | 7/2014 | Monaghan et al. |
| 8,828,014 B2 | 9/2014 | Gross |
| 8,900,317 B2 | 12/2014 | Zubok et al. |
| 9,011,444 B2 | 4/2015 | Primiano et al. |
| 9,149,282 B2 | 10/2015 | Servidio et al. |
| 9,204,884 B2 | 12/2015 | Dees et al. |
| 9,259,257 B2 | 2/2016 | Bagga et al. |
| 9,320,527 B2 | 4/2016 | Kehres et al. |
| 9,345,523 B2 | 5/2016 | Segina et al. |
| 9,498,343 B2 | 11/2016 | Nevins |
| 9,526,513 B2 | 12/2016 | Collazo et al. |
| 9,668,758 B2 | 6/2017 | Collazo et al. |
| 9,795,392 B2 | 10/2017 | Zajac |
| RE47,149 E | 12/2018 | Primiano et al. |
| 10,149,763 B2 | 12/2018 | Krebs et al. |
| 10,265,083 B2 | 4/2019 | Servidio et al. |
| 10,299,929 B2 | 5/2019 | Collazo |
| 10,335,171 B2 | 7/2019 | Collazo et al. |
| 10,524,806 B2 | 1/2020 | Collazo et al. |
| RE48,163 E | 8/2020 | Primiano et al. |
| 11,172,941 B2 | 11/2021 | Collazo et al. |
| 11,173,034 B2 | 11/2021 | Collazo |
| 2001/0009974 A1 | 7/2001 | Reisfeld |
| 2002/0016634 A1 | 2/2002 | Maroney et al. |
| 2003/0139818 A1 | 7/2003 | Rogers et al. |
| 2003/0171756 A1 | 9/2003 | Fallin et al. |
| 2003/0171815 A1 | 9/2003 | Kana et al. |
| 2003/0187449 A1 | 10/2003 | McCleary et al. |
| 2004/0049285 A1 | 3/2004 | Haas |
| 2004/0092951 A1 | 5/2004 | Serra et al. |
| 2004/0162619 A1 | 8/2004 | Blaylock et al. |
| 2004/0267267 A1 | 12/2004 | Daniels et al. |
| 2005/0090902 A1 | 4/2005 | Masini |
| 2005/0177241 A1 | 8/2005 | Angibaud et al. |
| 2005/0288676 A1 | 12/2005 | Schnieders et al. |
| 2006/0041317 A1 | 2/2006 | Hazebrouck et al. |
| 2006/0147332 A1 | 7/2006 | Jones et al. |
| 2006/0200249 A1 | 9/2006 | Beguin et al. |
| 2006/0241776 A1 | 10/2006 | Brown et al. |
| 2007/0088443 A1 | 4/2007 | Hanssen et al. |
| 2007/0118229 A1 | 5/2007 | Bergin et al. |
| 2007/0142914 A1 | 6/2007 | Jones et al. |
| 2007/0162033 A1 | 7/2007 | Daniels et al. |
| 2007/0225821 A1 | 9/2007 | Reubelt et al. |
| 2008/0051908 A1 | 2/2008 | Angibaud et al. |
| 2008/0147071 A1 | 6/2008 | Serra et al. |
| 2008/0161812 A1 | 7/2008 | Sackett et al. |
| 2008/0281428 A1 | 11/2008 | Meyers et al. |
| 2008/0306600 A1 | 12/2008 | Huebner |
| 2008/0306603 A1 | 12/2008 | Reich et al. |
| 2009/0088862 A1 | 4/2009 | Thomas et al. |
| 2009/0157190 A1 | 6/2009 | Collazo et al. |
| 2010/0057212 A1 | 3/2010 | Thomas |
| 2010/0076565 A1 | 3/2010 | Thomas |
| 2010/0082031 A1 | 4/2010 | Sackett et al. |
| 2010/0114323 A1 | 5/2010 | Deruntz et al. |
| 2010/0222891 A1 | 9/2010 | Goodfried et al. |
| 2010/0262146 A1 | 10/2010 | Tulkis |
| 2010/0286696 A1 | 11/2010 | Christie et al. |
| 2011/0009973 A1 | 1/2011 | Meyers et al. |
| 2011/0009974 A1 | 1/2011 | Blaylock et al. |
| 2011/0015634 A1 | 1/2011 | Smith et al. |
| 2011/0130840 A1 | 6/2011 | Oskouei |
| 2011/0190899 A1 | 8/2011 | Pierce et al. |
| 2011/0213467 A1 | 9/2011 | Lozier et al. |
| 2011/0218636 A1 | 9/2011 | Smith et al. |
| 2012/0016482 A1 | 1/2012 | Mooradian et al. |
| 2012/0035733 A1 | 2/2012 | Porter et al. |
| 2012/0089146 A1 | 4/2012 | Ferko et al. |
| 2012/0209270 A1 | 8/2012 | Segina et al. |
| 2012/0226281 A1 | 9/2012 | Sackett et al. |
| 2012/0310361 A1 | 12/2012 | Zubok et al. |
| 2013/0053976 A1 | 2/2013 | Gugler et al. |
| 2013/0150858 A1 | 6/2013 | Primiano et al. |
| 2013/0172892 A1 | 7/2013 | Servidio et al. |
| 2013/0211536 A1 | 8/2013 | Metzger et al. |
| 2013/0264749 A1 | 10/2013 | Jones et al. |
| 2013/0268085 A1 | 10/2013 | Dong et al. |
| 2014/0222153 A1 | 8/2014 | Bonin, Jr. et al. |
| 2014/0276882 A1 | 9/2014 | Collazo et al. |
| 2014/0277528 A1 | 9/2014 | Mines et al. |
| 2014/0277567 A1 | 9/2014 | Collazo et al. |
| 2015/0105779 A1 | 4/2015 | Smith et al. |
| 2015/0190150 A1 | 7/2015 | Primiano et al. |
| 2015/0282935 A1 | 10/2015 | Kuldjanov et al. |
| 2015/0366567 A1 | 12/2015 | Servidio et al. |
| 2017/0189196 A1 | 7/2017 | Chavarria et al. |
| 2019/0358044 A1 | 11/2019 | Servidio et al. |
| 2023/0233328 A1 | 7/2023 | Cullum et al. |

FOREIGN PATENT DOCUMENTS

| | | |
|---|---|---|
| DE | 102010044571 A1 | 3/2012 |
| EP | 0016480 A1 | 10/1980 |
| EP | 220803 A2 | 5/1987 |
| EP | 0806921 B1 | 1/2003 |
| EP | 1570812 A1 | 9/2005 |
| EP | 2168506 A1 | 3/2010 |
| EP | 2168586 A1 | 3/2010 |
| EP | 2181672 A1 | 5/2010 |
| GB | 2159416 A | 12/1985 |
| WO | 03094698 A2 | 11/2003 |
| WO | 2006127486 A2 | 11/2006 |
| WO | 2008069800 A1 | 6/2008 |
| WO | 2009094698 A1 | 8/2009 |

OTHER PUBLICATIONS

Extended European Search Report issued in Appln. No. 221885775.5 dated Dec. 1, 2022 (4 pages).

Stryker, Restoration: Acetabular Wedge Augment System, Copyright © 2011 Stryker, Aug. 2011, pp. 1-6.

(56) References Cited

OTHER PUBLICATIONS

International Search Report and Written Opinion for Application No. PCT/US2012/068473 dated Mar. 8, 2013.

Partial International Search Report dated Mar. 15, 2013 for Application No. PCT/US2012/072087.

Jones et al., U.S. Appl. No. 13/441,154, filed Apr. 6, 2012, titled "Surface Modified Unit Cell Lattice Structures for Optimized Secure Freeform Fabrication".

International Search Report and Written Opinion for Application No. PCT/US2012/072087 dated May 2, 2013.

Schreurs, et al., Femoral Component Revision with Use of Impaction Bone-Grafting and a Cemented Polished Stem. Surgical Technique, The Journal of Bone & Joint Surgery, Sep. 2006, pp. 259-274.

Lonner, et al., Impaction Grafting and Wire Mesh for Uncontained Defects in Revision Knee Arthroplasty, Clinical Orthopaedics and Related Research, No. 404, pp. 145-151, Copyright Nov. 2002, Lippincott Williams & Wilkins, Inc.

Stryker Howmedica Osteonics, X-change Revision Instruments System, Copyright Howmedica Osteonics, Sep. 2001.

Knee Revision Product Portfolio, DePuy International Ltd., a Johnson & Johnson Company, Cat. No. 9075-40-000 version 1, Copyright 2009.

Zimmer, Trabecular Metal, Tibial and Femoral Cones Surgical Techniques, Copyright 2011.

Extended European Search Report for Application No. EP14159399 dated Jun. 6, 2014.

Extended European Search Report with Written Opinion for Application No. 20173076 completed Aug. 12, 2020, 6 pages.

Mcqueen, Wichita Fusion Nail Surgical Technique, Oct. 2006, 12 pages, Stryker.

Depuy, S-Rom Noiles Rotating Hinge, Surgical Technique and Reference Guide, 2002, 44 pages.

Stryker, Restoration: Acetabular Wedge Augment System, Surgical Protocol, Copyright © 2012 Stryker, pp. 1-20.

* cited by examiner

FIG. 3B
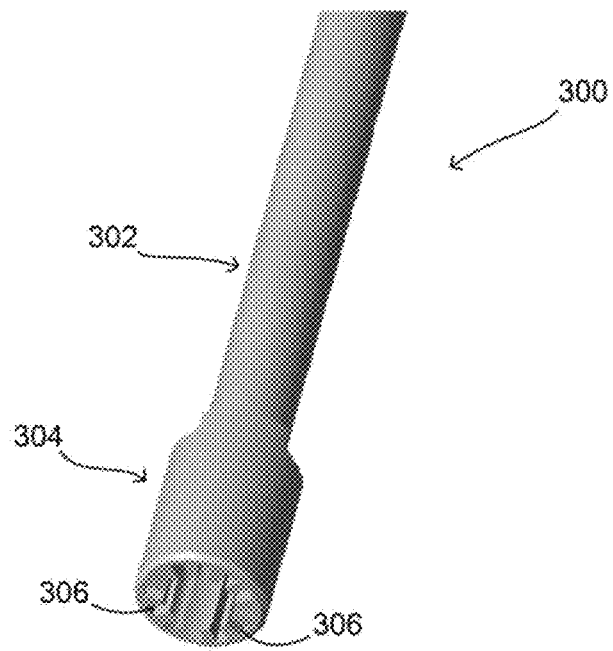
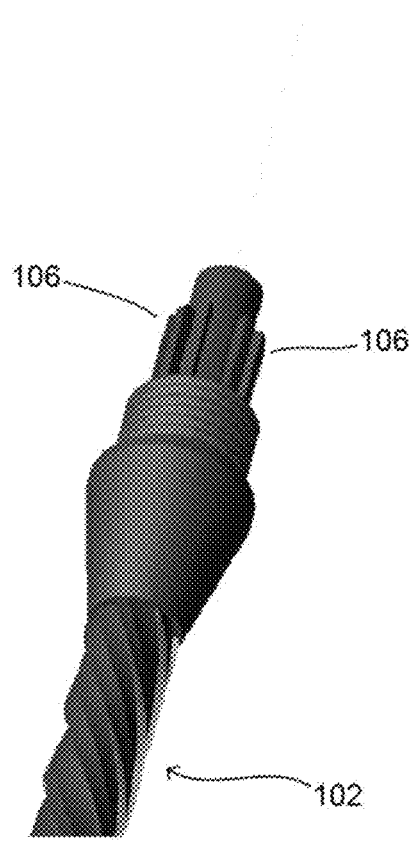

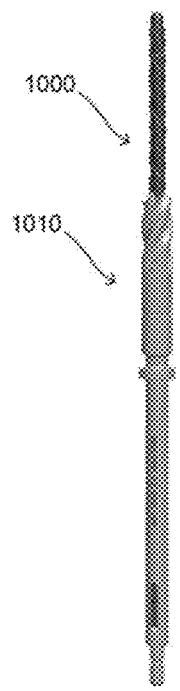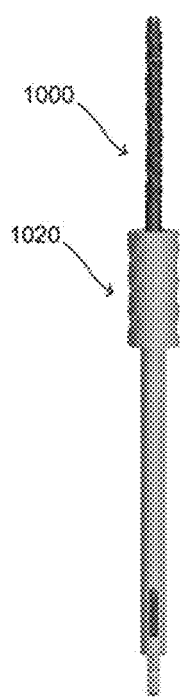

SYSTEMS AND METHODS FOR PREPARING BONE VOIDS TO RECEIVE A PROSTHESIS

CROSS-REFERENCE TO RELATED APPLICATIONS

The present application is a continuation of U.S. application Ser. No. 17/496,996, filed Oct. 8, 2021, now U.S. Pat. No. 11,877,757, which is a continuation of U.S. application Ser. No. 16/274,684, filed on Feb. 13, 2019, now U.S. Pat. No. 11,172,940, which is a continuation of U.S. application Ser. No. 15/597,851, filed on May 17, 2017, now U.S. Pat. No. 10,265,083, which is a continuation of U.S. application Ser. No. 14/837,437, filed Aug. 27, 2015, now U.S. Pat. No. 10,213,215, which is a continuation of U.S. application Ser. No. 13/730,082, filed Dec. 28, 2012, now U.S. Pat. No. 9,149,282, which claims the benefit of the filing date of U.S. Provisional Application No. 61/581,736, filed Dec. 30, 2011, all of which are hereby incorporated herein by reference.

FIELD OF THE INVENTION

The present invention relates to surgical instruments for preparing a bone to receive a joint prosthesis system, and in particular to guided surgical reaming instruments and bone void fillers for use in total knee replacement revision procedures.

BACKGROUND OF THE INVENTION

Joint replacement surgery is a common orthopedic procedure for joints such as the shoulder, hip, knee, ankle and wrist. Prior to implanting prosthetic components in a joint of a patient, a surgeon generally has to resect at least a portion of the patient's native bone in order to create a platform and/or recess or cavity for receiving at least a portion of the prosthetic components being implanted. During the process of resecting bone, a surgeon typically makes an effort to only resect the amount of bone that is needed in order to implant the prosthetic components properly. In other words, it is generally the goal to maintain as much native bone within the joint.

When prosthetic components fail for any one of a variety of reasons, a revision procedure is often necessary. Although defects in a bone adjacent a joint, such as the hip or knee, may occur naturally due to wear and arthritis of the joint and congenital deformities, the removal of a failed prosthetic component also creates an issue with maintaining native bone. Specifically, when prosthetic components are removed from the joint during a revision procedure, it is common for there to have been further native bone loss in the area adjacent the original implant position of the prosthetic components due to movement of the components after implantation or even further degeneration of the bone. For instance, when bone voids are observed in either the proximal tibia or distal femur, or both, after removal of a previously implanted component, it is standard surgical practice to fill those voids as part of the surgical procedure. One way of filling those voids is to use weight bearing void fillers, typically made of an implant-grade metal such as titanium. Such void fillers may be referred to as metaphyseal reconstruction devices (MRD). The name MRD reflects functions such as weight bearing that these devices generally provide.

Because voids in bone are typically irregular in shape, preparation of the bone void area is typically required prior to implantation of a MRD. This preparation (typically by reaming, broaching or milling) ensures there is sufficient room in the bone cavity for the MRD. An accurate fit between the shaped bone cavity and the MRD is important for establishing joint line, and allowing for weight bearing and bone remodeling during the recovery process.

Different methods may be employed to attempt to prepare the bone void area to create an accurate fit between the shaped bone cavity and the MRD. One method is to ream along the intramedullary (IM) axis, followed by broaching. Another method is to ream on the IM axis, followed by freehand burring or bone removal using a rongeur, which may also be followed by broaching. With these methods any reaming performed occurs on the IM axis only, so that void areas at a distance from the IM axis, which commonly occur, can only be resected using manual methods. Also, freehand bone removal, either powered or unpowered, such as by burr or rongeur, often does not produce accurate cavity shapes to receive prosthetic components having predefined configurations. A typical result of the above mentioned methods is that areas remain where the outer walls of the MRD do not contact the cavity, which may lead to undesirable stress distribution and possible loss of bone regrowth. Also typical is the time consuming requirement of iterative bone removal, with multiple checks against the MRD, to obtain a correct fit.

Therefore, there is a need for a surgical instrument that creates accurate bone cavity geometries and minimizes the necessity for freehand bone removal. There is also a need for enabling surgeons to create bone cavities offset from the IM canal with a fully guided system.

BRIEF SUMMARY OF THE INVENTION

According to one aspect of the present invention, a device for implantation into a bone void. The device comprises a sidewall defining a cavity for receipt of a portion of a joint prosthesis. The device further comprises a selectively removable portion formed in the sidewall, wherein removal of the selectively removable portion forms a gap in the sidewall.

In another embodiment, the device may include a first body having a first sidewall and a first cavity defining a first longitudinal axis. The device may further include a second body connected to the first body. The second body has a second sidewall and a second cavity in communication with the first cavity. The second cavity defines a second longitudinal axis, wherein at least one of the first and second sidewalls includes the selectively removable portion and removal of the selectively removable portion forms a gap in the respective sidewall.

In another aspect of the present invention, the device may include an adhesive anti-rotation feature connected to the inner surface of the first body.

The anti-rotation feature may be realized in the form of a plurality of protrusions radially extending into the cavity from the inner surface of the first body.

According to another aspect of the present invention, the first body may include a clearance channel extending through the first sidewall forming a gap for receipt of a portion of the prosthesis.

The first body may be realized in a form that is substantially frustoconical, such that a proximal end has a larger diameter than a distal end of the first body.

In one embodiment, the first body may include a neck extending from the distal end of the first body for stabilizing the device in the bone.

The first body and second body may be realized where each have an inner surface made from a solid biocompatible material and an outer surface made from a porous biocompatible material.

Further, the selectively removable portion may be realized where it is made entirely of the porous biocompatible material.

Yet another aspect of the present invention is a surgical system for forming a void in a bone. The surgical system includes a support member configured to be securely positioned within an intramedullary canal of the bone. Further, the surgical system includes an offset guide member having a longitudinal axis. The offset guide member is configured to attach to the support member so that the longitudinal axis of the offset guide member is in a fixed and offset relation with the intramedullary canal of the bone. Additionally, the surgical system includes a cutting member for forming an offset bone void having a cutting head attached. The cutting member is configured to slidably engage the offset guide member along the longitudinal axis of the offset guide member.

In one embodiment, the support member includes radially projecting flanges extending outward from the proximal end of the support member. Further, the offset guide member includes a cannulated distal end. The cannulated distal end has an inner surface and radially extending flanges extending inward from the inner surface and is configured to engage the radially projecting flanges of the support member.

In another embodiment of the present invention, the support member may comprise a cone trial and a guide shaft. The cone trial is configured to be securely inserted into a central bone void, and the guide shaft is configured to securely connect to the cone trial such that distal and rotational movement is prohibited.

Further, the offset guide member may have a locking body and a cutting guide component. The locking body is configured to lock the offset guide member to the guide shaft. The cutting guide component has a longitudinal axis and is configured to slidably receive the cutting member along the longitudinal axis of the cutting guide component. The cutting guide component is fixed to the locking body, wherein locking the locking body to the guide shaft fixes the longitudinal axis of the cutting guide component in an offset relation to the intramedullary canal of the bone.

In another aspect of the present invention, the offset guide member may include an offset driver. The offset driver includes a longitudinal axis and is configured to attach to the support member so that the longitudinal axis of the offset driver is in a fixed and offset relation with the intramedullary canal of the bone. The offset guide member further includes an offset driver sleeve having longitudinal axis and is configured to slide over and attach to the offset driver so that the longitudinal axis of the offset driver sleeve is in an offset and fixed relation with the longitudinal axis of the offset driver and the intramedullary canal of the bone.

In one embodiment, the cutting member may be a broach. Additionally the surgical system may further comprise a second stage broaching tool configured to slidably engage the offset guide member along the offset longitudinal axis of the offset guide member. The second stage broaching tool is shaped to substantially conform to the shape of a bone void filling device.

In another embodiment, the cutting member may be a reamer.

According to another aspect of the present invention, a surgical method for forming a void in bone. The surgical method comprises the step of positioning a support member securely within an intramedullary canal of a bone. The method further includes the step of attaching a guide member having a longitudinal axis to the support member in a fixed and offset relation to the intramedullary canal.

Additionally, the method includes connecting a cutting member having a cutting head to the guide member in a slidable arrangement along the longitudinal axis of the guide member such that the cutting head faces a first bone segment. Further, the method comprises cutting the first bone segment along the longitudinal axis of the guide member, thereby forming a first offset bone void.

In one embodiment, the cutting member may be a reamer.

In another embodiment, the cutting member may be a broach.

Another aspect of the present invention, the method further includes the step of detaching the guide member and cutting member from the support member. Further still, the method comprises a step of reconnecting the guide member and cutting member to the support member so that the cutting head faces a second bone segment. Additionally, there is a step of cutting the second bone segment along the longitudinal axis of the guide member, thereby forming a second offset bone void.

In one embodiment of the method, the method may comprise the step of disconnecting the cutting member from the guide member. Further, there may be a step of attaching a guide member sleeve having a longitudinal axis to the guide member so the longitudinal axis of the guide member sleeve is offset and fixed with respect to the longitudinal axis of the guide member and intramedullary canal of the bone. Additionally, the method may include a step of connecting a cutting member to the guide member sleeve in a slidable arrangement along the longitudinal axis of the guide member sleeve so that the cutting head faces a second bone segment. There is also a step of cutting the second bone segment along the longitudinal axis of the guide member sleeve, thereby forming a second offset bone void.

A further aspect of the present invention, the method may include the step of detaching the guide member, guide member sleeve, and cutting member from the support member. Further, there may be a step of reconnecting the guide member, guide member sleeve, and cutting member to the support member such that the cutting head faces a third bone segment. Additionally, the method may include cutting the third bone segment along the longitudinal axis of the guide member sleeve, thereby forming a third offset bone void.

BRIEF DESCRIPTION OF THE FIGURES

FIG. 3B shows an exploded perspective view of the IM reamer and the offset driver shown in FIG. 3A.

FIG. 10A shows an front view of one embodiment of an IM reamer.

FIG. 10B shows a bushing assembled with the IM reamer of FIG. 10A.

FIG. 10C shows a cylindrical reamer assembled with the IM reamer of FIG. 10A.

DETAILED DESCRIPTION

As used herein, when referring to the surgical reaming instruments of the present invention, the term "proximal" means closer to the surgeon or in a direction toward the surgeon and the term "distal" means more distant from the surgeon or in a direction away from the surgeon. The term "anterior" means towards the front part of the body or the face and the term "posterior" means towards the back of the body. The term "medial" means toward the midline of the body and the term "lateral" means away from the midline of the body.

Figure 1:
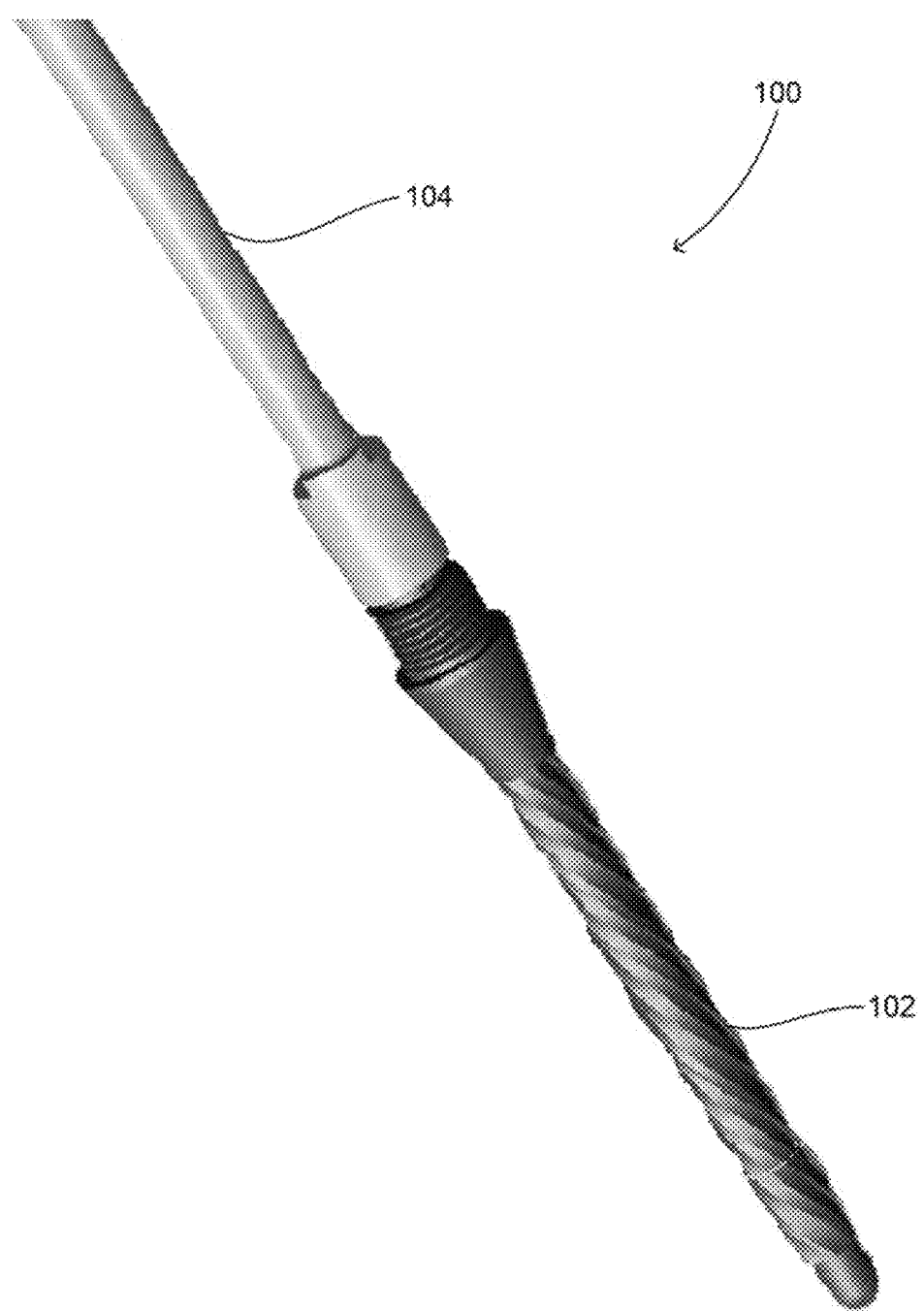
FIG. 1 shows an assembled perspective view of a two part reamer and a driver having longitudinal axes thereof in alignment.

FIG. 1 illustrates a side view of a two part reamer 100. The two part reamer consists of an IM reamer 102 and inline driver 104. In the assembled position as shown, longitudinal axes of the IM reamer 102 and inline driver 104 are coaxial. In a revision procedure, the initial step after removing the prosthesis located in the bone is to ream the bone generally along a longitudinal axis thereof. In total knee revision procedures, for example, the bone is preferably reamed along the IM canal. This can be accomplished, for example, by the use of two part reamer 100. Once the initial IM reaming step is completed, it may be determined that the patient would benefit from a MRD implanted along an axis of the bone offset from the IM axis created in the initial reaming step. To prepare the bone to accept such an MRD, another drilling step may be performed on the desired axis for MRD implantation.

Figure 2A:
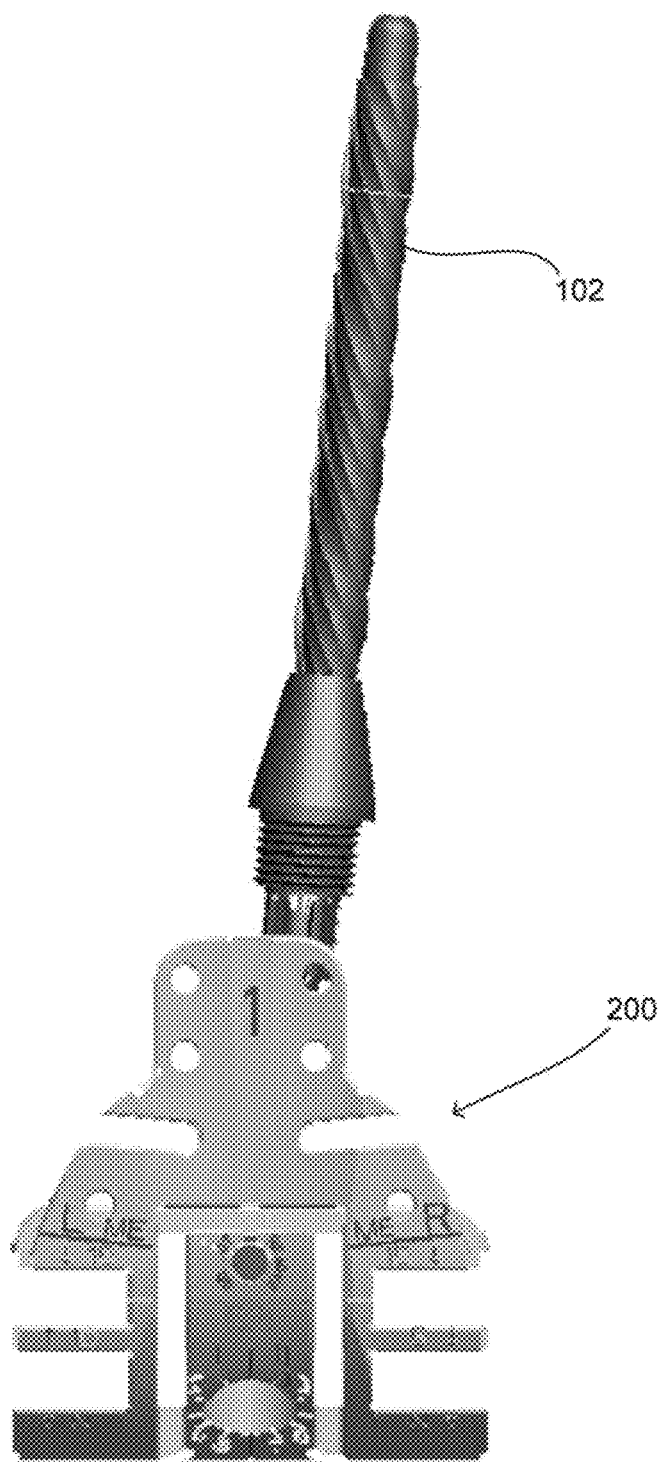
FIG. 2A shows a perspective view of an IM reamer in conjunction with an alignment guide cutting jig being used to determine an offset axis.
Figure 2B:
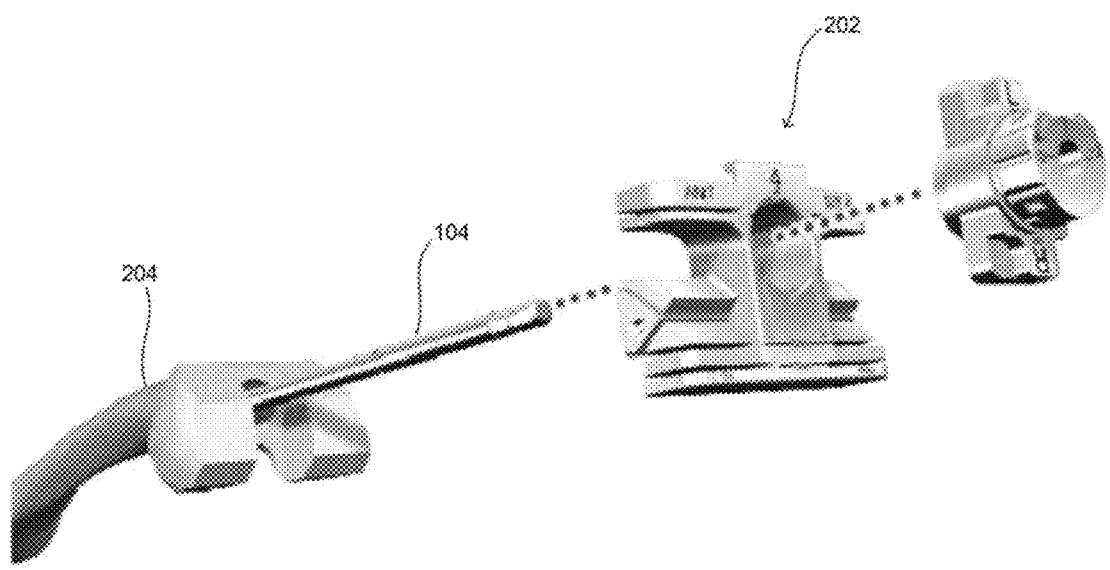
FIG. 2B shows an exploded perspective view of an IM reamer in conjunction with a cutting block being used to determine an offset axis.

FIGS. 2A and 2B illustrate different methods for determining the desired position of the offset axis. Referring to FIG. 2A, an alignment guide cutting jig 200 is shown. The alignment guide cutting jig 200 can be used to determine the desired location of the offset axis in the bone. Generally, alignment guide cutting jig 200 is used with an adapter (not shown). FIG. 2B shows a cutting block 202 being used in conjunction with the inline driver 104 of the two part reamer 100 to align the offset axis desired for bone 204. Once the desired location for the offset axis is chosen, the position is recorded and the proper offset driver 300 (discussed below) is chosen to achieve the desired offset axis.

Figure 3A:
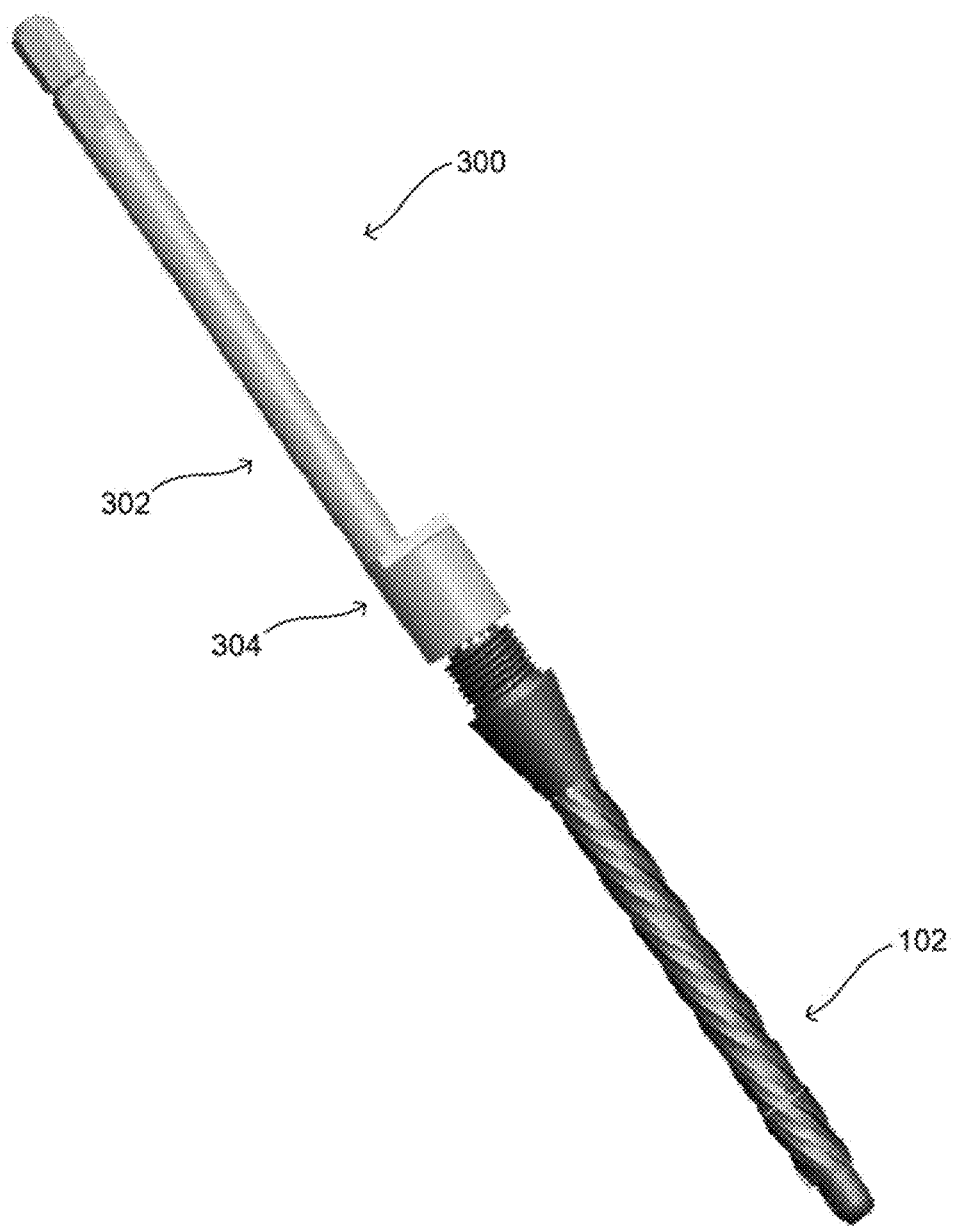
FIG. 3A shows an assembled perspective view of an IM reamer and a driver having an offset adapter.

FIGS. 3A and 3B show an embodiment of an offset driver 300 having a shaft 302 with a longitudinal axis and an adapter end 304 with a longitudinal axis offset from the longitudinal axis of the shaft 302. FIGS. 3A and 3B show offset driver 300 before and after engagement with the IM reamer 102. As illustrated in FIG. 3A, the offset driver 300 includes a shaft 302 that is offset from the axis of the IM reamer 102, and thus offset from the axis of the IM canal. The offset driver 300 further includes an adapter end 304 at the distal end of the offset driver 300. The adapter end 304 can be at least partially hollow to engage a proximal end of the IM reamer 102. As illustrated in FIG. 3B, the distal end of the offset driver 300 and the proximal end of the IM reamer 102 can include features to help create a secure engagement between the two. For example, the adapter end 304 of offset driver 300 can include a plurality of radially projecting flanges 306 spaced circumferentially around the hollow inside of the adapter end 304. The void spaces between radially projecting flanges 306 can be designed to mate with a set of complementary radially projecting flanges 106 at the proximal end of the IM reamer 102. Once the offset driver 300 is securely engaged to the IM reamer 102, the surgical instrument can be further prepared to ream and/or broach the bone.

Figure 4A:
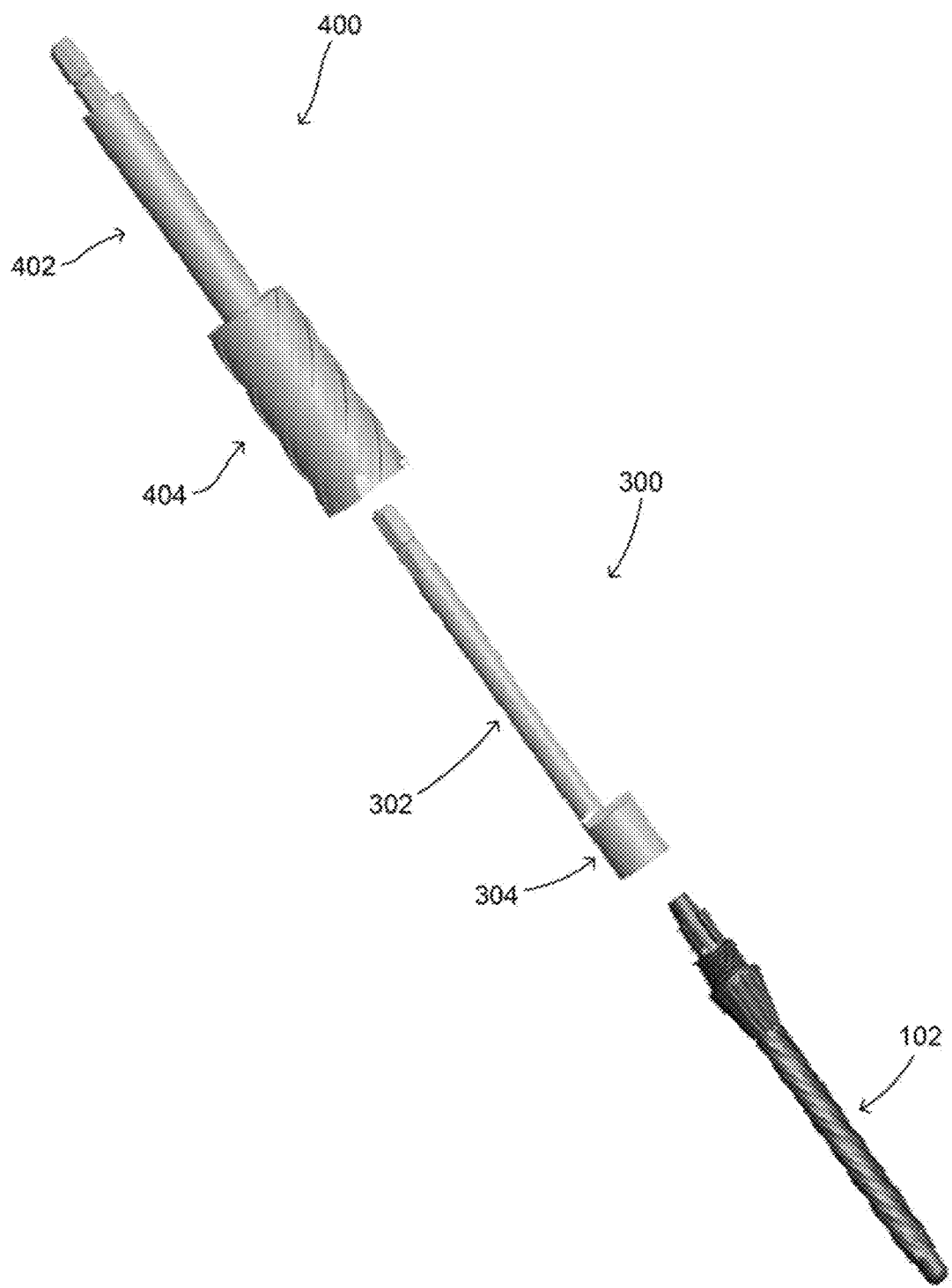
FIG. 4A shows an exploded perspective view of an offset reamer, an offset driver and an IM reamer.
Figure 4B:
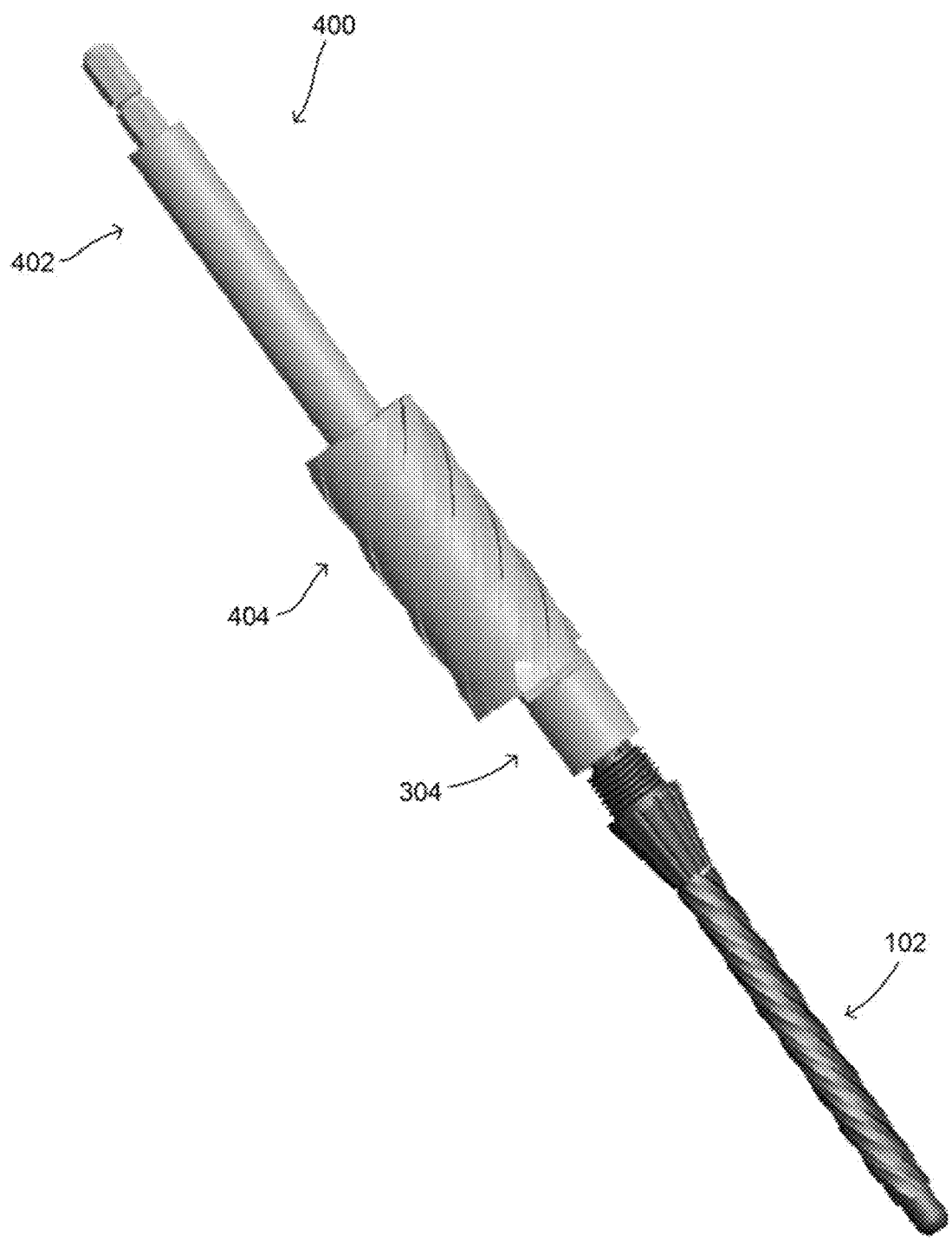
FIG. 4B shows an assembled perspective view of the offset reamer, the offset driver and IM reamer shown in FIG. 4A.

Referring now to FIG. 4A, an exploded view of an offset reamer 400, offset driver 300, and IM reamer 102 is shown. The offset reamer 400 includes a reaming head 404 and reaming shaft 402. The reaming shaft 402 and reaming head 404 are coaxial with the shaft 302 of the offset driver 300, and thus are also offset from the axis of the IM reamer 102. As seen in FIG. 4B, a hollow inner cylinder of offset reamer 400 is slipped over the shaft 302 of offset driver 300 to position the reaming head 404 coaxial with the desired offset reaming axis as determined, for example, using a technique described with reference to FIG. 2A or 2B. At this point, the user can use the offset reamer 400 to create the first offset bone cavity in preparation for MRD implantation.

Figure 5A:
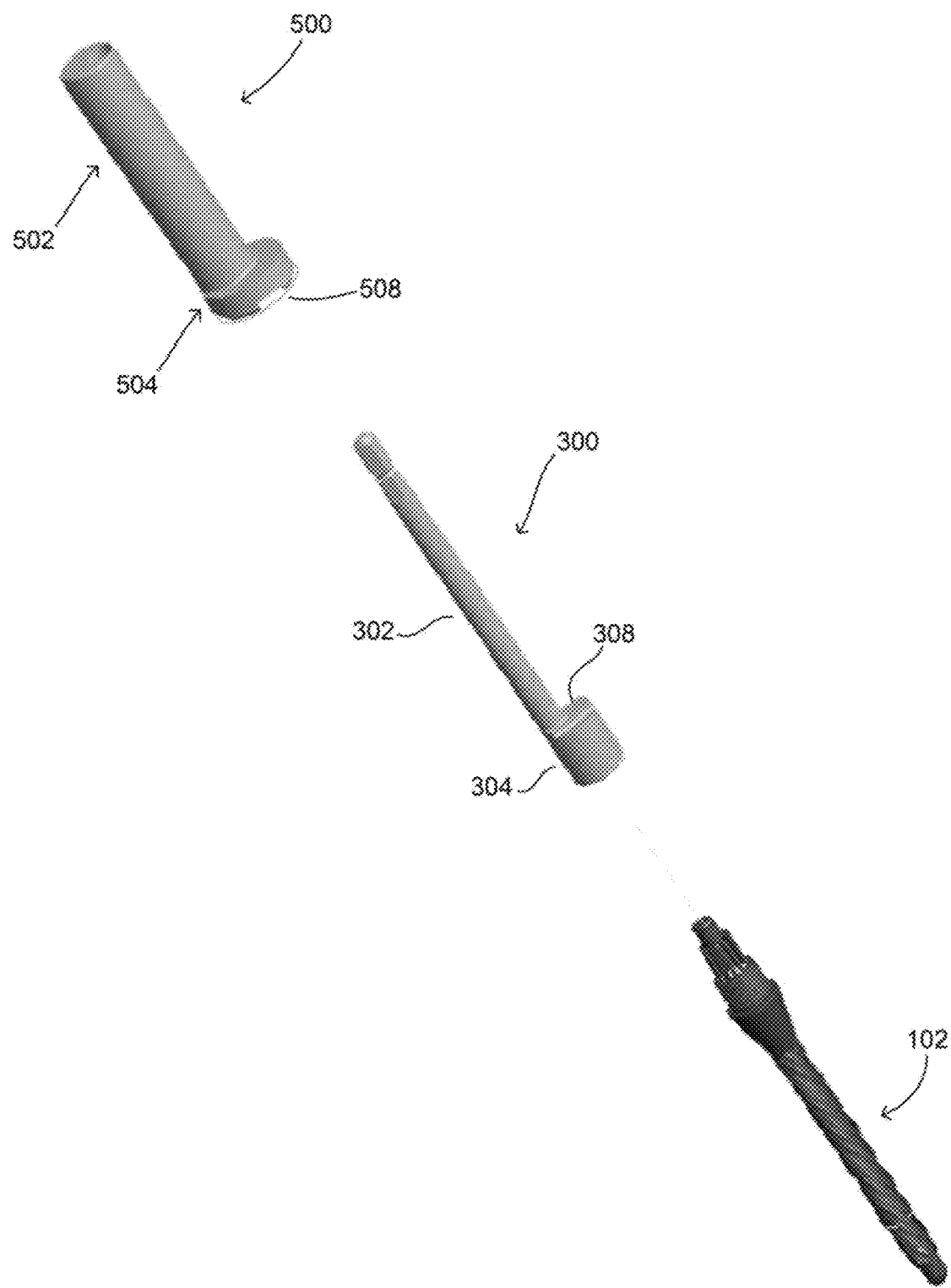
FIG. 5A shows an exploded perspective view of an offset reaming guide, an offset driver, and an IM reamer.
Figure 5B:
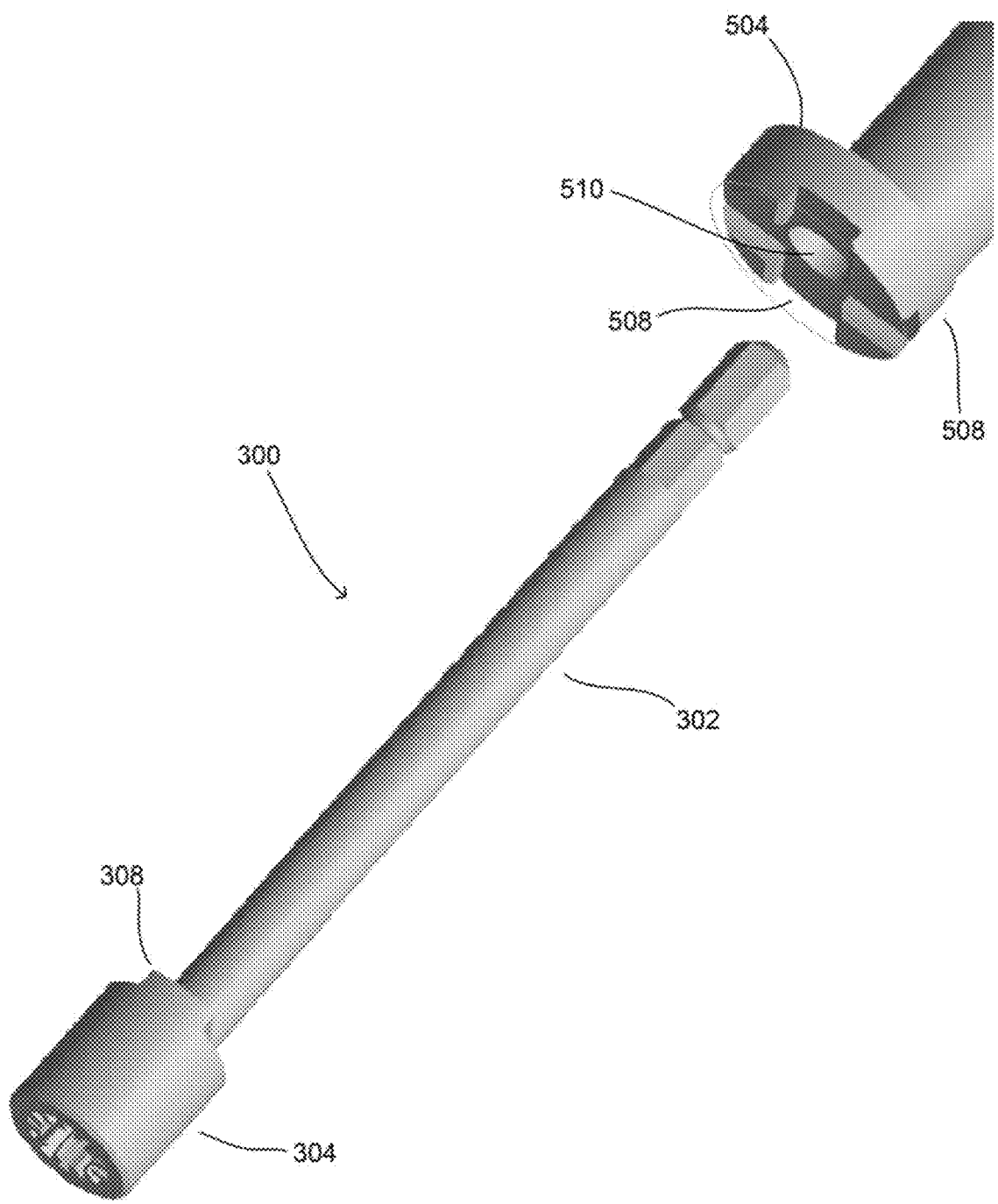
FIG. 5B shows an enlarged exploded perspective view of the offset reaming guide and the offset driver shown in FIG. 5A.

Once the first offset bone cavity is created, the offset reamer 400 can be removed and the surgical instrument can be further prepared to create medial and lateral bone cavities to create a void space fully complementary with a structure of one embodiment of an MRD. FIG. 5A shows an exploded view of an offset reaming guide 500, offset driver 300, and IM reamer 102 for optionally forming additional bone cavities that are offset from the offset bone cavity formed by the offset reamer 400. Offset reaming guide 500 includes an offset reaming guide shaft 502 and reaming guide base 504. As seen in FIG. 5B, the distal end of reaming guide base 504 can include groove members 508 for locating and engaging with complementary groove members 308 on the proximal end of offset adapter end 304. The groove members 508 of the reaming guide base 504 may be symmetric about the longitudinal axis of the hollow cylindrical interior 510 of the offset reaming guide 500. This configuration allows the offset reaming guide 500 to be slipped over the shaft 302 of the offset driver 300 and engage the complementary groove members 308 of the offset adapter end 304 in more than one configuration. For example, a first engagement position of the offset reaming guide 500 can align the offset reaming guide shaft 502 for preparation of a bone cavity on the medial side of the first offset bone cavity created with offset reamer 400. The same offset reaming guide 500 can then be disengaged from the complementary groove members 308 of the offset adapter end 304, rotated 180 degrees, and then used to re-engage the complementary groove members 308 of the offset adapter end 304. In this second engagement position, the offset reaming guide shaft 502 can be aligned on the lateral side of the first offset bone cavity created with the offset reamer 400.

Figure 5C:
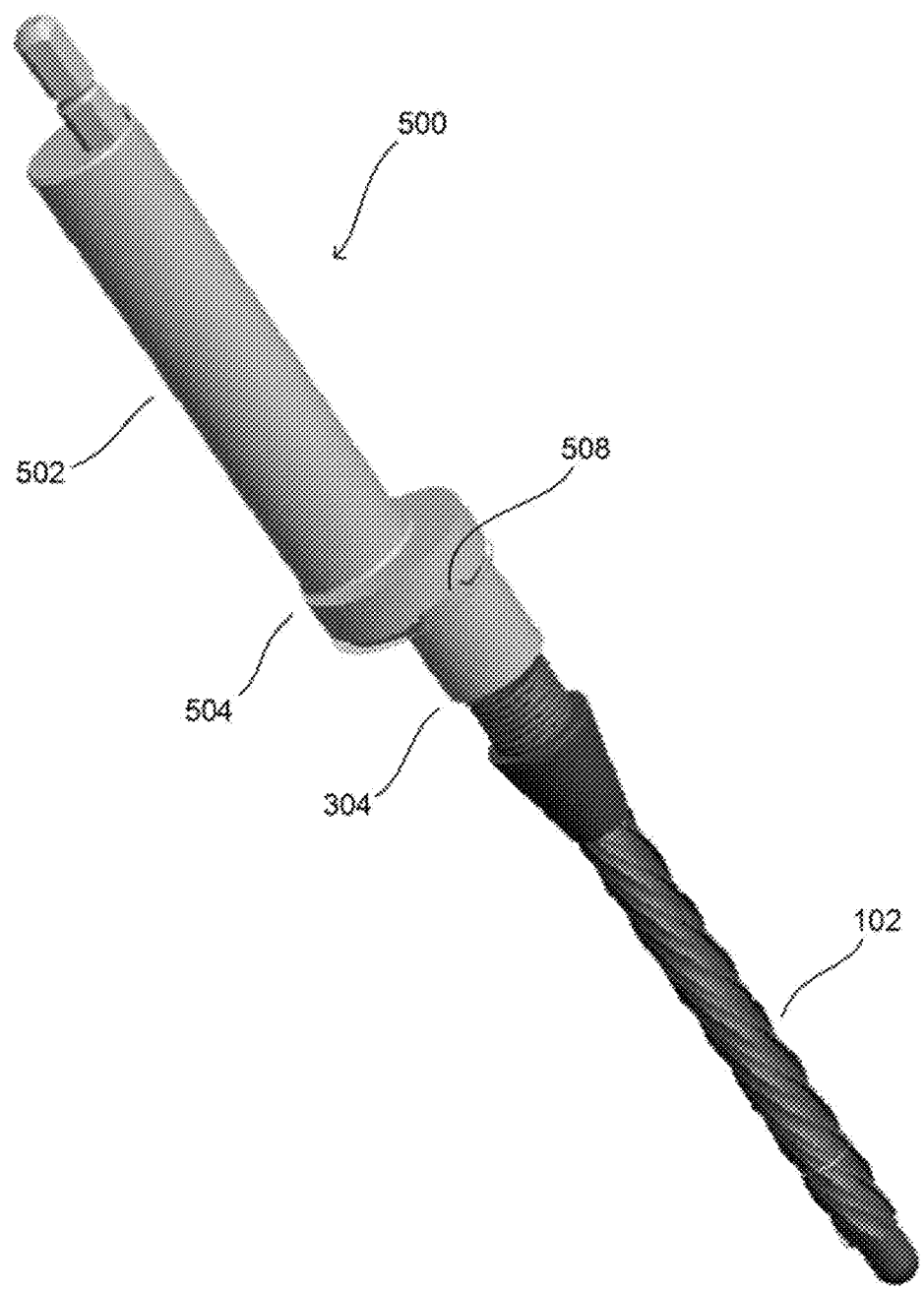
FIG. 5C shows an assembled perspective view of the offset reaming guide, the offset driver, and IM reamer shown in FIG. 5A.
Figure 5D:
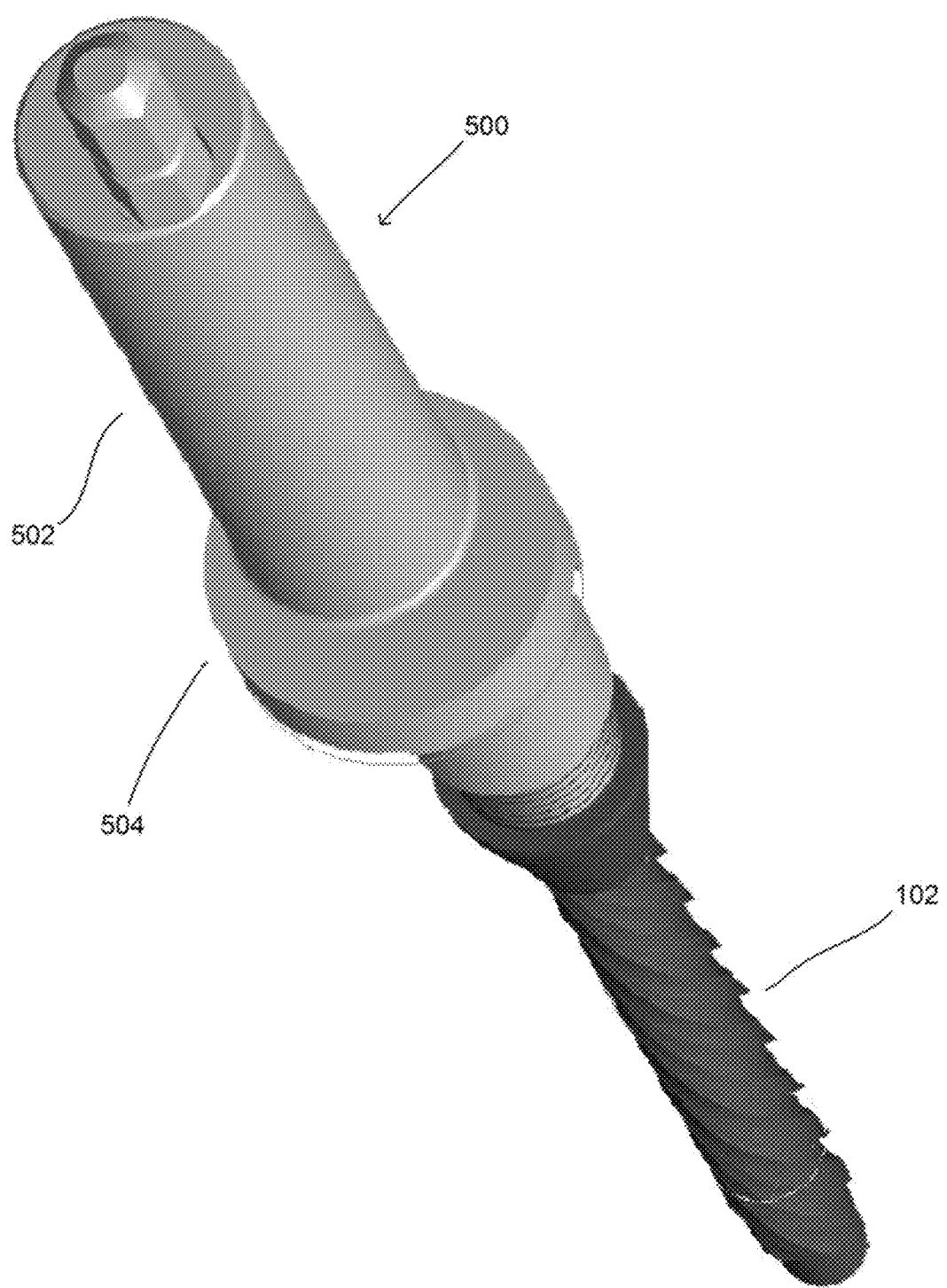
FIGS. 5D-E show perspective views of the assembly shown in FIG. 5C in first and second configurations.
Figure 5E:
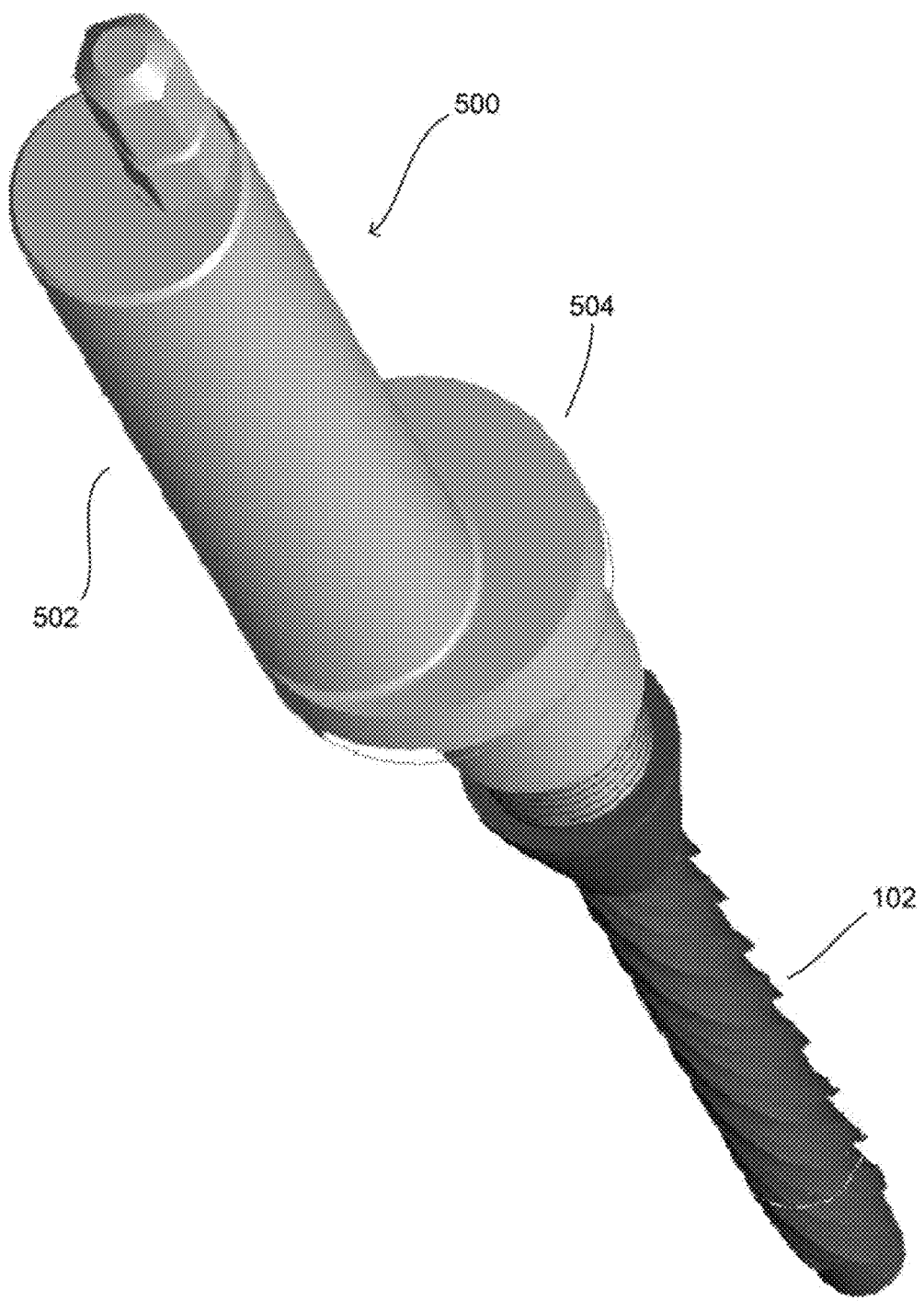

FIG. 5C illustrates the offset reaming guide 500 engaged with the offset driver 300 in a first engagement position. To further illustrate different alignment capabilities of the offset reaming guide 500, FIG. 5D illustrates a first medial reaming engagement position of the offset reaming guide 500, while FIG. 5E illustrates a second lateral reaming engagement position of the offset reaming guide 500. In these figures, the IM reamer 102 is shown in isolation for simplicity of illustration. However, in practice the IM reamer 102 would be engaged within a bone and an operator could change the offset reaming guide 500 from the position shown in FIG. 5D to the position shown in FIG. 5E without removing the IM reamer 102 from the bone. While not shown, the offset reaming guide 500 can be set in a plurality of different positions depending on the choice of the operator.

Figure 6A:
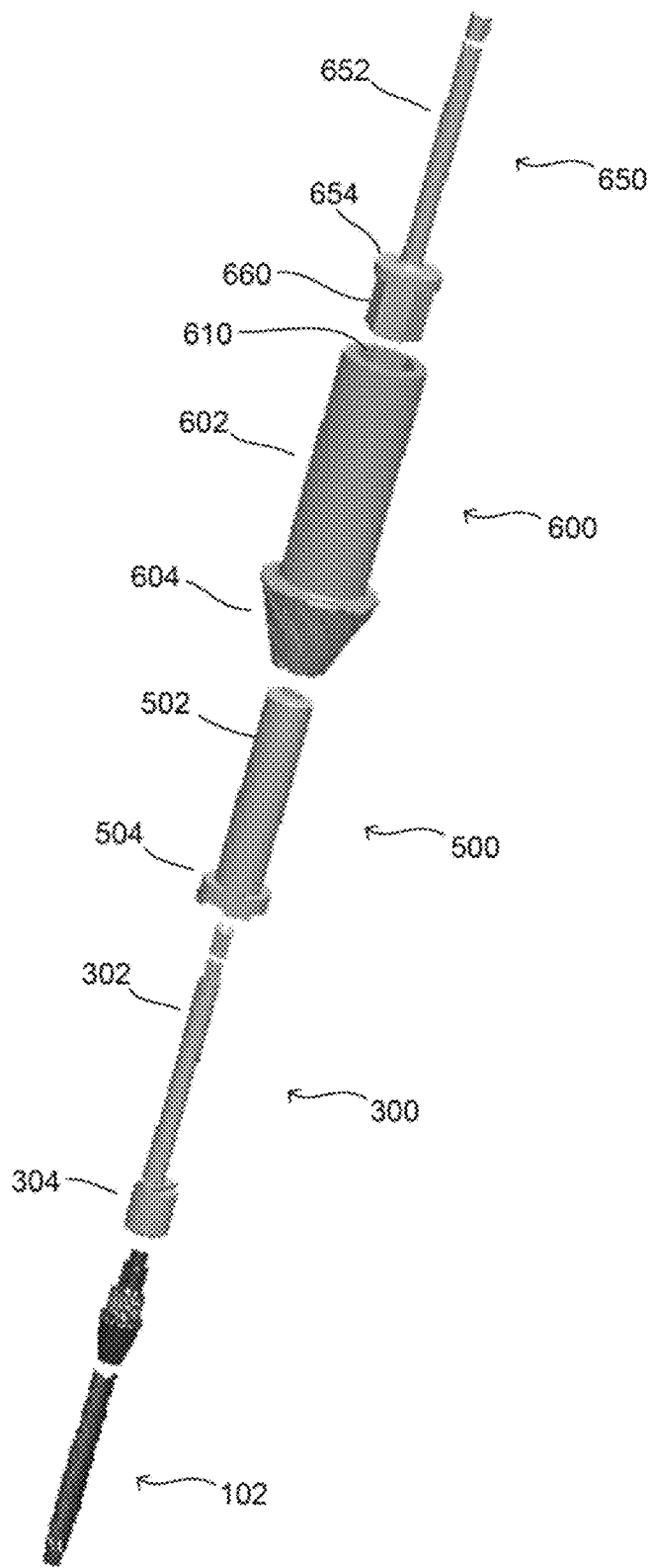
FIG. 6A shows an exploded perspective view of an inline driver, a conical reaming tool, an offset reaming guide, an offset driver and an IM reamer.
Figure 6B:
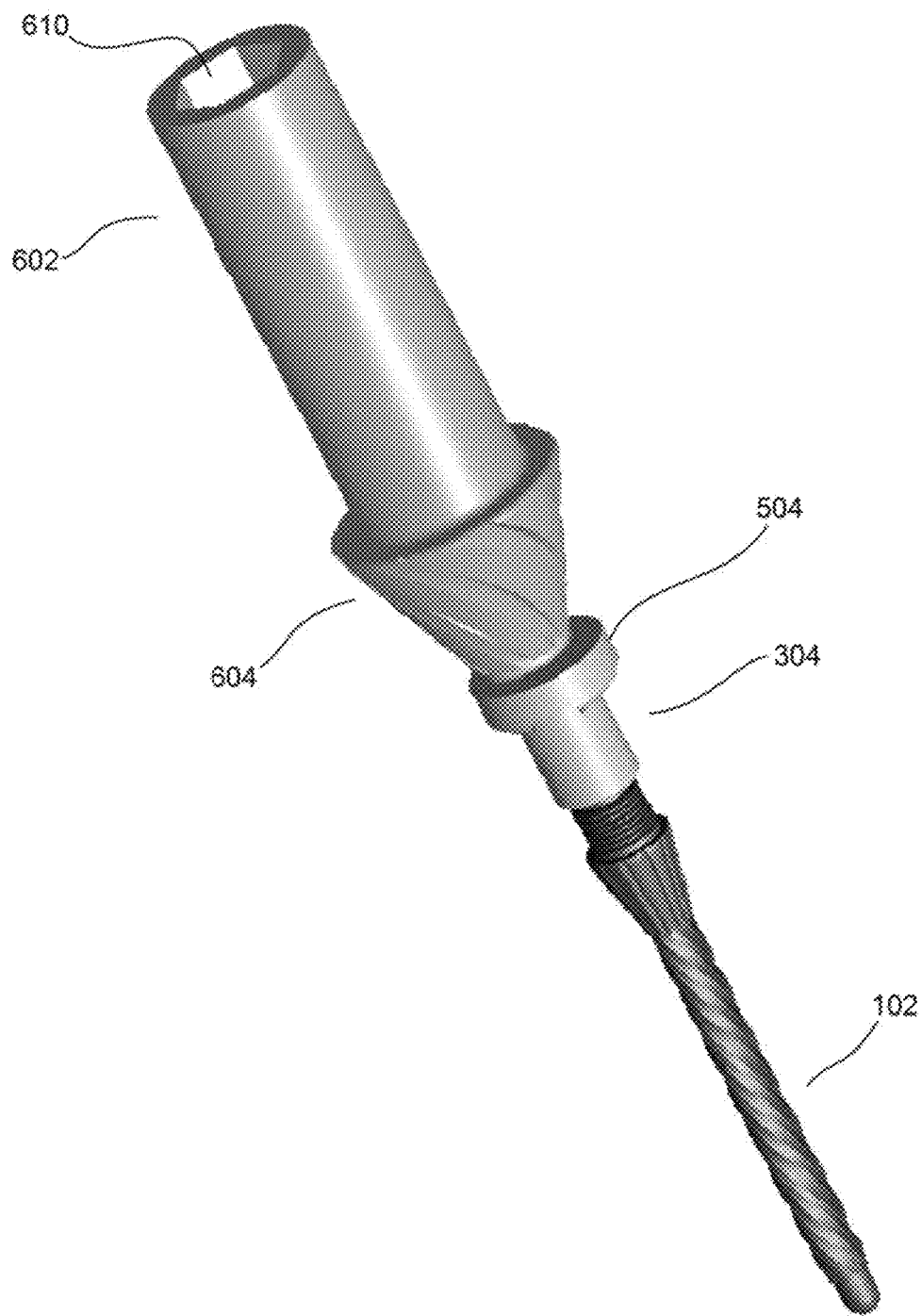
FIG. 6B shows an assembled perspective view of the conical reaming tool, the offset reaming guide, the offset driver and IM reamer shown in FIG. 6A.

After the reaming guide 500 engages the offset driver 300, the surgical instrument can further be prepared for creating another cavity in the bone, such as a medial or lateral bone cavity that is offset medially or laterally from the offset bone cavity created by the offset reamer 400. FIGS. 6A and 6B show exploded and assembled views of the surgical instrument prepared for creating conical bone cavities, such as medial and lateral bone cavities. As can be seen in the figures, the IM reamer 102, offset driver 300, and offset reaming guide 500 are assembled as seen in FIGS. 5A-E. A conical reamer 600, including conical reamer shaft 602, conical reaming head 604 and conical reamer shaft cavity 610, is slipped over offset reaming shaft 502. The proximal end of conical reamer shaft cavity 610 (best seen in FIG. 6B) can include a mating pattern, such as a hexagon, to engage a driver mechanism 650. The driver mechanism (only shown in FIG. 6A) includes a driver shaft 652 and a driver base 654. The distal end of driver base 654 can include a pattern 660, such as a hexagon pattern, that is complementary to the mating pattern on the proximal end of conical reamer shaft cavity 610. These complementary patterns can provide a secure engagement to improve the connection between the driver 650 and conical reamer 600 when the driver 650 is driving the conical reaming head 604 through a bone. The operator of the surgical device may drive the conical reamer 600 over the offset reaming guide 500 and into a bone of a patient to create a first conical bone cavity, for example, on the medial side of the initial cylindrical bone cavity created with the offset reamer 400. After the first conical bone cavity is completed, the operator may disengage the offset reaming guide 500 from the adapter end 304 of the offset driver 300, and rotate the reaming guide 500 to a second desired position. After re-engaging the reaming guide 500 to the adapter end 304 of the offset driver 300, the operator can create a second conical bone cavity, for example, on the lateral side of the initial cylindrical bone cavity created with the offset reamer 400.

Figure 7A:
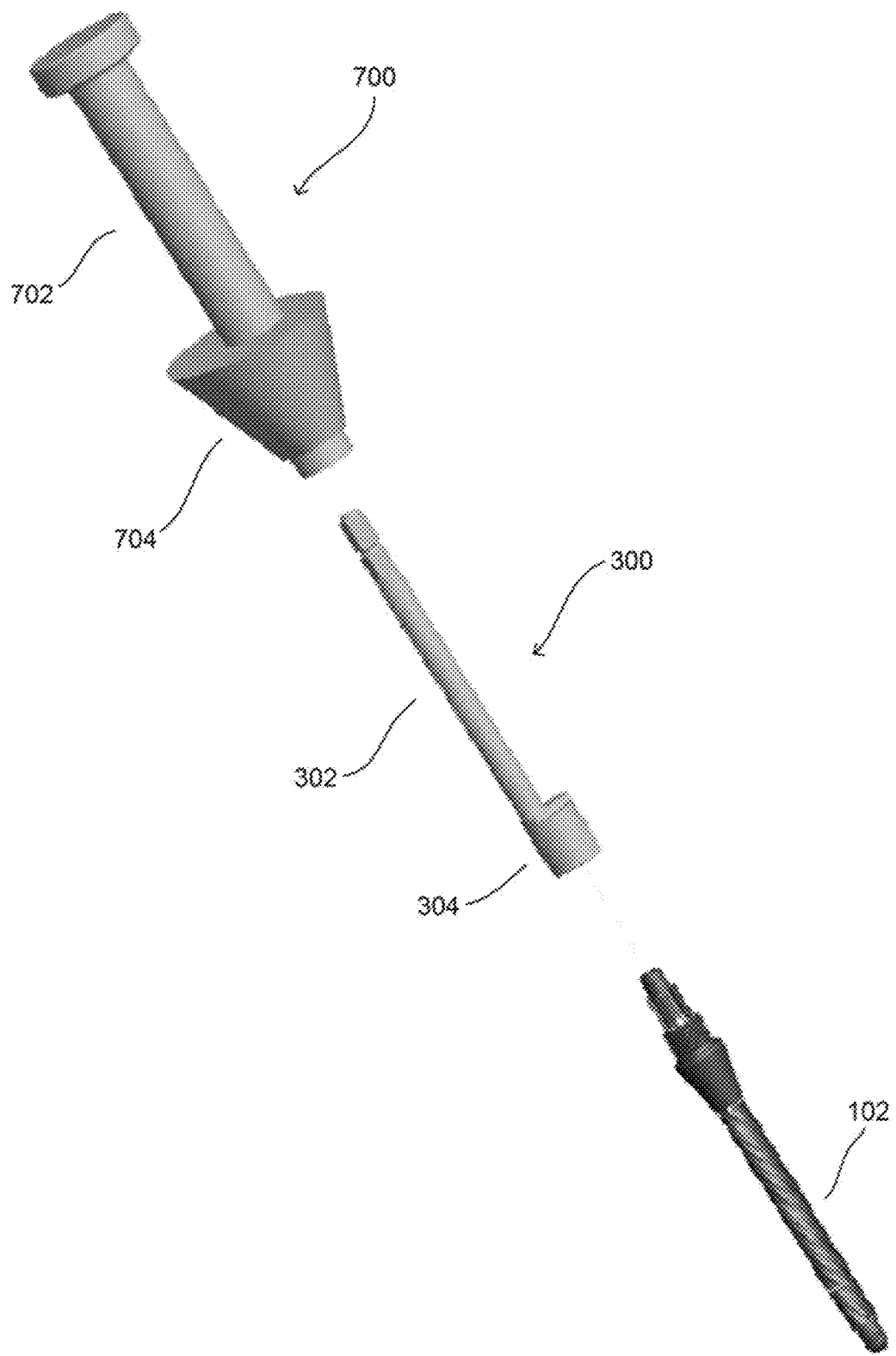
FIG. 7A shows an exploded perspective view of an offset broaching tool, an offset driver and an IM reamer.
Figure 7B:
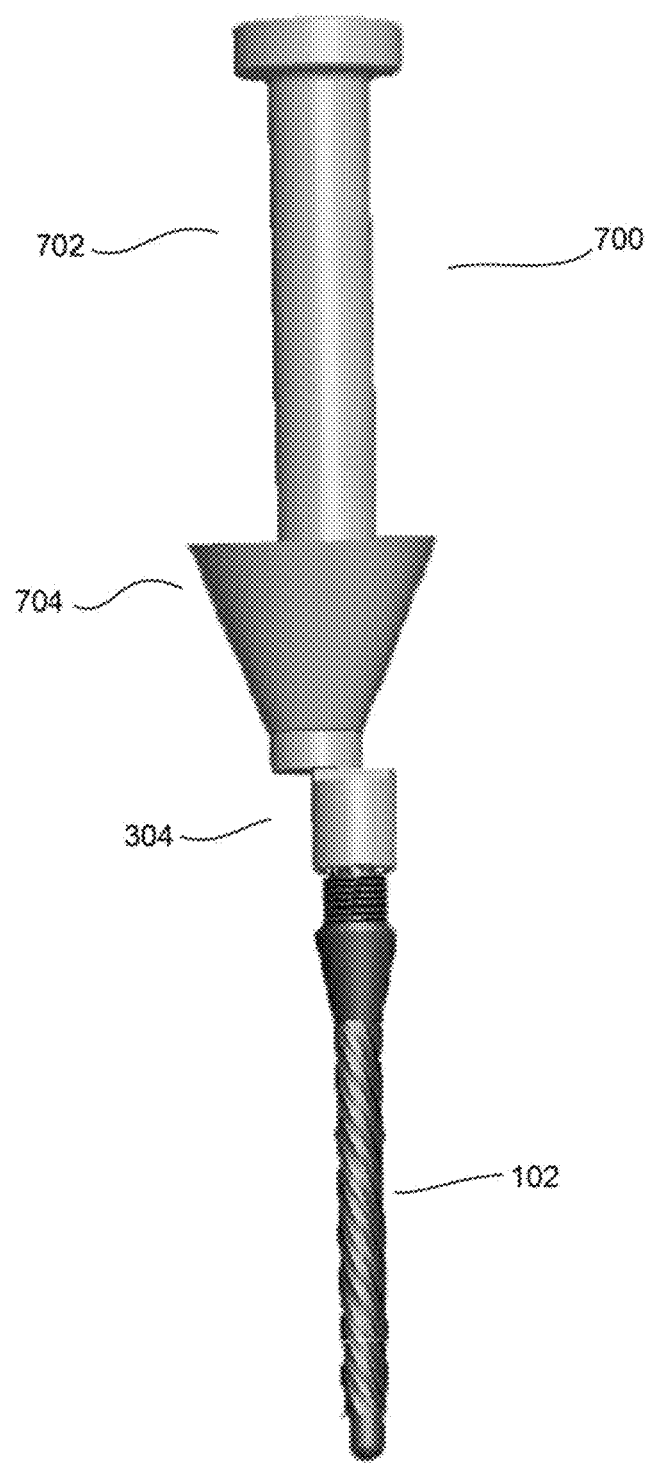
FIG. 7B shows an assembled perspective view of the offset broaching tool, the offset driver and IM reamer shown in FIG. 7A.

Besides reaming, broaching is an alternative method of preparing a femoral bone cavity. Referring now to FIG. 7A, an exploded view of an offset broaching tool 700, offset driver 300, and IM reamer 102 is shown. The offset broaching tool 700 includes a broaching head 704 and broaching shaft 702. The offset broaching shaft 702 and broaching head 704 are generally coaxial with the shaft 302 of the offset driver 300, and thus are also offset from the axis of the IM reamer 102. As seen in FIG. 7B, a hollow inner cylinder of offset broaching tool 700 is slipped over the shaft 302 of offset driver 300 to position the broaching head 704 coaxial with the desired offset reaming axis as determined, for example, by using a technique described with reference to FIG. 2A or 2B. Once offset broaching tool 700 is in position over the offset driver 300, a first offset bone cavity can be created in the bone. After this first offset bone cavity is created, the broaching tool 700 can be slipped off the offset driver 300 and the surgical tool can be further prepared to create additional bone cavities, such as medial and lateral bone cavities.

Figure 8A:
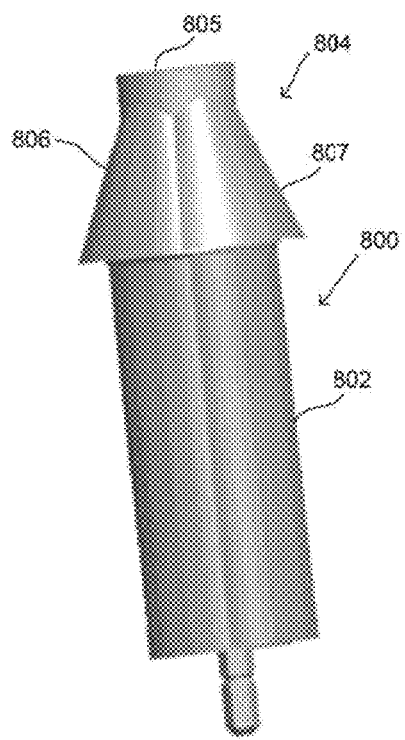
FIGS. 8A-C show different enlarged perspective views of a second stage broaching tool.
Figure 8B:
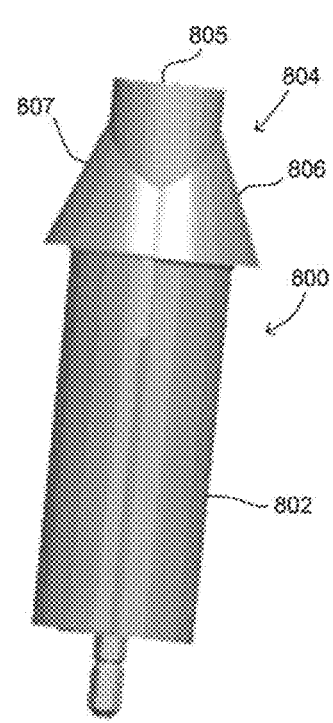
Figure 8C:
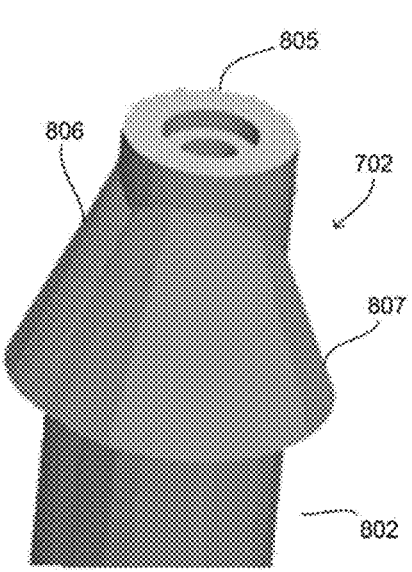

Referring now to FIGS. 8A-C, different views of a second stage broaching tool 800 are shown. In these figures, the IM reamer 102 is not pictured and the second stage broaching tool 800 has already been slipped over the offset driver 300. The adapter end 304 of the offset driver 300 is also omitted from these views for clarity of illustration. Second stage broaching tool 800 generally includes a shaft 802 and second stage broaching head 804. The second stage broaching head 804 includes a central cylinder shape 805 and a shape comprising two intersecting cones. The two intersecting cones generally correspond to a lateral side 806 and medial side 807 (posterior lateral and posterior medial sides best seen in FIG. 8C) of bone cavities to be created in the bone. Once the second stage broaching tool 800 is in place over the offset driver 300, as seen in FIGS. 8A-C, an operator of the surgical device can create medial and lateral bone cavities about the first offset bone cavity created with the first offset broaching tool 700, creating a bone cavity that defines the femoral MRD implant geometry with minimal bone removal steps.

Figure 9A:
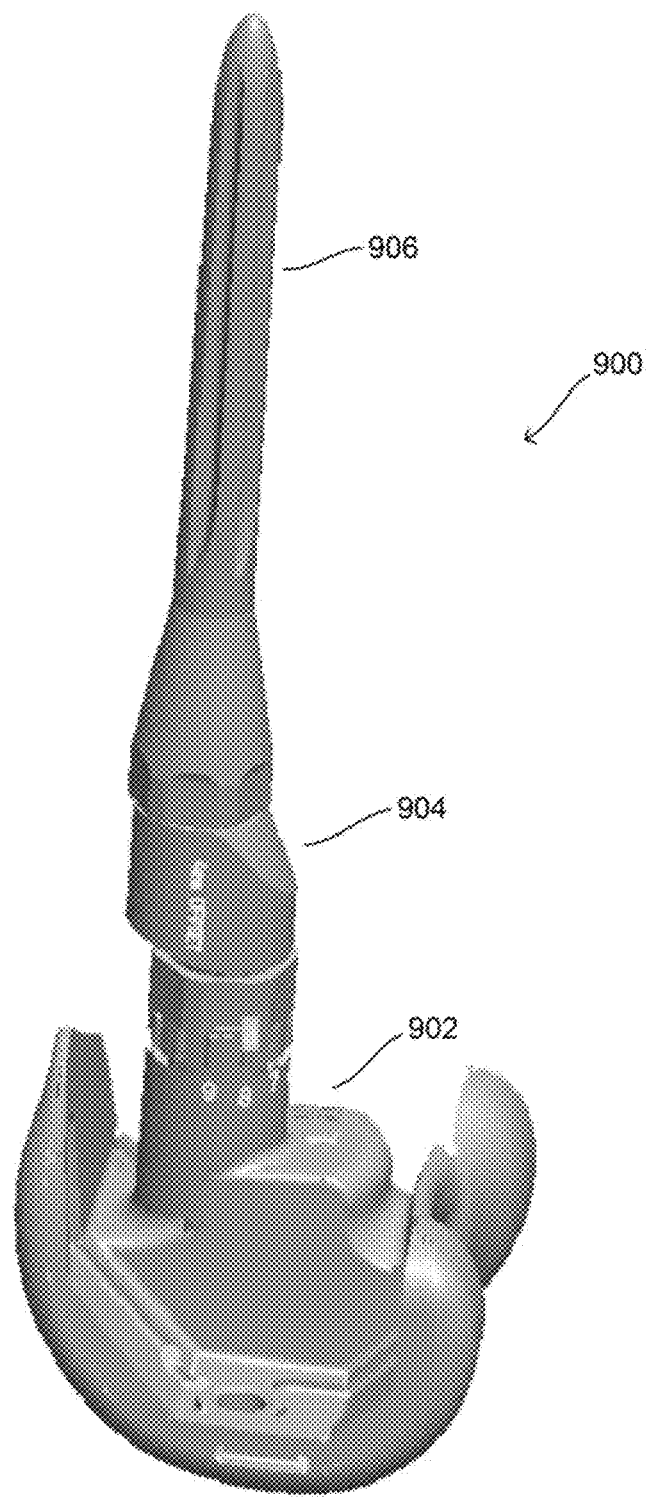
FIG. 9A shows an assembled perspective view of a femoral implant in an unlocked position.
Figure 9B:
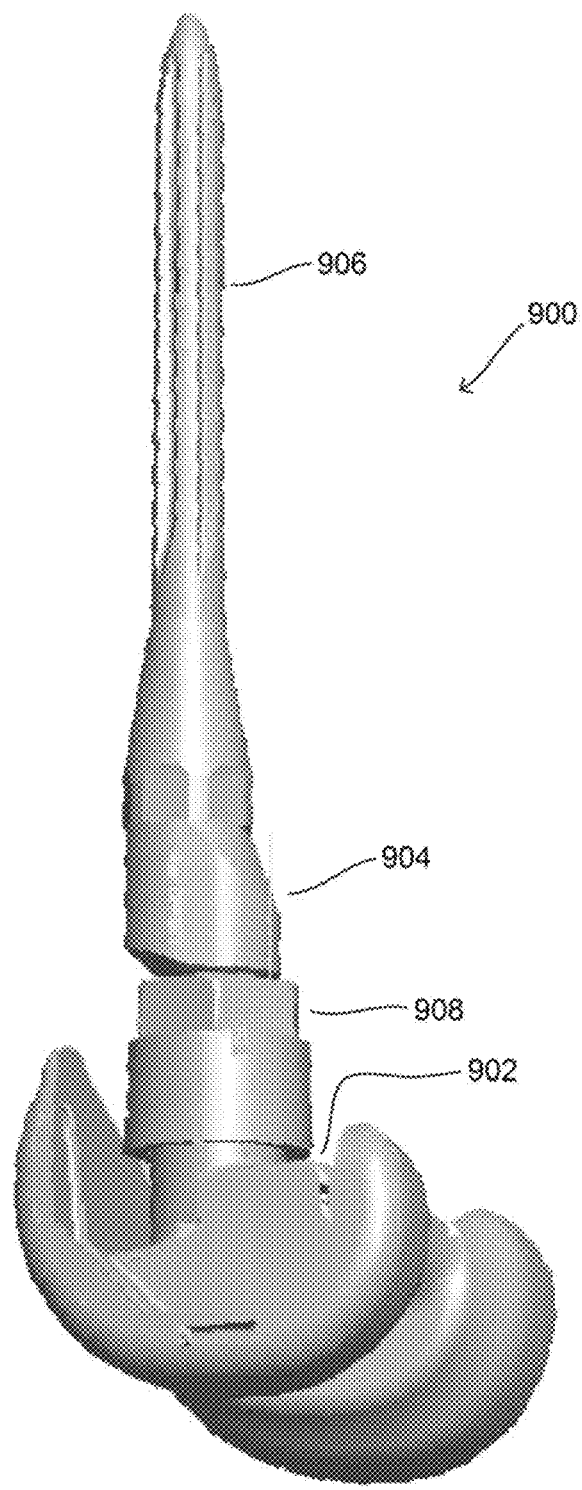
FIG. 9B shows an assembled perspective view of a femoral implant in a locked position.
Figure 9C:
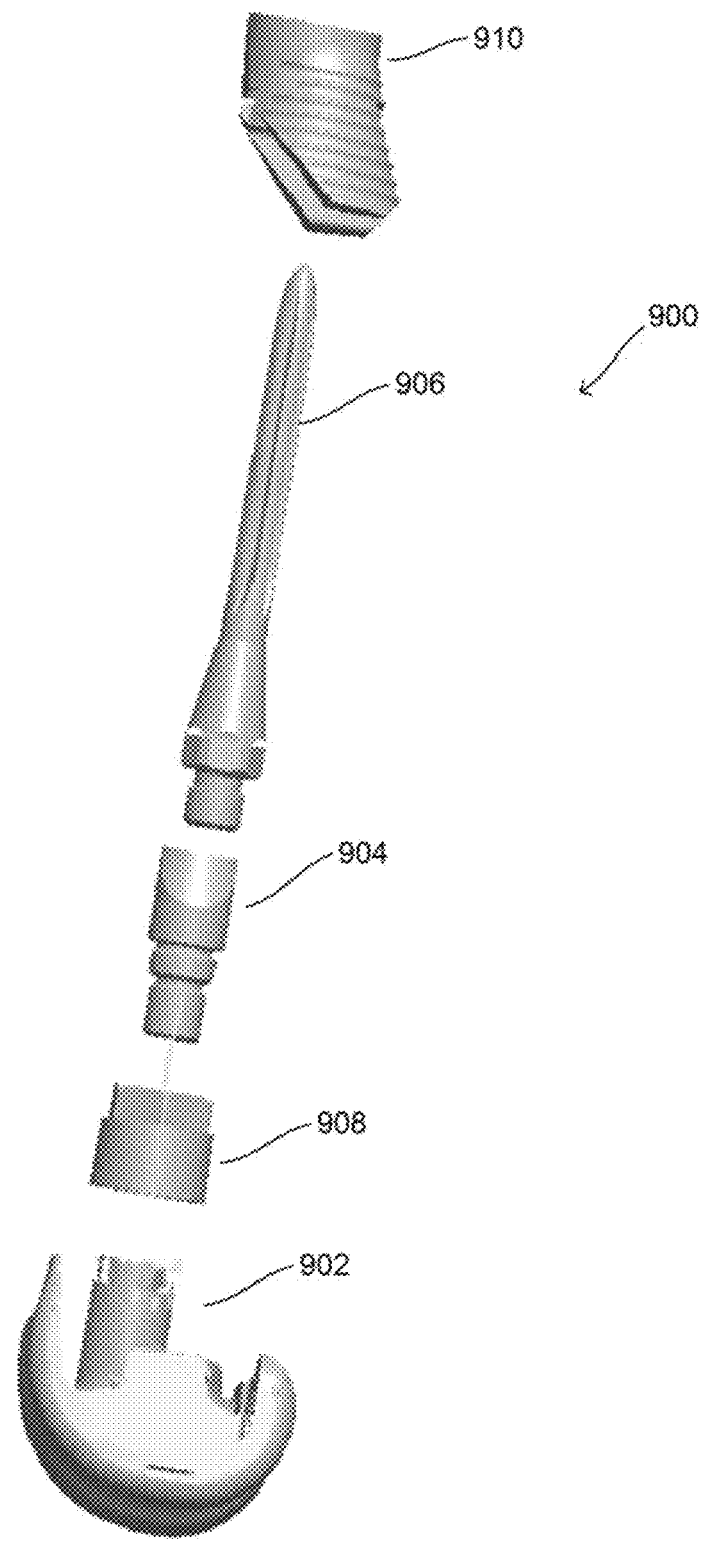
FIG. 9C shows an exploded perspective view of a femoral component, void adapter, offset component, stem, and MRD.
Figure 9D:
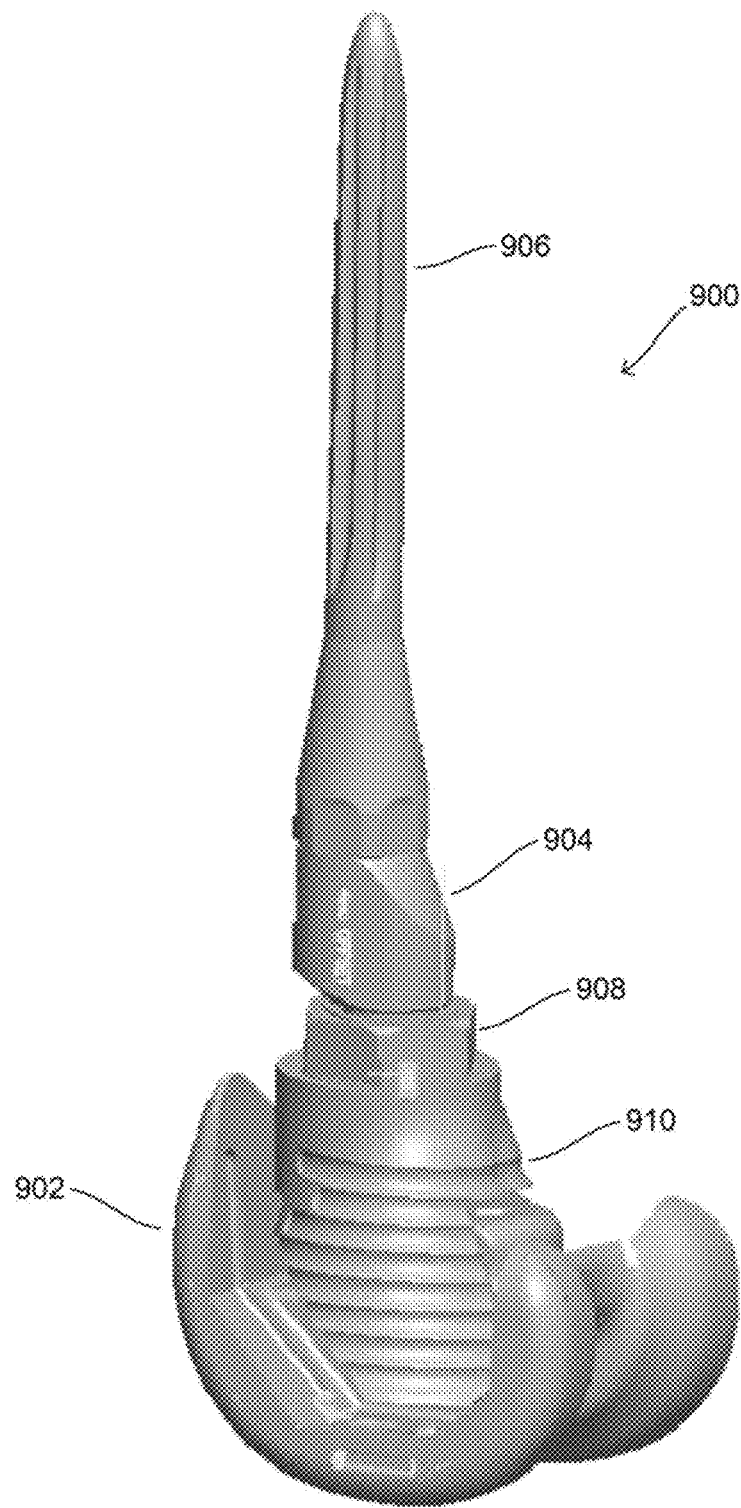
FIG. 9D shows an assembled perspective view of a locked femoral implant with an MRD locked into place.
Figure 9E:
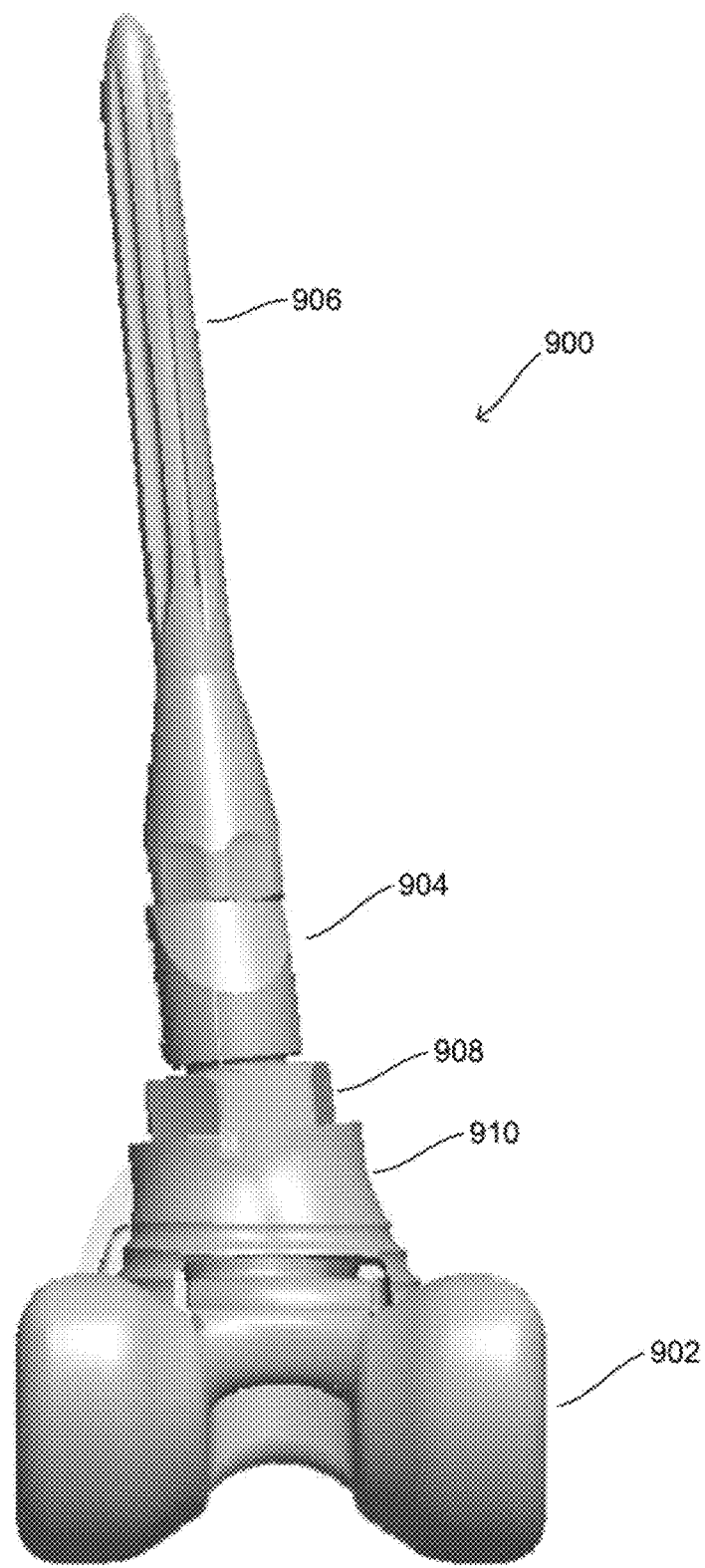
FIG. 9E shows an assembled front view of the locked femoral implant and MRD shown in FIG. 9D.

Referring now to FIGS. 9A-E, different embodiments of a femoral construct 900 are shown. FIG. 9A shows a perspective view of femoral construct 900 of the unlocked variety. The femoral construct 900 generally includes a femoral component 902, offset component 904, and stem 906. An embodiment of a femoral construct 900 of the locked variety is shown in FIG. 9B. In this embodiment, the femoral construct 900 further includes a void adapter 908. Both locked and unlocked femoral constructs 900 are capable of accepting the same MRD, such as MRD 910, for example. In such circumstance, the locked femoral construct 900 is adapted to mechanically lock the MRD 910 to a femoral implant prior to implantation. On the other hand, where the unlocked femoral construct would be used in conjunction with the MRD 910, the MRD would typically be implanted into the corresponding bone cavity prior to implantation of the femoral implant, and would be optionally joined together by use of adhesive, rather than being mechanically locked. An assembled locked femoral construct 900 is shown in FIG. 9D with the MRD 910 attached.

As best seen in the exploded view of a locked femoral construct 900 in FIG. 9C, the void adapter 908 can include an external hexagon feature for accepting a wrench for locking the final position of the offset component 904. The distal end of void adapter 908 can also include a male taper with an outer diameter greater than the distance between two diametrically opposed vertices of the hexagon shape. This allows a female taper of the MRD 910 to pass over the external hexagon feature of the void adapter 908 during assembly. Further, the void adapter 908 can include a left hand thread on the axis to male taper sized to accept a thread of the offset component 904 to act as a locking nut.

Figure 9F:
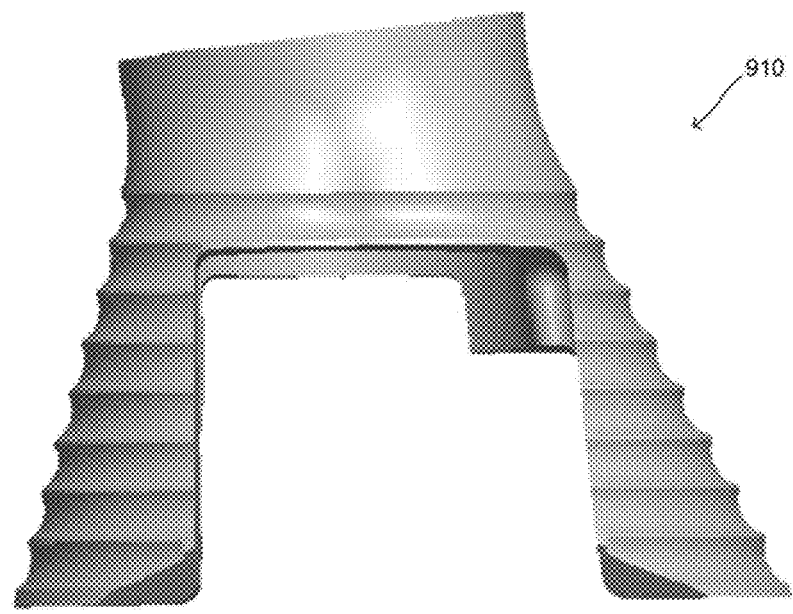
FIG. 9F shows a front view of one embodiment of a femoral MRD.

While the femoral construct of the locked variety can include a MRD mechanically locked to a femoral implant with the use of a taper lock feature (best seen in FIG. 9B), the femoral construct of the unlocked variety can be assembled with the use of bone cement at the time of implantation, for example. Both locked and unlocked femoral constructs can use the same MRD. The locked MRD can be assembled to the femoral component 902 before implantation. The unlocked MRD can be implanted before assembly of the femoral component 902. As seen in FIG. 9F, the MRD 910 can include a unique surface cross-section that provides improved load distribution to bone.

In a further embodiment of the invention, a first group of drilling steps can be performed to create a first cylindrical void space generally coaxial with the IM canal. Following this first group of steps, a femoral implant with a diaphyseal femoral cone 1100 (discussed below), that is generally frustoconical, can be implanted into the patient along the bone cavity created in the first group of steps. Alternatively, if the surgeon or other medical professional decides a femoral implant with a metaphyseal femoral cone is more appropriate, a second group of steps may be performed, building on the first group of steps, to create an appropriate bone cavity.

Figure 11:
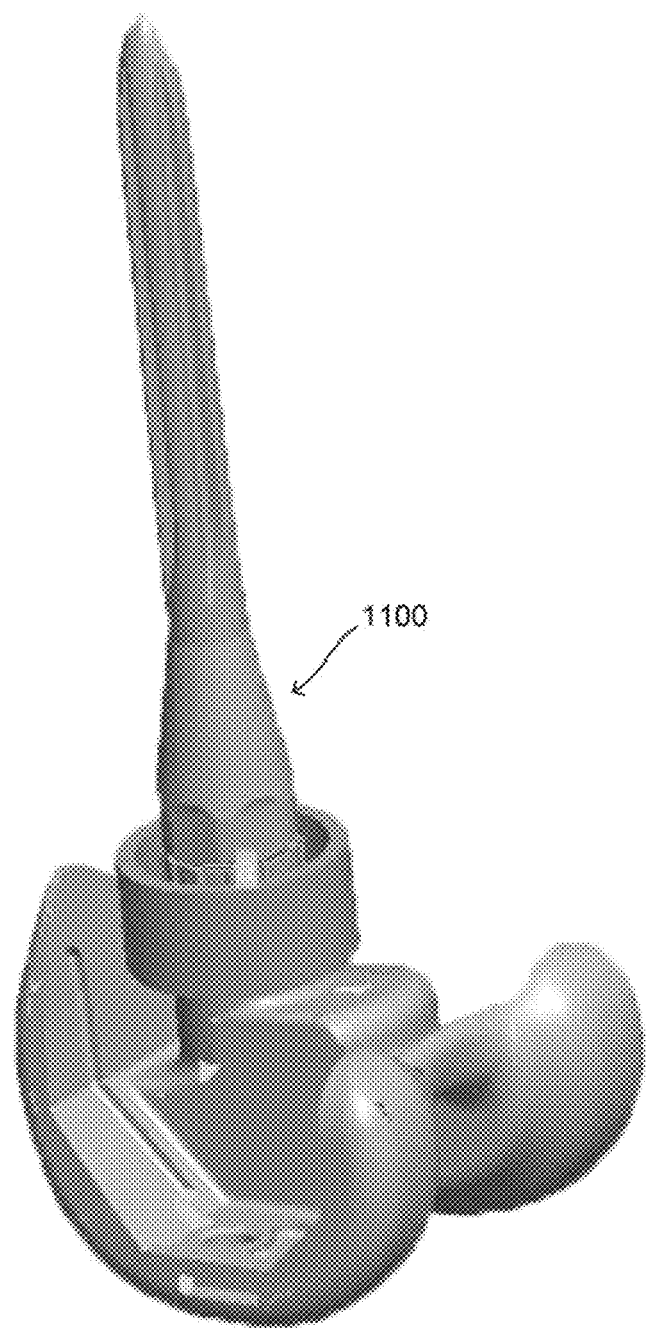
FIG. 11 shows a perspective view of one embodiment of a diaphyseal femoral cone.
Figure 12A:
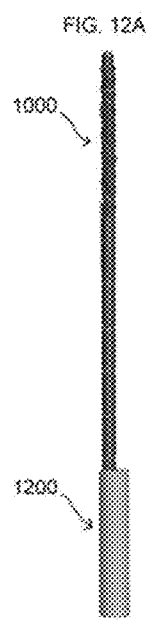
FIGS. 12A-B show front and perspective views of an offset bushing attached to the IM reamer of FIG. 10A.
Figure 12B:
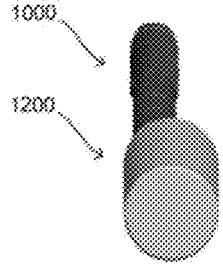
Figure 12C:
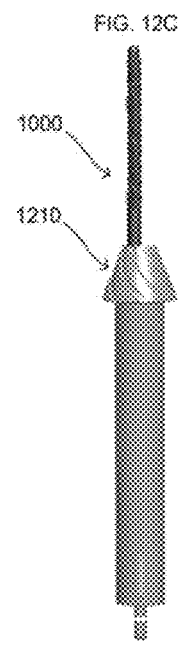
FIGS. 12C-D show front and perspective views of a conical reamer attached to the instrument of FIGS. 12A-B.
Figure 12D:
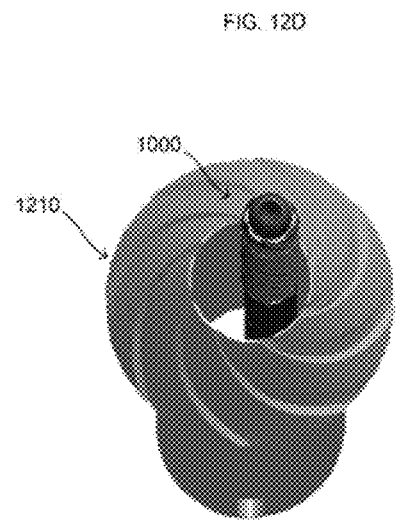

Referring now to FIGS. 10A-C, there are shown instruments used in the first group of steps described above. In a first step of a revision procedure, an IM reamer 1000 is used to create a first bone cavity generally along the axis of the IM canal. In a second step, a bushing 1010 is slipped over the IM reamer 1000 and used to ream a second bone cavity generally coaxial with the cavity from the first step. In a third step, a cylindrical reamer 1020 is slipped over the IM reamer 1000 and used to ream a third bone cavity generally coaxial to cavities from the first and second steps to prepare the bone to accept a diaphyseal femoral cone, such as diaphyseal femoral cone 1100 illustrated in FIG. 11. If it is decided at this point that a metaphyseal femoral cone is more appropriate, the diaphyseal femoral cone 1100 is not implanted and two further steps can be completed to prepare the bone to receive a metaphyseal femoral cone.

Figure 13:
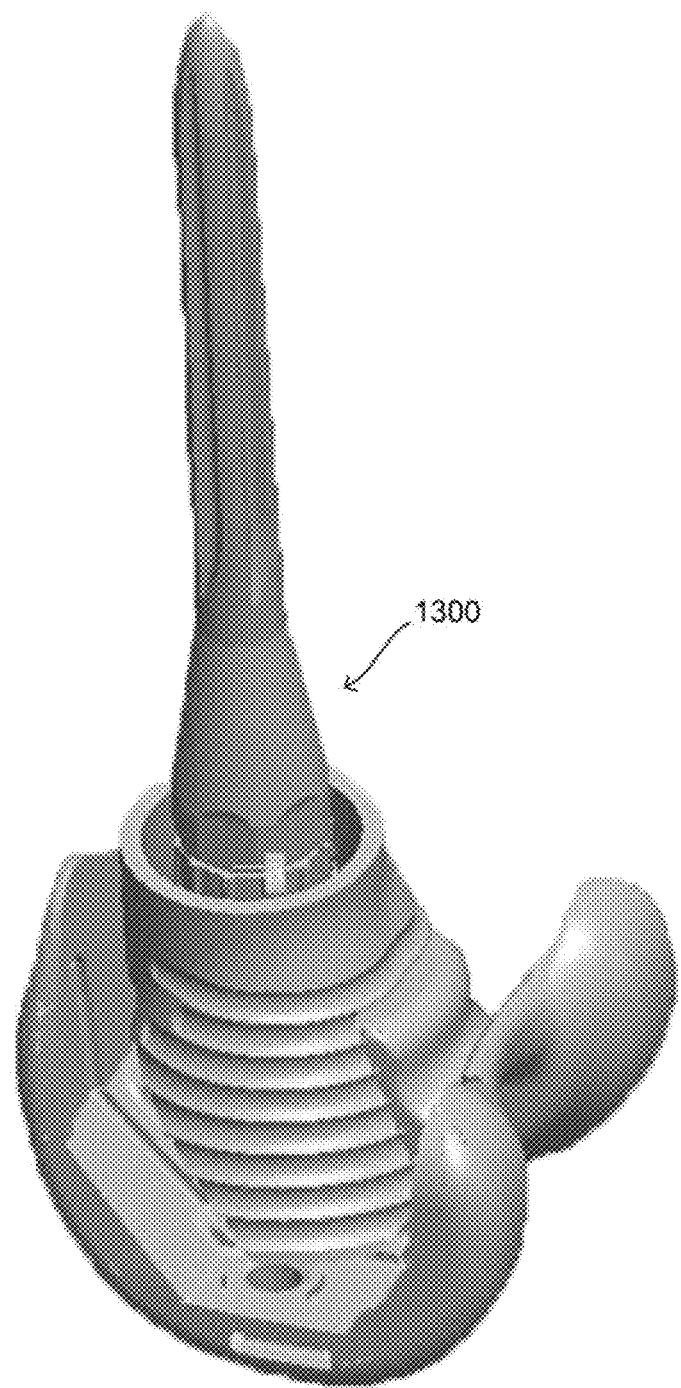
FIG. 13 shows a perspective view of one embodiment of a metaphyseal femoral cone.

Referring now to FIGS. 12A-D, there are shown instruments used in the second group of steps described above. In a fourth step of a revision procedure, illustrated in FIGS. 12A-B, an offset driver 1200 is slipped over IM reamer 1000. Following this, in a fifth step illustrated in FIGS. 12C-D, a conical reamer 1210 is slipped over offset driver 1200 (not visible in FIGS. 12C-D). The offset conical reamer 1210 can then be used to create conical bone cavities that have an axis offset from the bone cavities created in steps 1-3 described above. For example, a first conical bone cavity can be created medial to the bone cavity created in steps 1-3. After adjusting the offset driver 1200 to a different position, a second conical bone cavity can be created lateral to the bone cavity created in steps 1-3. The conical bone cavities can be created as necessary to form a complementary fit with a metaphyseal femoral cone, for example metaphyseal femoral cone 1300 illustrated in FIG. 13.

Figure 14:
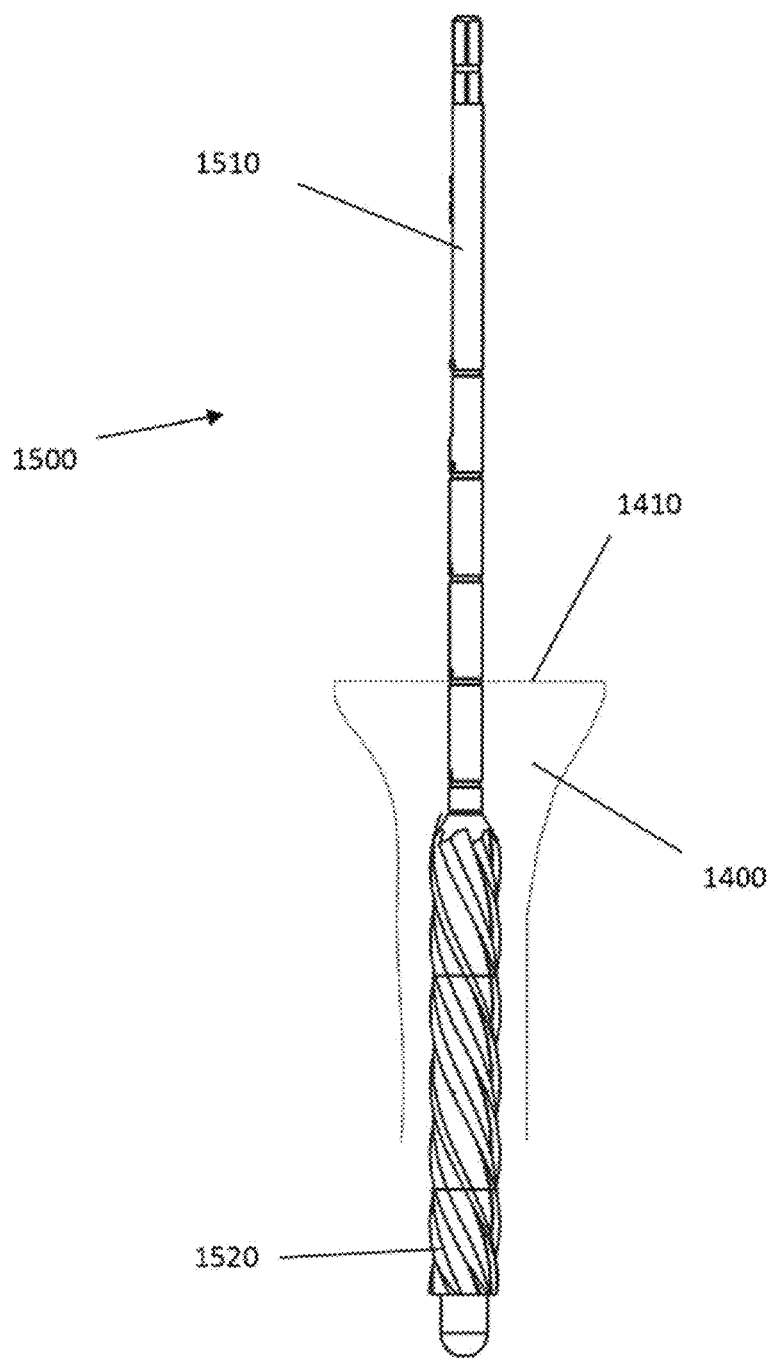
FIG. 14 shows a front view of a preparatory reaming step of a tibia bone.

FIGS. 14-24 show other embodiment systems and methods for forming voids in bone. Referring now to FIG. 14, the beginning of one method of a revision procedure is shown. For example, in a revision procedure of a total knee replacement surgery, the initial step is to first ream the bone 1400 along the IM canal. Although an elongate IM reamer 1500 is illustrated as distally reaming the tibia beginning at the tibial plateau 1410, this is merely an example. The elongate IM reamer 1500 could also be used to proximally ream the femur beginning at the distal end of the femur in substantially the same manner. FIG. 14 shows the elongate IM reamer 1500 following the initial reaming step. The elongate IM reamer 1500 includes an elongate IM reamer head 1520, which is shown positioned within the IM canal, and an elongate reamer shaft 1510, which is shown extending from the IM canal. The elongate IM reamer head 1520 is used for reaming the IM canal and for firmly positioning the elongate IM reamer 1500 within bone 1400 to provide a stable platform for the elongate reamer shaft 1510 to accommodate further components in the knee revision procedure.

Figure 15:
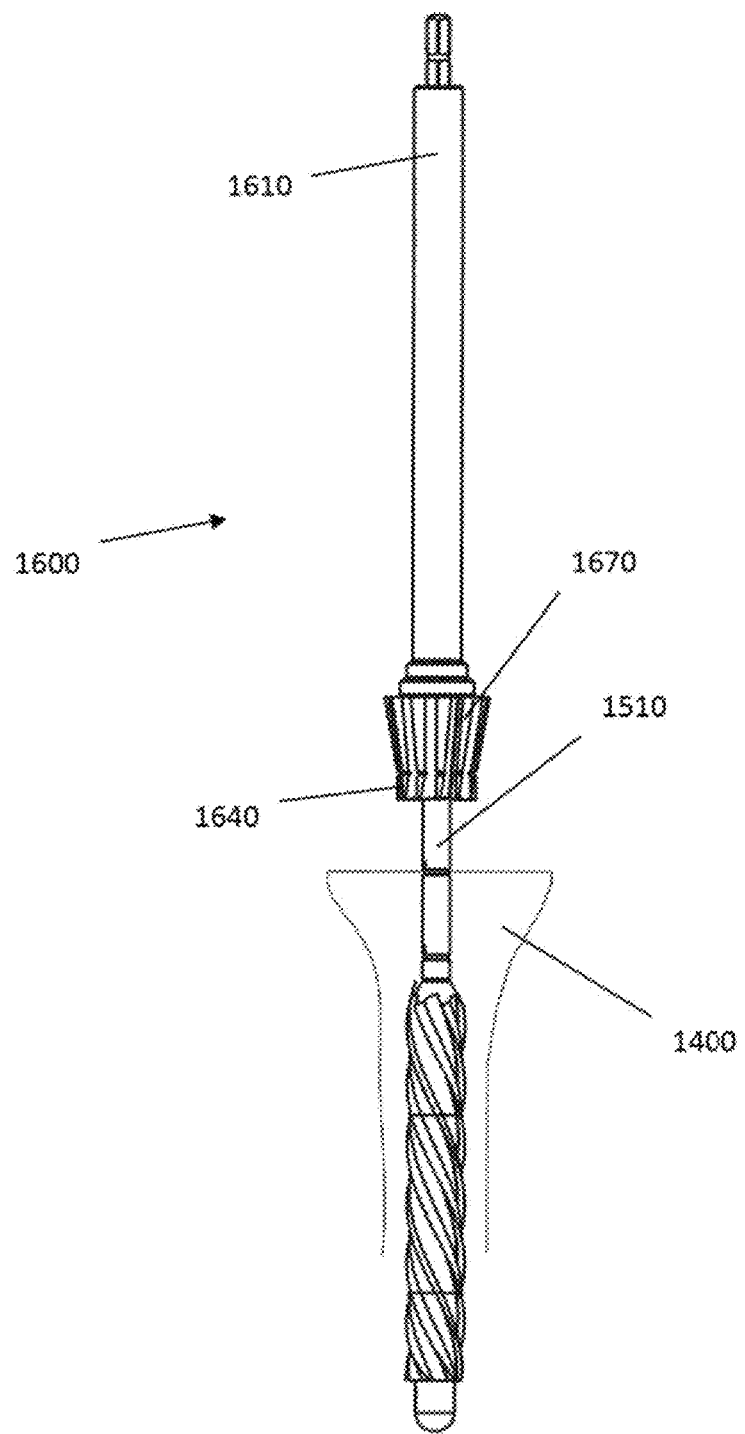
FIG. 15 shows a front view of a cone reamer being prepared for a first reaming step.

FIG. 15 shows the first step following the initial tibial or femoral IM canal preparation. The elongate IM reamer 1500 utilized to initially prepare the IM canal is left in place within the bone 1400 in order to support additional equipment utilized for forming bone voids. As shown in FIG. 15, a hollow inner cylinder of a cone reamer 1600 is slipped over the elongate IM reamer shaft 1510 to position a cone reamer head 1620 coaxial with the elongate IM reamer 1500. The cone reamer head 1620 is generally frustoconical, but may incorporate additional features to accommodate the shape of a void filling implant. For example, a neck 1640 may extend from the distal end of the cone reamer head 1620 in order to form a similarly shaped void. The cone reamer 1600 also includes a cone reamer shaft 1610. The cone reamer shaft 1610 is configured to be mechanically or manually driven. For example, the proximal end of the cone reamer shaft 1610 may be configured to be inserted into a drill chuck.

Figure 16:
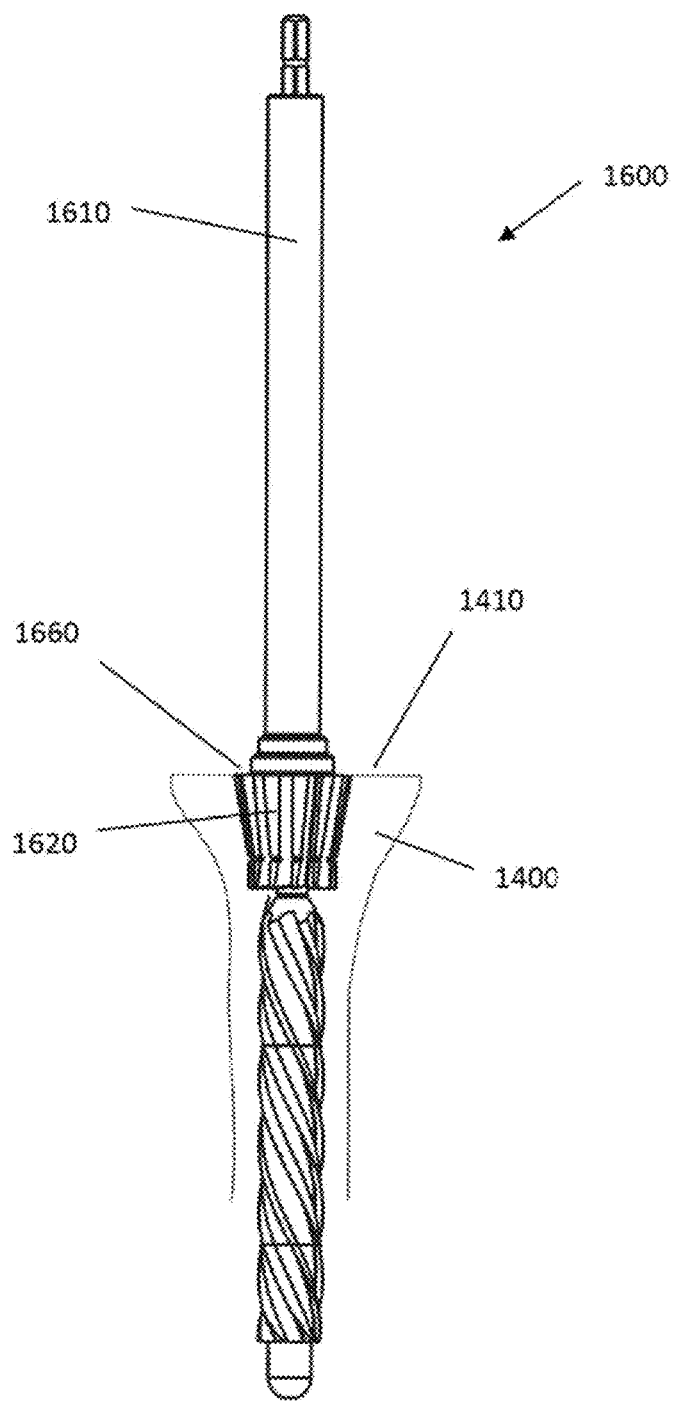
FIG. 16 shows a front view of a first reaming step using the cone reamer of FIG. 15.

Once the cone reamer 1600 is placed over the elongate IM reamer shaft 1510, a first reaming step is performed by mechanically or manually applying a torque to the cone reamer 1600 to drive the cone reamer head 1620 distally along the elongate IM reamer shaft to form a central bone void that is generally coaxial with the prepared IM canal. FIG. 16 shows the positioning of the cone reamer head 1620 within the bone 1400 following the first reaming step. As show in FIG. 16, the cone reamer head 1620 is driven into the bone such that the proximal surface 1660 of the cone reamer head 1620 is flush with the tibial platform 1410. In another embodiment, the surgeon may choose to drive the cone reamer head 1620 deeper into the bone 1400 so that the proximal surface of the cone reamer head 1660 is distal to the tibial platform 1410. This may occur where a surgeon utilizes a tibial or femoral augment to accommodate a medial or lateral bone defect. In such a scenario the surgeon may drive the cone reamer head 1620 deeper into the bone 1400 such that the proximal surface of the cone reamer head 1660 is flush with the proximal surface of an augmented bone segment (not shown), but distal to the tibial platform 1410.

Figure 17A:
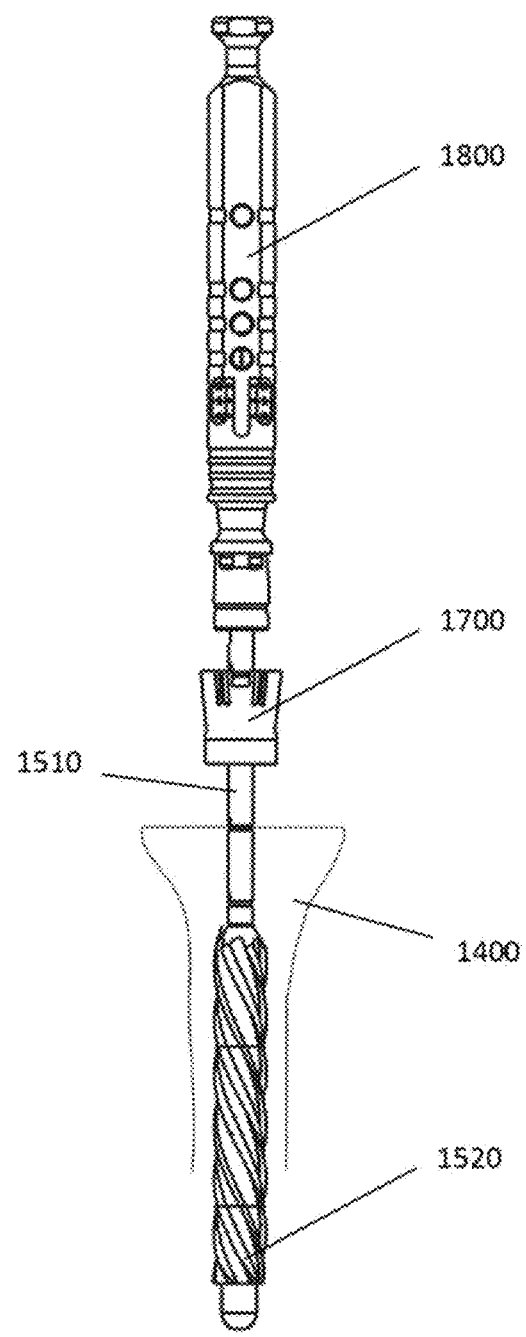
FIG. 17A shows a front view of a cone trial and reamer guide shaft being prepared for a placing step.

Referring now to FIG. 17A, the placement of a cone trial 1700 is shown. The cone reamer 1600 first is removed from the created bone void and from engagement with the elongate IM reamer 1500. With the elongate IM reamer remaining in place, a cone trial 1700 and a reamer guide shaft 1800 are then slidably engaged with the elongate IM reamer shaft 1510. For example, the cone trial 1700 and reamer guide shaft 1800 may have a hollow inner cylinder that is placed over the elongate IM reamer shaft 1510 in a slidable arrangement.

Figure 17B:
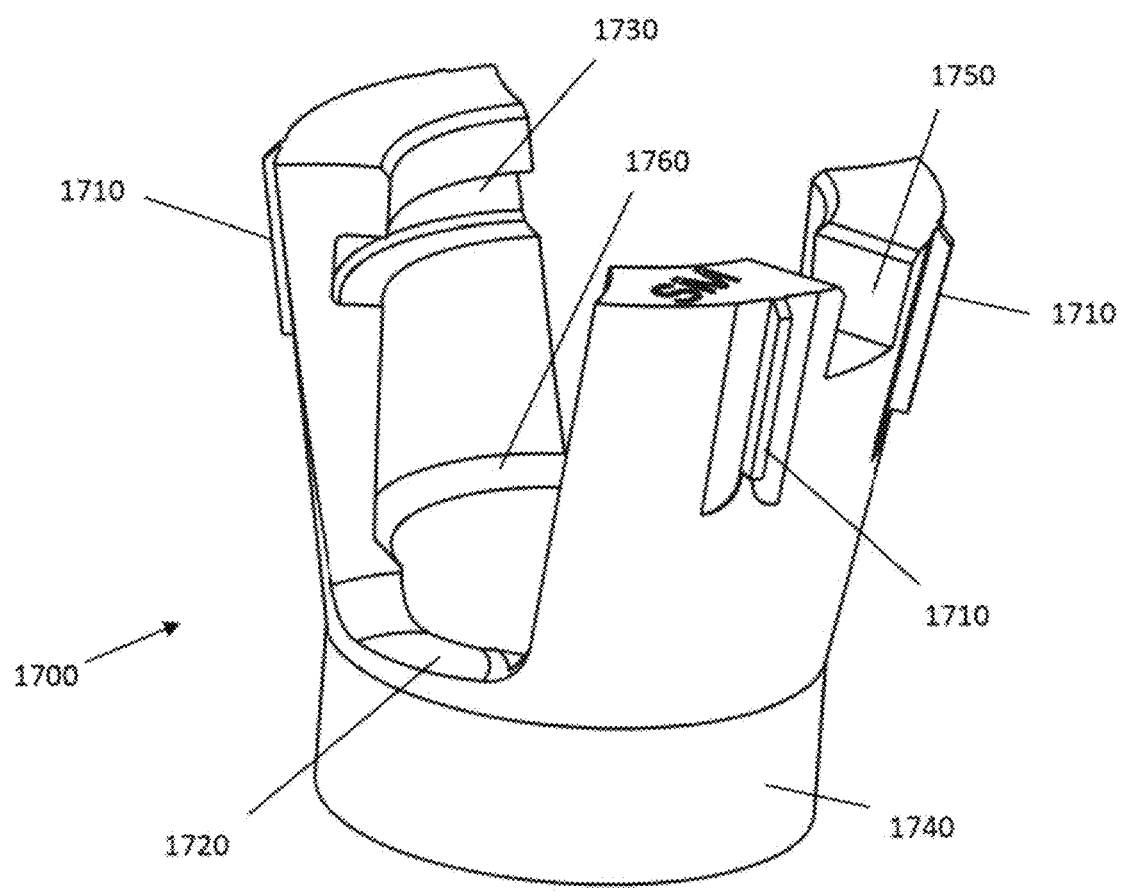
FIG. 17B shows a perspective view of the cone trial.
Figure 17C:
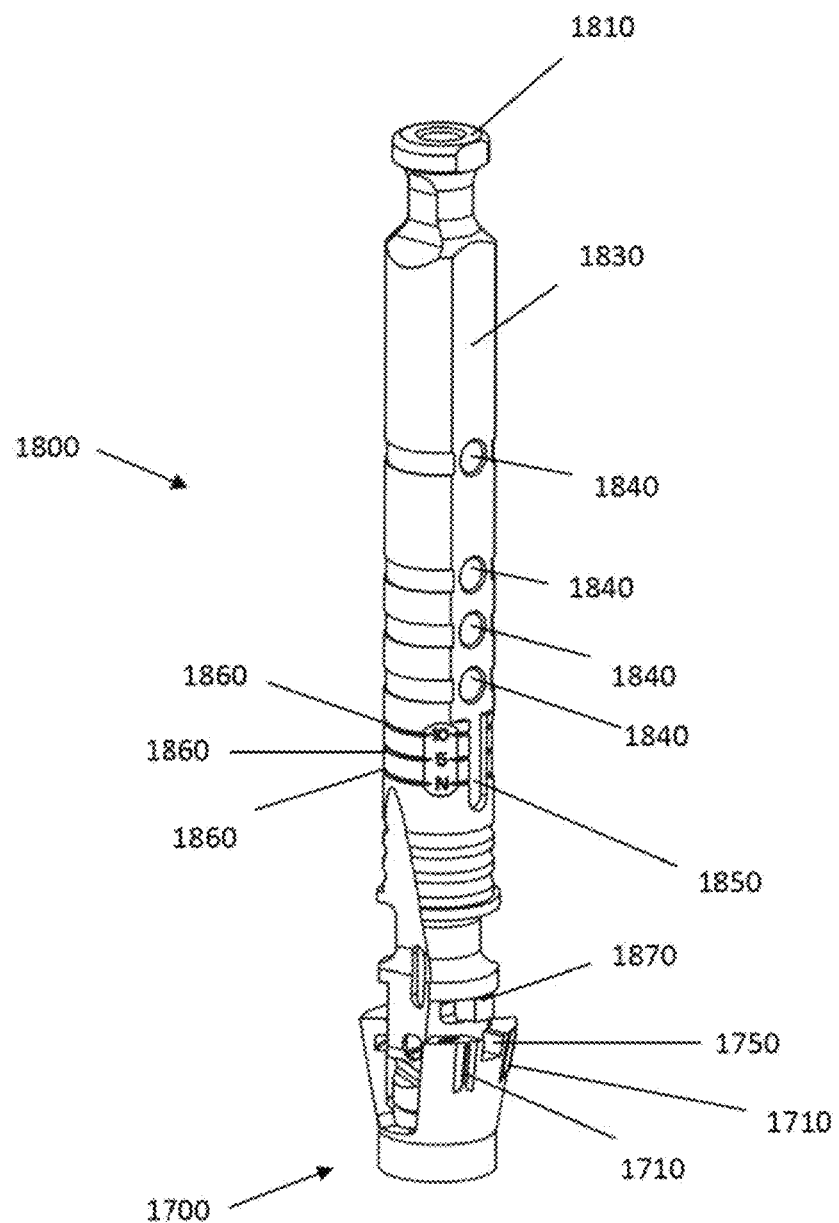
FIG. 17C shows a perspective view demonstrating an interrelation between the cone trial and reamer guide shaft.

FIGS. 17B-C show a perspective view of the cone trial 1700 and the reamer guide shaft 1800, respectively. The cone trial 1700 is generally frustoconical in shape and includes an extraction feature 1730, anti-rotation splines 1710, at least one clearance groove 1720, and a keyway slot 1750. The cone trial 1700 may include other geometric features to substantially match the central bone void. For example, the cone trial 1700 may include a cone trial neck 1740 extending from the distal end of the cone trial 1700. The extraction feature 1730 appears as a groove formed on the inner surface of the cone trial, which creates a ridge for engagement with an extraction device. One example of such extraction device is the reamer guide shaft 1800. While this particular embodiment shows a groove forming the extraction feature 1730, other features not shown may be implemented that allow for the transmission of an axial force to the trial cone 1700 in order to forcibly remove the trial cone 1700 from the central bone void.

FIG. 17C shows a close-up view of the interrelation between the reamer guide shaft 1800 and cone trial 1700. The reamer guide shaft generally includes a reamer guide shaft body 1830, a reamer guide shaft impaction surface 1810, a plurality of locking features 1840, an orientation key 1870, and a depth indicator 1860. The impaction surface 1810 is located at the proximal end of the reamer guide shaft body 1830 and is configured to receive and evenly transmit impact forces in an axial direction toward the cone trial 1700. The plurality of locking features 1840 are shown as circular indents located on the outer surface of the reamer guide shaft body 1830 and axially aligned along the longitudinal axis of the reamer guide shaft 1800. Also, located on the outer surface of the reamer guide shaft body is the depth indicator 1860, which is shown as a series of notches etched in the outer surface of the reamer guide shaft body 1830 along with corresponding indicator markings. A retaining groove 1850 is shown intersecting the depth indicator in a proximal-distal direction.

Near the distal end of the reamer guide shaft is the orientation key 1870, which appears as a protrusion extending radially from reamer guide shaft body 1830. The orientation key 1870 is shaped to tightly fit into the orientation keyway slot 1720 of cone trial 1700 to prevent the rotation of the reamer guide shaft 1800 and cone trial 1700 with respect to each other. The distal end of the reamer guide shaft 1800 is configured to partially fit within the cone trial 1700 and to mate with an internal ridge 1760 located therein. As shown, the diameter of the internal ridge 1760 is narrower than the outside diameter of the reamer guide 1800, which facilitates a mating engagement in order to evenly transfer impact forces from the impaction surface 1820 to the cone trial 1700.

Figure 18A:
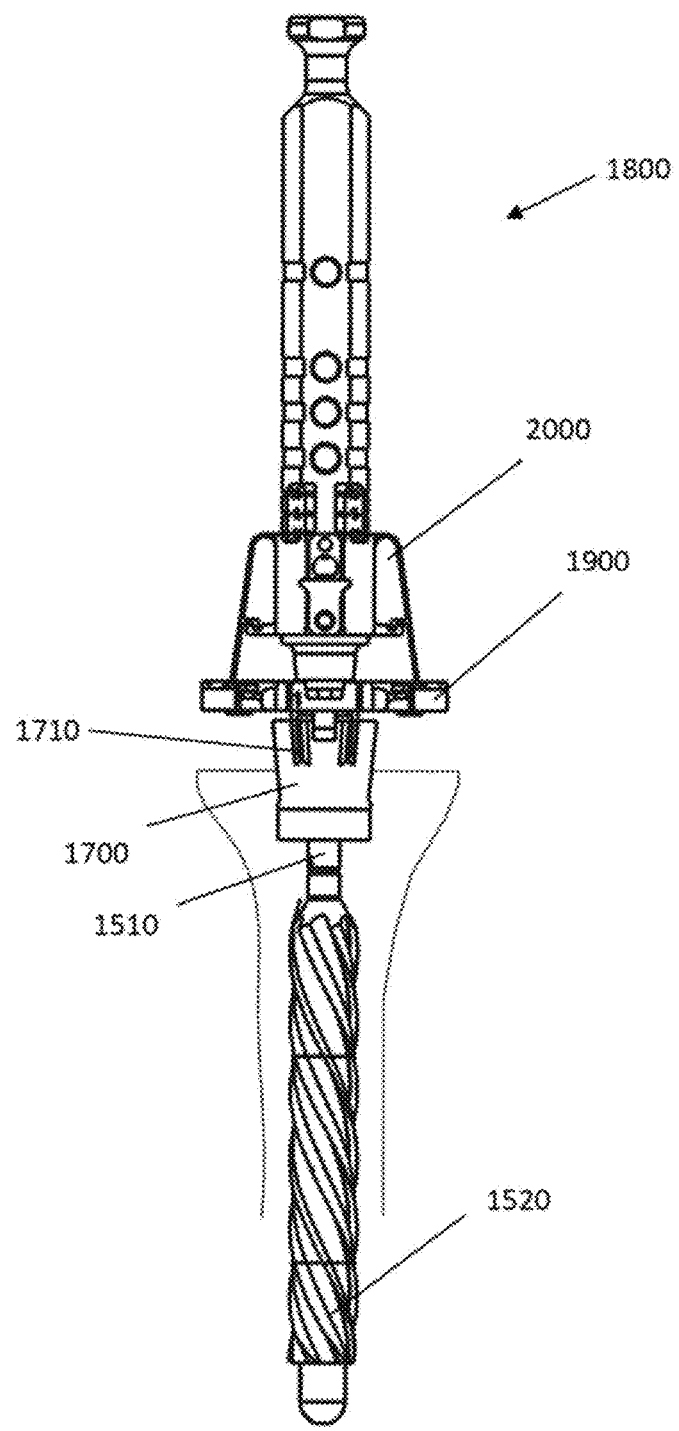
FIG. 18A shows a front view of a placing step and a template guide and sizing template being prepared for a first seating step.

FIG. 18A shows an inserting step and preparation for a seating step. Once the reamer guide shaft 1800 and cone trial 1700 are placed over the elongate IM reamer 1500, the cone trial 1700 is then partially inserted within the central bone void using the reamer guide shaft 1800 such that the anti-rotation splines 1710 remain proximal of the tibial platform 1410. A template guide 2000 and sizing template 1900 are then placed over the reamer guide shaft 1800.

Figure 18B:
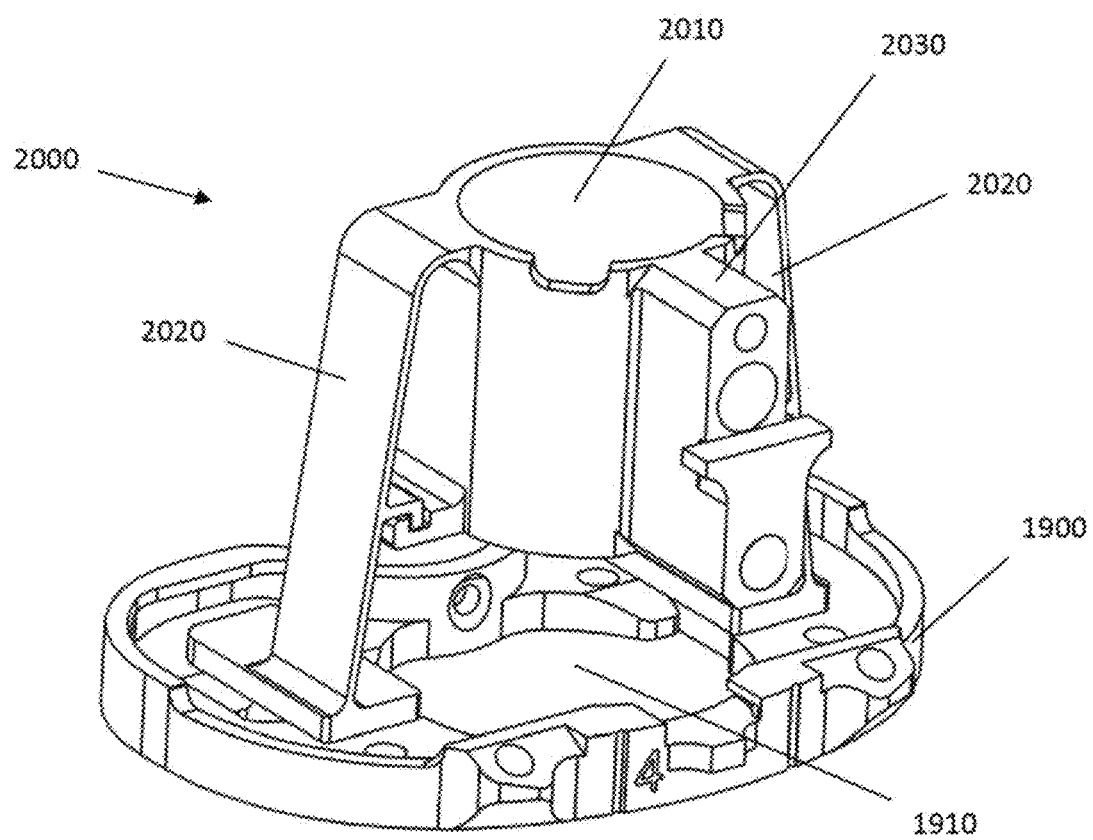
FIG. 18B shows a perspective view of the sizing template and template guide of FIG. 18A.

FIG. 18B shows a perspective view of the template guide 2000 and sizing template 1900. The template guide 2000 includes support arms 2020 that selectively attach to the sizing template 1900. The sizing template 1900 has a cavity 1910 that is coaxial with a template guide cavity 2010. The template guide 2000 facilitates manipulation of the sizing template 1900 by the surgeon and also connects the sizing template 1900 to the reamer guide shaft 1800 to prevent rotation of the sizing template 1900 with respect to the reamer guide shaft 1800.

Figure 19:
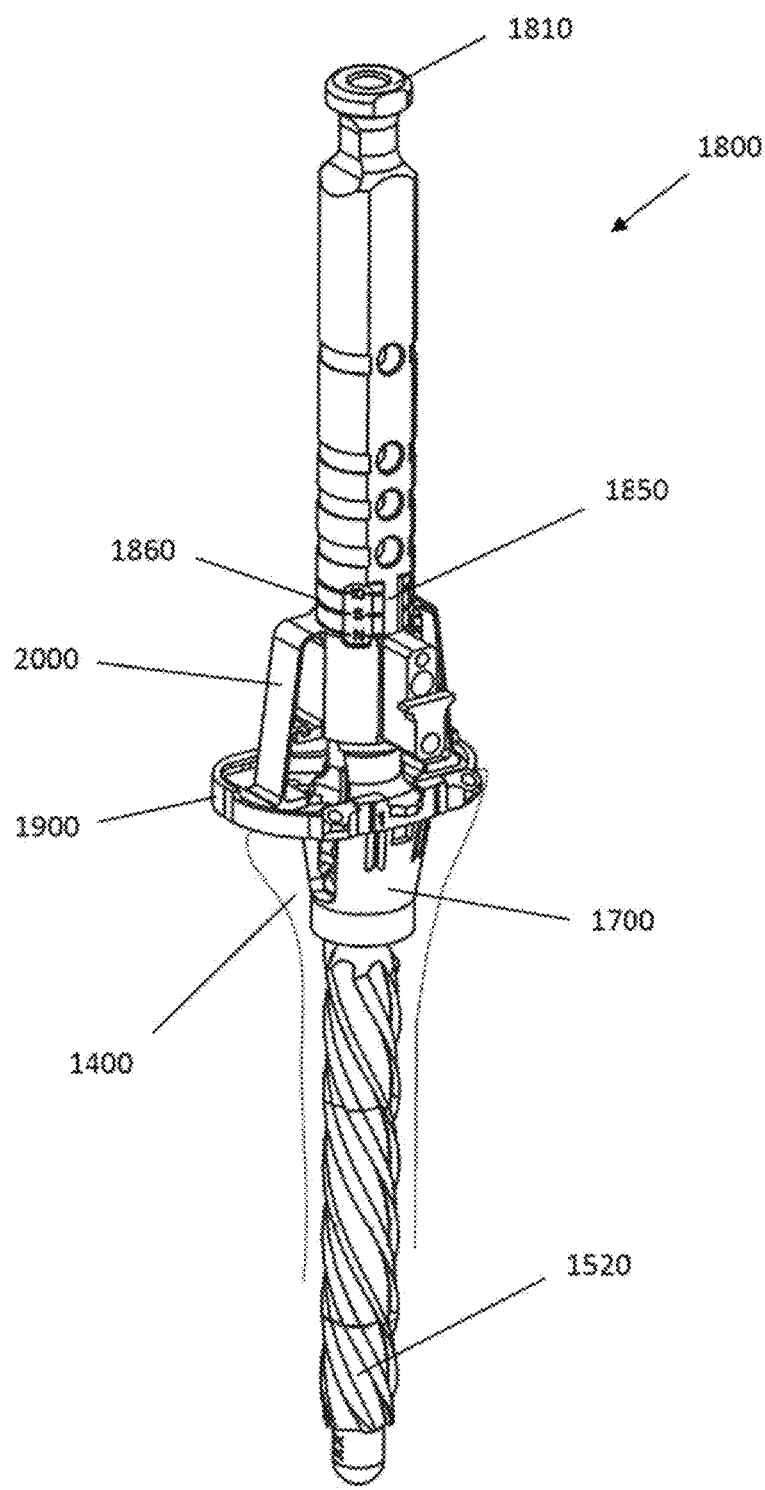
FIG. 19 shows a perspective view of the cone trial, template guide, sizing template, reamer guide shaft and bone after the first seating step has been completed.

Referring now to FIG. 19, a perspective view of a seating step is shown. As the sizing template 1900 and template guide 2000 are placed over the reamer guide shaft 1800, an engagement feature on the inner surface of the template guide cavity 2010 engages the retaining groove 1850 of the reamer guide shaft 1800. The engagement feature then comes to rest against the distal edge of the retaining groove 1850. At this point, the sizing template 1900 and template guide 2000 are restrained from distal and rotational movement, but are free to move along the retaining groove 1850 proximally. After sizing and setting the proper rotation, the cone trial 1700 is fully seated by applying impact force on the impact surface 1810. This causes the anti-rotation splines 1710 to engage the bone, thereby preventing rotational movement of the cone trial 1700 with respect to the bone 1400. The appropriate driving depth of the trial cone 1700 is determined by viewing a proximal plateau 2030 of the template guide 2000 in relation to the depth indicator 1860 of the reamer guide shaft 1800. As the trial cone 1700 is driven deeper into the bone 1400, the tibial platform 1410 will engage and push the sizing template 1900 and template guide 2000 proximally along the retaining groove 1850. When the proximal plateau 2030 lines up with the depth appropriate markings, the surgeon knows the proper depth has been reached. For example, the reamer guide shaft 1800 may provide three depths based upon whether a tibial augment is used and the size of the augment. Where no augment is utilized, the cone trial 1700 is driven into the bone 1400 such that the proximal surface of the cone trial 1700 is either flush with the tibial platform 1410 or approximately 1-3 mm distal of the tibial platform, which in this example would be where the proximal plateau 2030 would line up with the most distal marking of the depth indicator 1860, which is designated as "N". Once the cone trial 1700 is fully seated within the bone 1400, the template guide 2000 and sizing template 1900 are removed so that the reamer guide shaft 1800 can be prepared for a second reaming step.

Figure 20A:
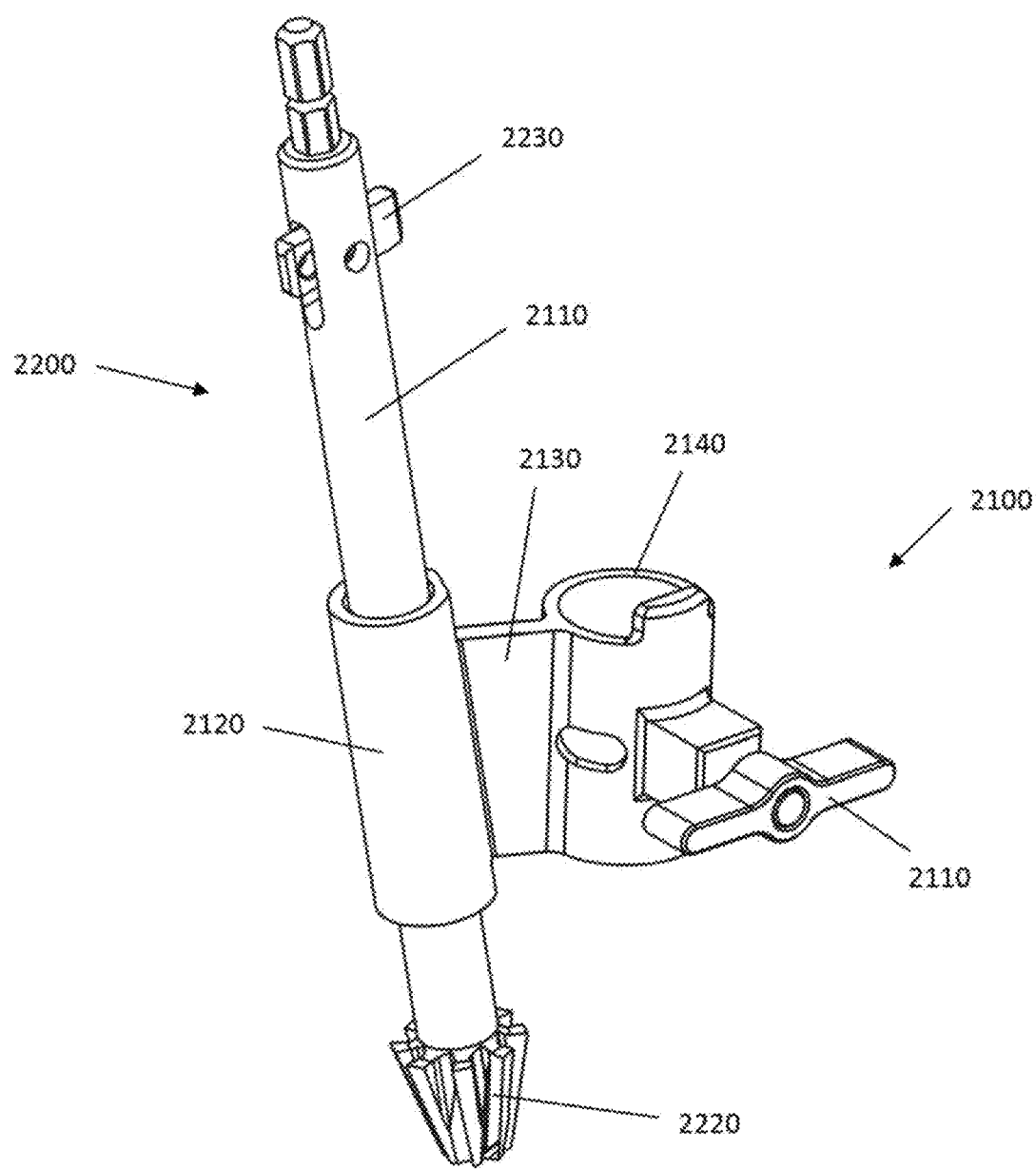
FIG. 20A shows a perspective view of an offset lobe reamer retainer and offset lobe reamer being prepared for a second reaming step.
Figure 20B:
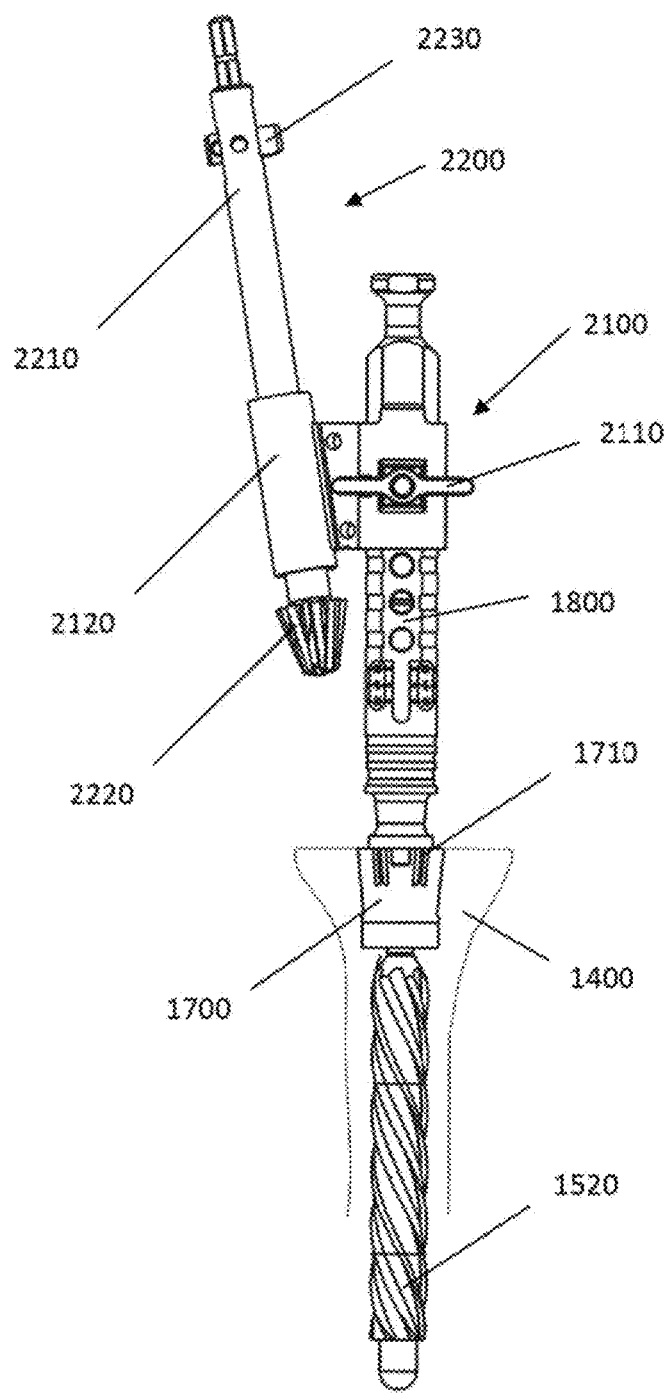
FIG. 20B shows a front view of further preparation of the offset lobe reamer and lobe reamer guide for a second reaming step.

FIGS. 20A-B illustrate an offset lobe reamer 2200 and offset lobe reamer retainer 2100 and their preparation for the second reaming step to form a first offset lobe void adjacent to the central bone void. Referring now to FIG. 20A, the offset lobe reamer retainer 2100 includes an offset lobe reamer retainer body 2140 that may be cylindrically hollow, an offset lobe reamer guide 2120 attached to the offset lobe reamer body 2140 by a flange 2130, and a locking mechanism 2110. The offset lobe reamer guide 2120 has a longitudinal axis that offset from the axis of the IM canal. The offset lobe reamer 2200 includes an offset lobe reamer shaft 2210, an offset lobe reamer head 2220 located at the distal end of the offset lobe reamer shaft 2210, and a depth stop 2230 near the proximal end of the lobe reamer shaft 2210. The proximal end of the offset lobe reamer 2200 is configured to be manually or mechanically operated. The offset lobe reamer 2200 is initially prepared by slidably engaging the offset lobe reamer shaft 2210 with the offset lobe reamer guide 2120.

Referring to FIG. 20B, the offset lobe reamer retainer body 2140 is then placed over the reamer guide shaft 1800 such that the offset lobe reamer head 2220 faces the bone 1400. The offset lobe reamer retainer 2100 is then locked at the proper location, which correspondingly fixes the longitudinal axis of the lobe reamer guide 2120 with respect to the longitudinal axis of the IM canal. An example of the locking mechanism 2110 is a wingnut that provides a locked connection to the reamer guide shaft 1800, whereby the threaded screw portion of the locking wingnut engages the circular indents of the locking features 1840. The proper location is determined by selecting a locking position corresponding to a predetermined locking feature 1840 of the reamer guide shaft 1800. The particular embodiment shown in FIGS. 17C and 20A illustrate four separate locking features 1840, each corresponding to the desired size of the first offset lobe void. For instance, the locking features 1840 may be designated small, medium, large, and extra-large with the most proximal locking component 1840 being small and most distal being extra-large. The more distal the offset lobe reamer retainer 2100 is locked, the further the axis of the first offset lobe void will be from the axis of the central bone void. It is also possible to vary the size of the flange 2130, rather than the locking position to achieve similar results.

Figure 21:
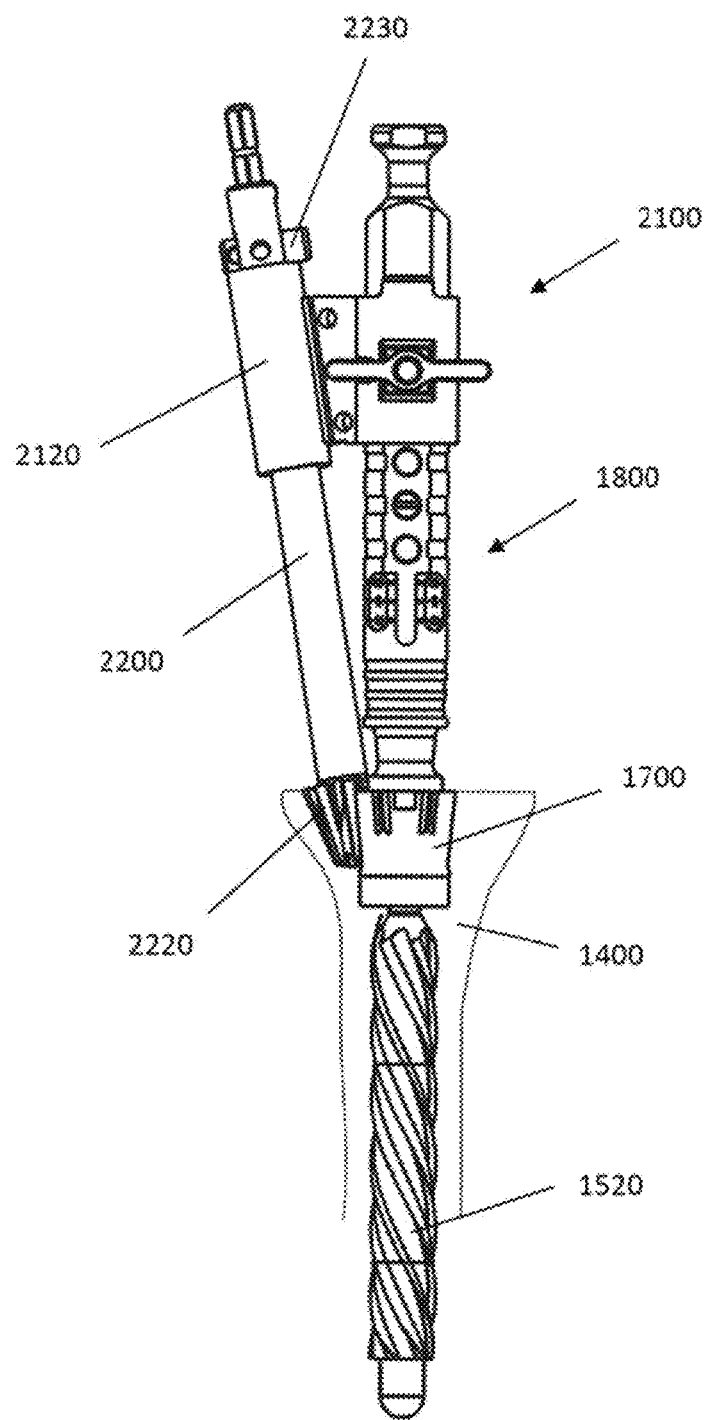
FIG. 21 shows a front view of the surgical reaming system and tibia bone after the second reaming step.

FIG. 21 shows the completion of a second reaming step. Once the offset lobe reamer retainer 2100 is locked in the proper position, the surgeon can drive, either mechanically or manually, the offset lobe reamer head 2220 into the bone 1400, thereby reaming the first offset lobe void adjacent to the central bone void. The proper depth of the first offset lobe void can be achieved when the depth stop 2230 abuts the proximal edge of the offset reamer guide 2120, thereby preventing further distal reaming. The first offset lobe void that is formed by the particular embodiment shown in FIG. 21 is integrated with the central bone void to provide the appearance of one continuous void. This is achieved by the clearance grooves 1720 of the cone trial 1700. This feature provides clearance so that the offset lobe reamer head 2220 is able to breach the wall of bone formed by the central bone void in order to integrate the voids. Once the first offset bone void is formed, a second offset bone void may be created by repeating the second reaming step on the opposite side of the central bone void. Such first and/or second offset bone void may be desirable where there is a bone deformity adjacent to the central bone void. Reaming offset lobe voids would remove the deformity and leave a precisely formed void to be filled with a bone void filler, such as a cone (discussed below), to provide structural integrity to the bone 1400.

Figure 22A:
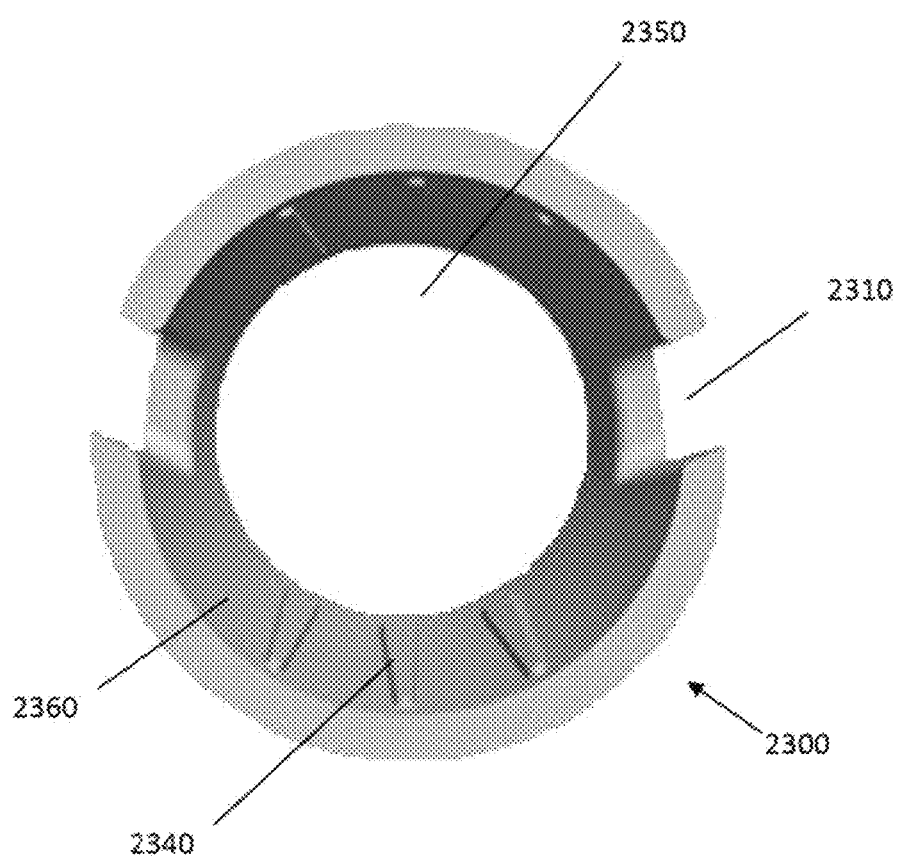
FIGS. 22A-B show a top and front view of a conical cone, respectively.
Figure 22B:
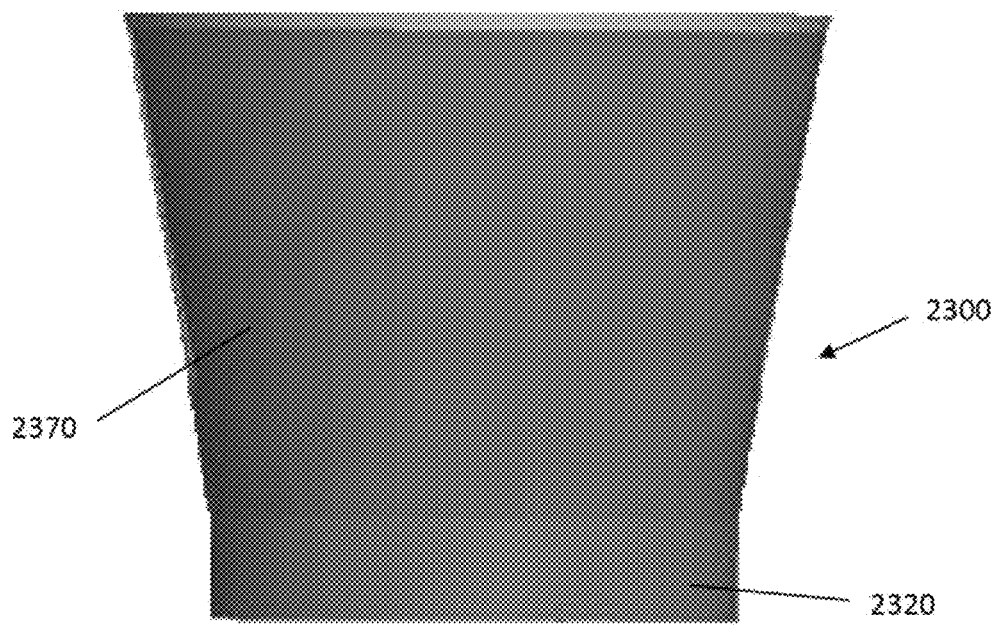

After the desired bone void has been created, the elongate IM reamer 1500 and reaming equipment is removed from the bone 1400. A desired cone is then selected for insertion into the corresponding bone void. FIGS. 22-23 illustrate two separate embodiments of the multitude of cones that may be selected. FIGS. 23A-F show a conical cone 2300 that is generally frustoconical in shape, but may include a conical cone neck 2320 extending from the distal end of the conical cone 2300 to improve stability. Referring to FIGS. 22A-B, the conical cone 2300 is shown in a top view and front view, respectively. The conical cone 2300 generally includes a central opening 2350 to accommodate a prosthesis stem 2520 and at least one clearance channel 2310 to accommodate a baseplate keel 2510. The interior space of the conical cone 2300 formed by the central opening 2350 may be packed with bone cement or other adhesive in order to enhance connection between the prosthesis and bone 1400. This enhanced connection is further improved by an adhesive anti-rotation feature 2340 located on the interior surface of the conical cone 2360. For example, the adhesive anti-rotation feature 2340 may be a series of protrusions extending from the interior surface of the conical cone 2360 to prohibit rotation of the adhesive with respect to the conical cone 2300. The conical cone 2300 may be constructed of any implant-grade material. For example, the interior surface of the conical cone 2360 may be constructed of solid titanium, and the exterior surface 2370 constructed of porous titanium to enhance binding bone growth. Another example would be where the conical cone 2300 varies in density such that the density decreases from a dense inner surface to a porous outer surface, which would allow for greater bone growth on the outer surface.

Figure 22C:
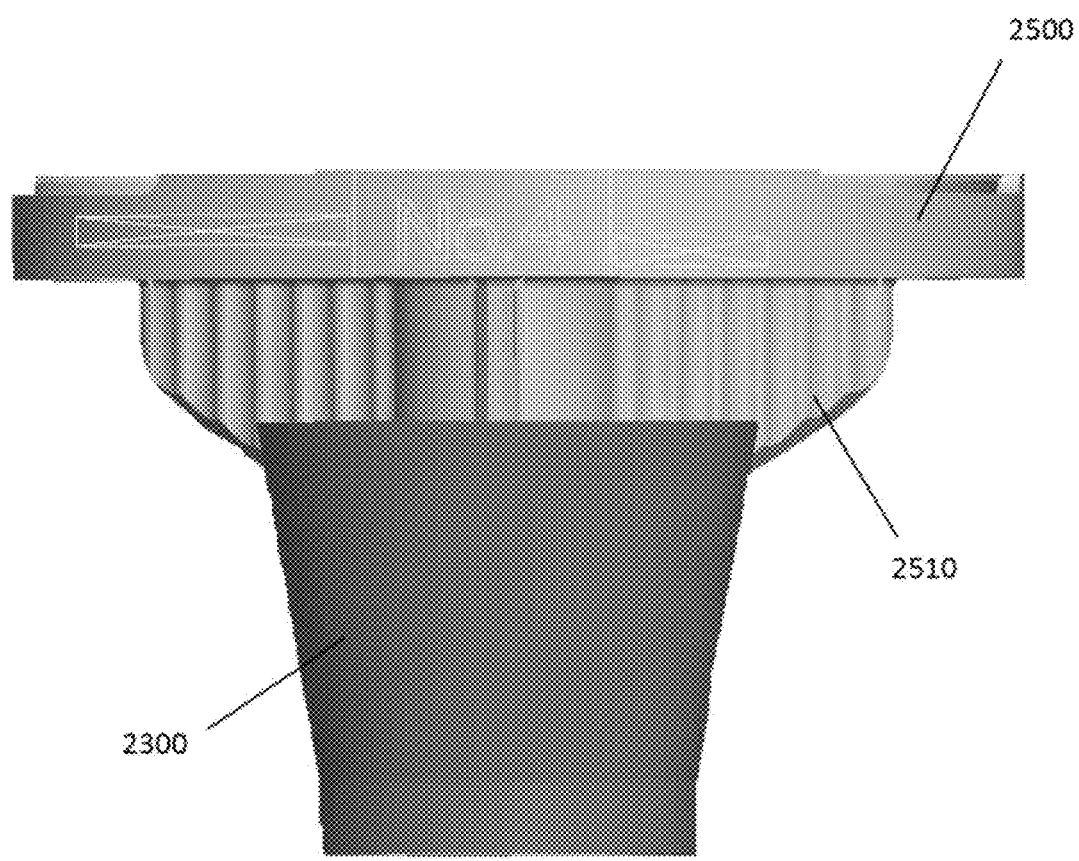
FIGS. 22C-D show a front and side view of an interrelation between the conical cone and a baseplate and baseplate keel.
Figure 22D:
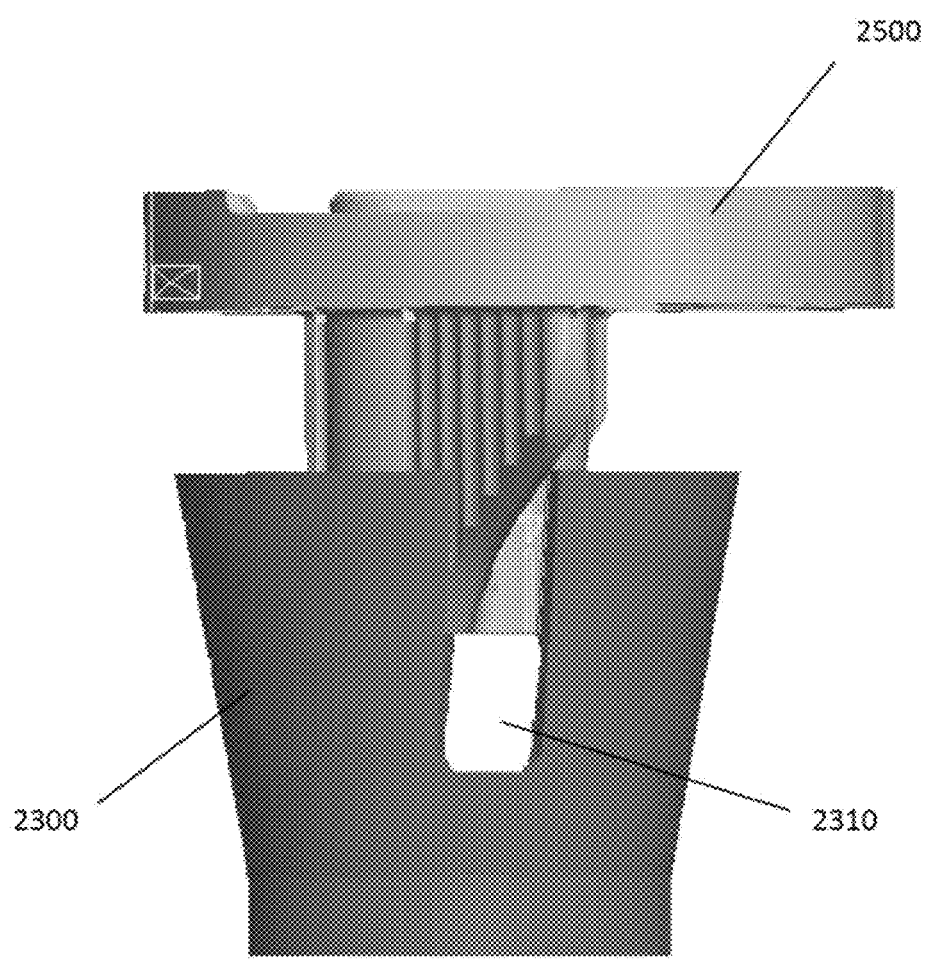

FIGS. 22C-D show a front and side view, respectively, demonstrating the interrelation of the conical cone clearance channel 2310 and baseplate keel 2510.

Figure 22E:
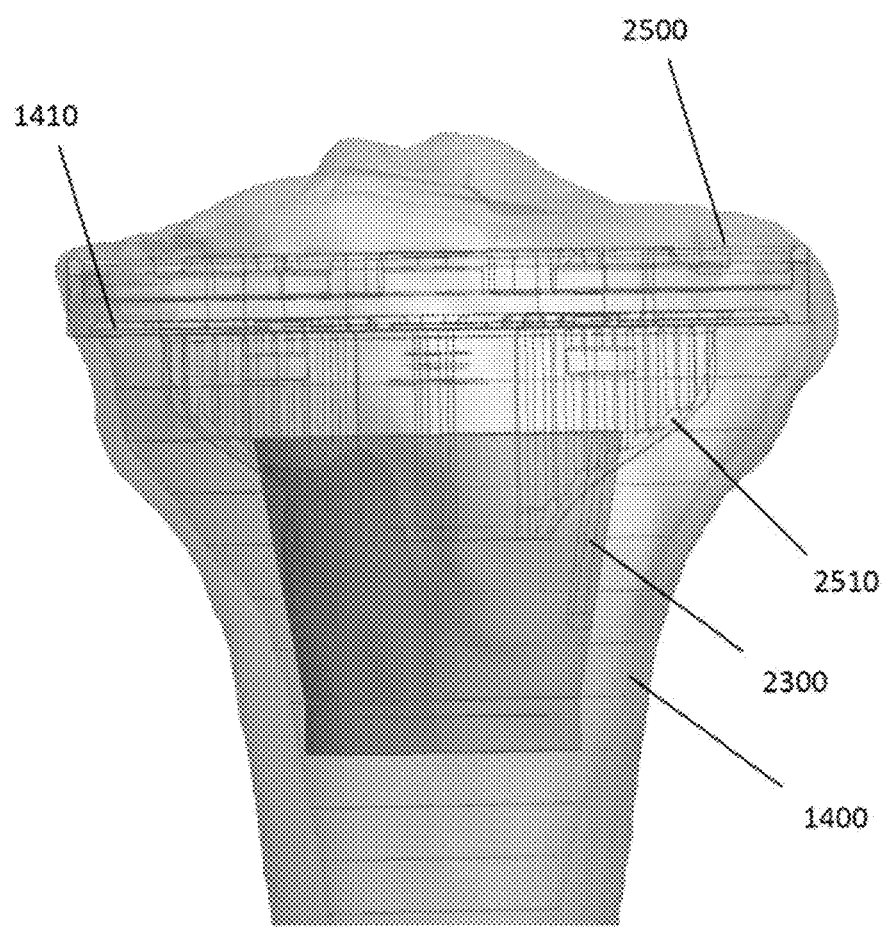
FIG. 22E shows a transparent view of an interrelation of the conical cone with the baseplate and baseplate keel when the conical cone is deep within bone.
Figure 22F:
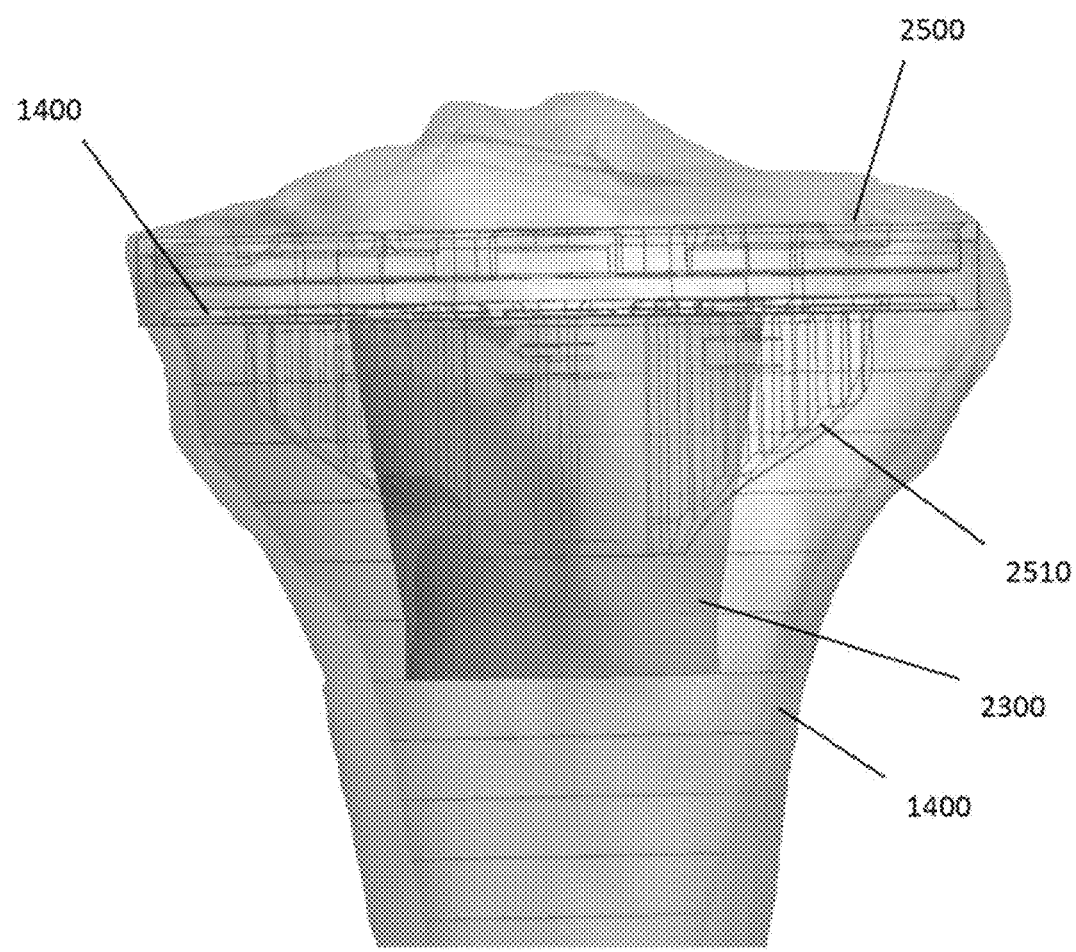
FIG. 22F shows a transparent view of an interrelation of the conical cone with the baseplate and baseplate keel when the conical cone is shallow within bone.

FIGS. 22E-F show transparent views of the interrelation between the conical cone 2300 and baseplate keel 2510 where the conical cone 2300 is implanted at differing bone depths. FIG. 22E illustrates the interrelation where the conical cone 2300 is deep within the bone 1400. This would typically occur where the surgeon utilizes augments to compensate for bone deformities.

FIG. 22F illustrates the interrelation where the conical cone 2300 is inserted into the central bone void such that the proximal surface of the conical cone 2300 is flush with the tibial platform 1410.

Figure 23A:
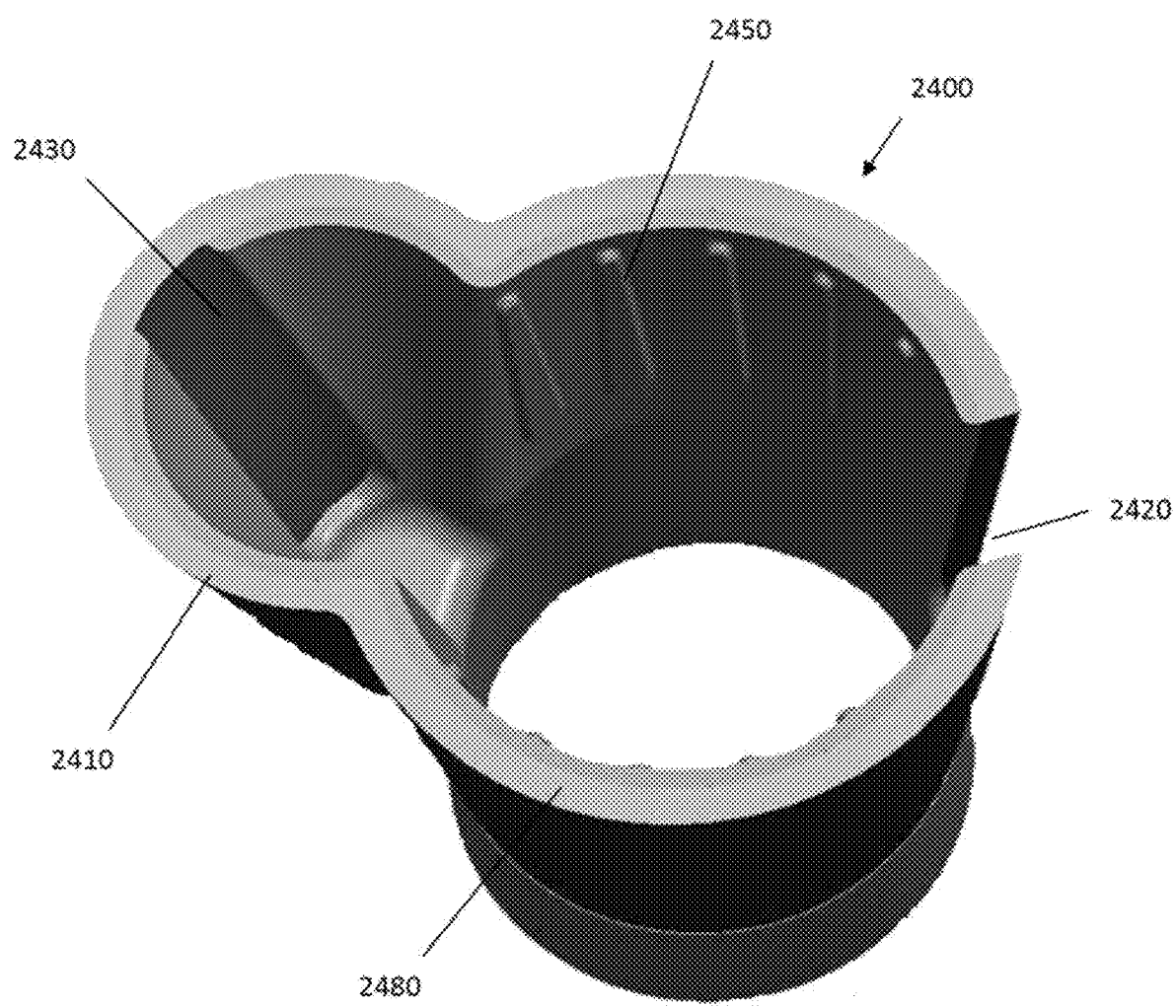
FIGS. 23A-C show a perspective, top, and front view of a lobed cone, respectively.
Figure 23B:
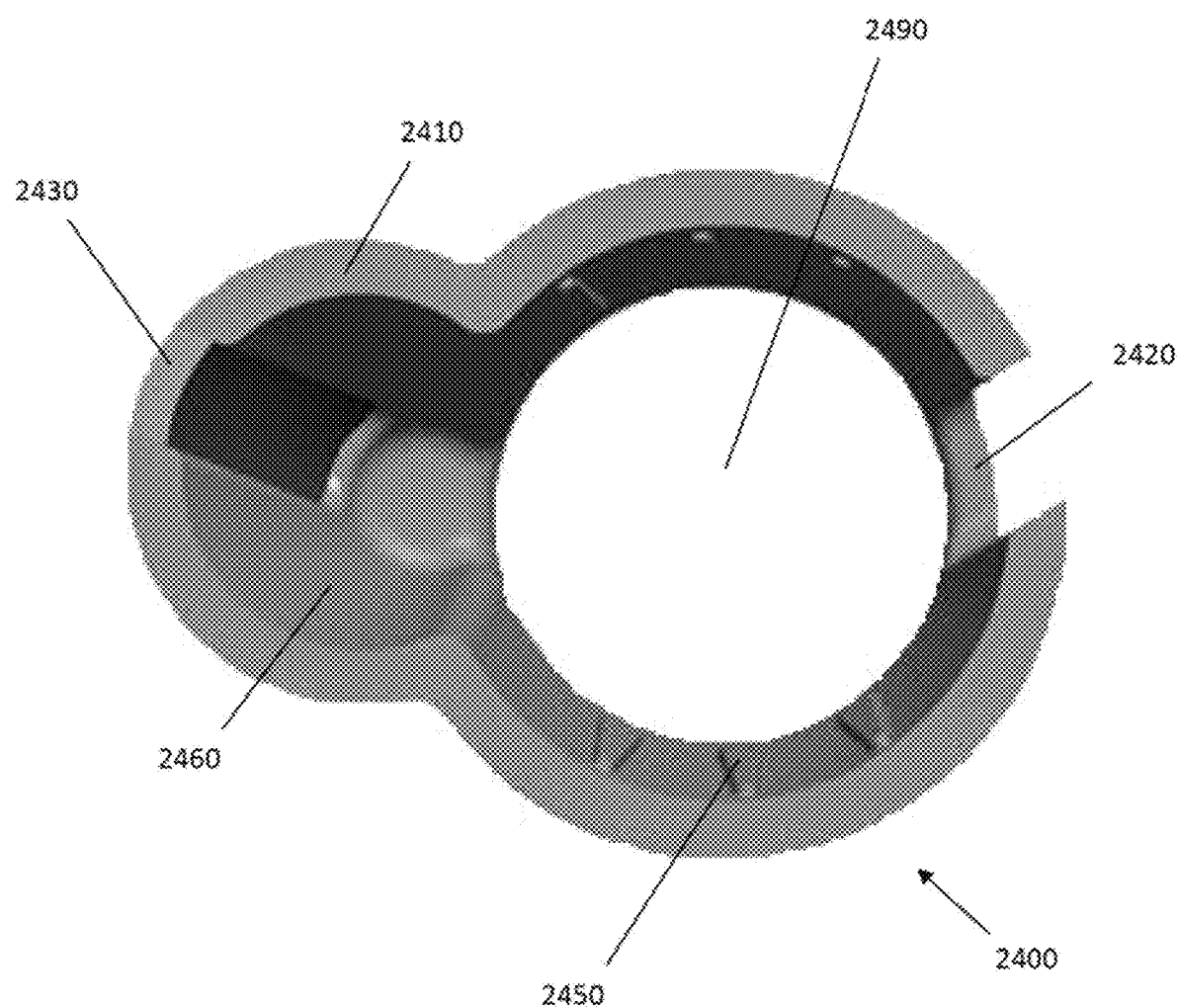
Figure 23C:
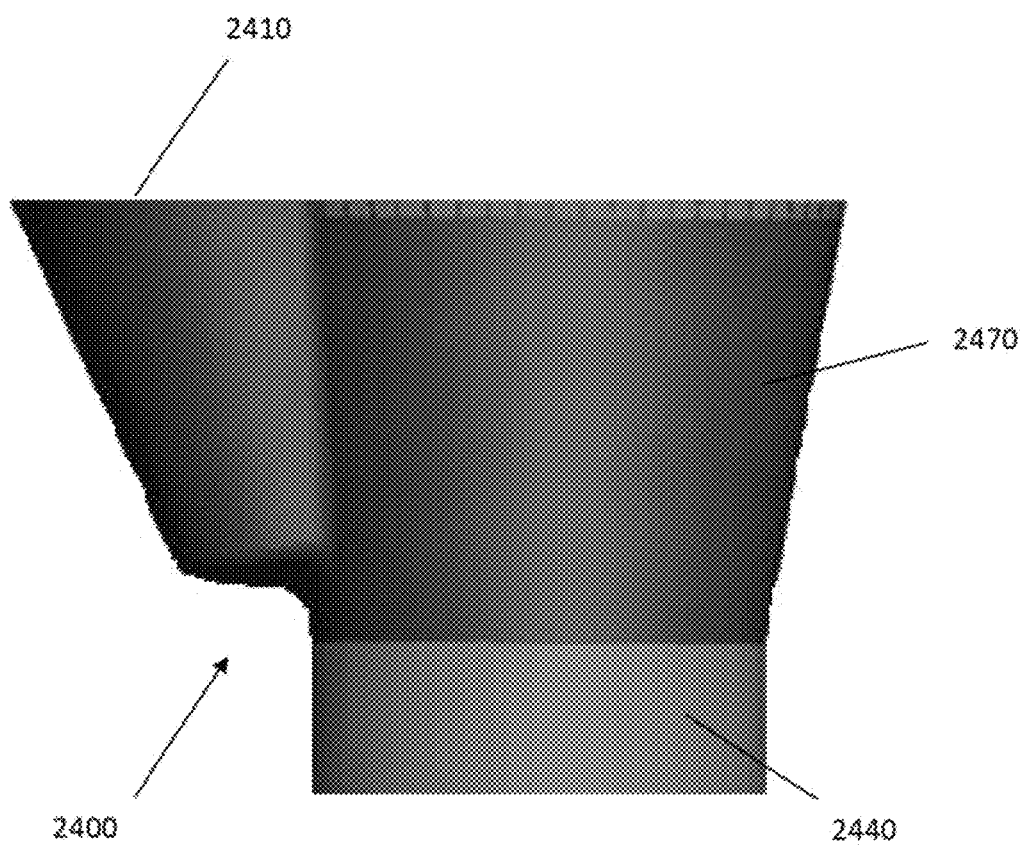

FIGS. 23A-G illustrate another cone embodiment. Referring now to FIGS. 23A-C, a perspective, top and front view, respectively, of a lobed cone 2400 is shown. The lobed cone 2400 generally includes a central opening 2450 to accommodate a prosthesis stem 2520, a clearance channel 2420 to accommodate a baseplate keel 2510, a conical body 2480, and a lobe 2410 integrated with the conical body 2480. The interior space of the lobed cone 2400 may be packed with bone cement or other adhesive in order to enhance connection between the prosthesis and bone 1400. This enhanced connection is further improved by an adhesive anti-rotation feature 2450 located on the interior surface of the lobed cone 2460. For example, the adhesive anti-rotation feature 2450 may include a series of protrusions extending from the interior surface of the lobed cone 2460 to prohibit rotation of the adhesive with respect to the lobed cone 2400. The lobed cone 2400 may be constructed of any implant-grade material. For example, the interior surface of the lobed cone 2460 may be constructed of solid titanium, and the exterior surface 2470 constructed of porous titanium to enhance binding bone growth. Another example would be where the lobed cone 2460 varies in density such that the density decreases from a dense inner surface to a porous outer surface, which would allow for greater bone growth on the outer surface.

Further, the lobe 2430 may include a window 2430. The window 2430 is essentially a clearance channel 2420 that has been covered by the porous titanium of the outer surface 2470. This provides the surgeon the flexibility to open the window 2430 by cutting out the porous titanium with standard surgical tools or a specialized tool, thereby creating an additional clearance window 2420 in the event clearance space is needed for a larger baseplate keel 2510. Where additional clearance space is not needed, the porous titanium remains to provide additional surface area for binding bone growth.

Figure 23D:
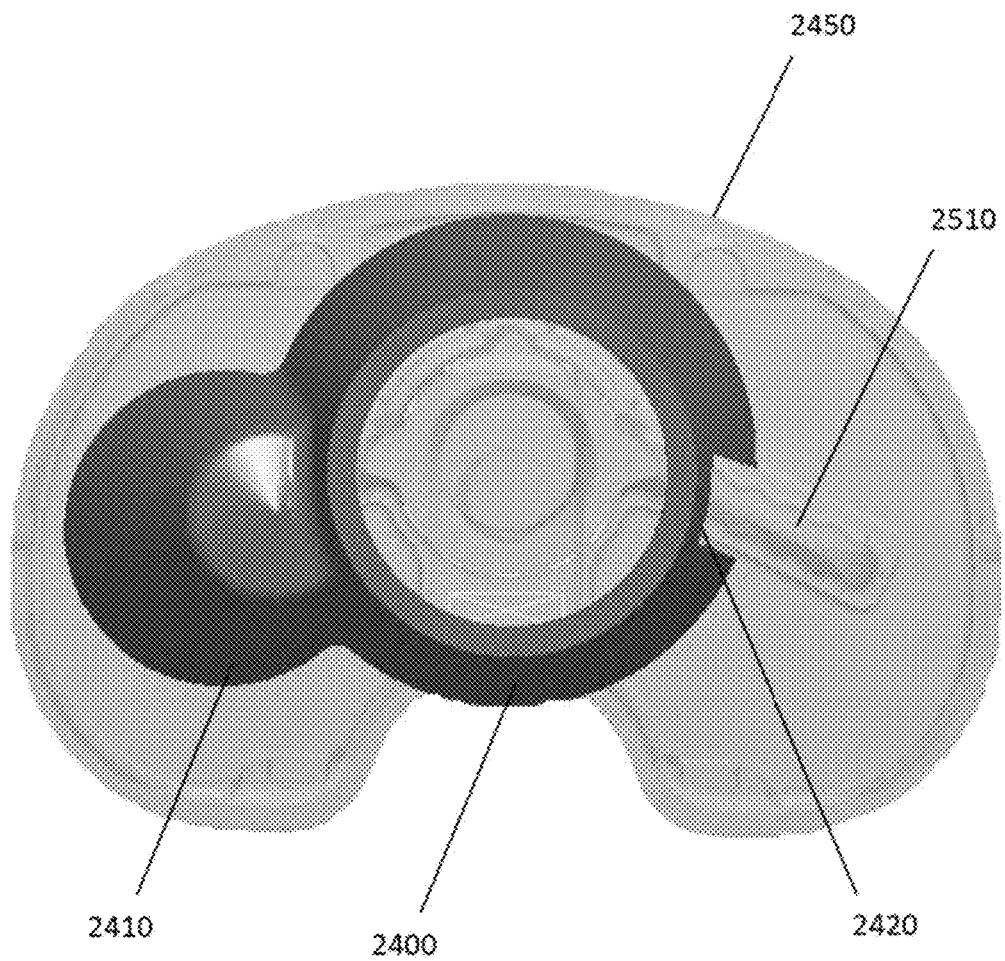
FIG. 23D shows a bottom view of an interrelation between a lobed cone and baseplate keel, particularly the relationship of the baseplate keel with regard to a lobe and clearance channel of the lobed cone.

FIG. 23D is a bottom view illustrating the interrelation of the lobed cone 2400 with the baseplate 2500 and baseplate keel 2510, and in particular the interrelation of the baseplate keel 2510 with the lobe 2410 and clearance channel 2420.

Figure 23E:
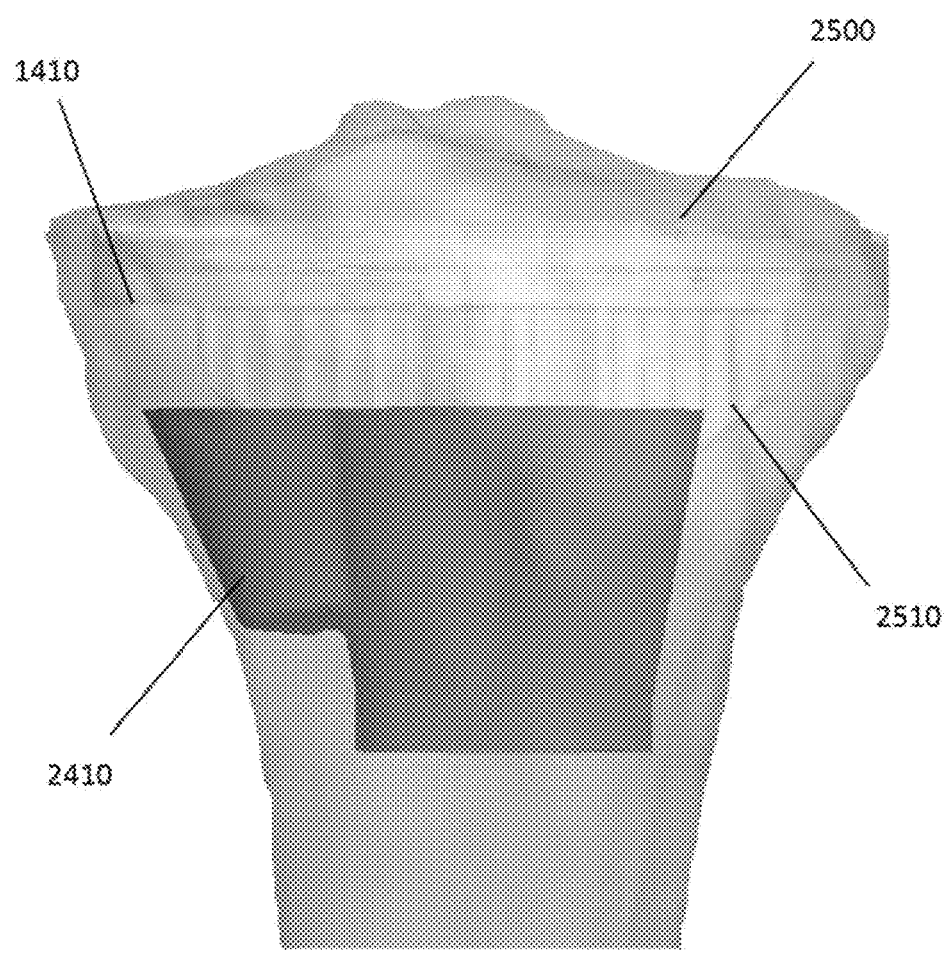
FIG. 23E shows a transparent view of an interrelation of the lobed cone with the baseplate and baseplate keel when the lobed cone is deep within bone.
Figure 23F:
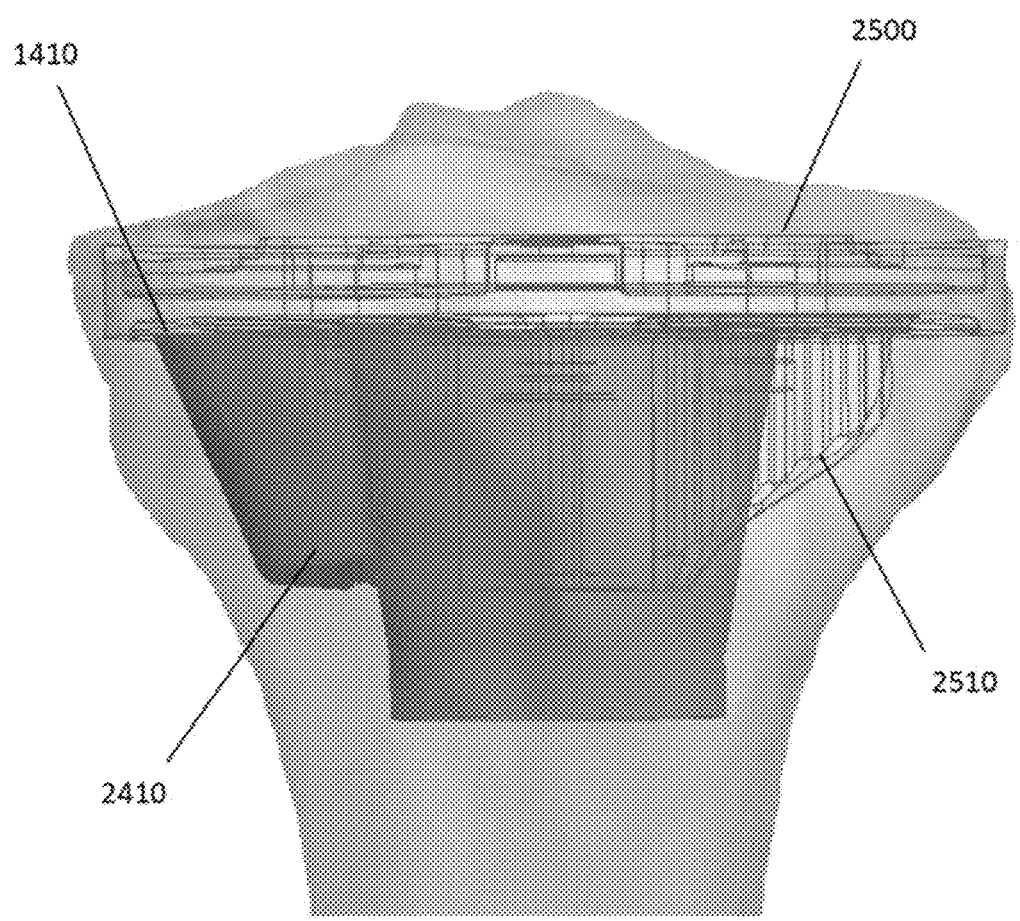
FIG. 23F shows a transparent view of an interrelation of the lobed cone with the baseplate and baseplate keel when the lobed cone is shallow within bone.

FIGS. 23E-F show transparent views of the interrelation between the lobed cone 2400 and baseplate keel 2510 depending on the depth of the lobed cone 2400 within the bone 1400. FIG. 22E illustrates this interrelation where the lobed cone 2400 is deep within the bone 1400. This would typically occur where the surgeon utilizes augments to compensate for bone deformities.

FIG. 23F illustrates the interrelation where the lobed cone 2400 is inserted into the central bone void and offset bone void such that the proximal surface of the lobed cone 2400 is flush with the tibial platform 1410.

Figure 23G:
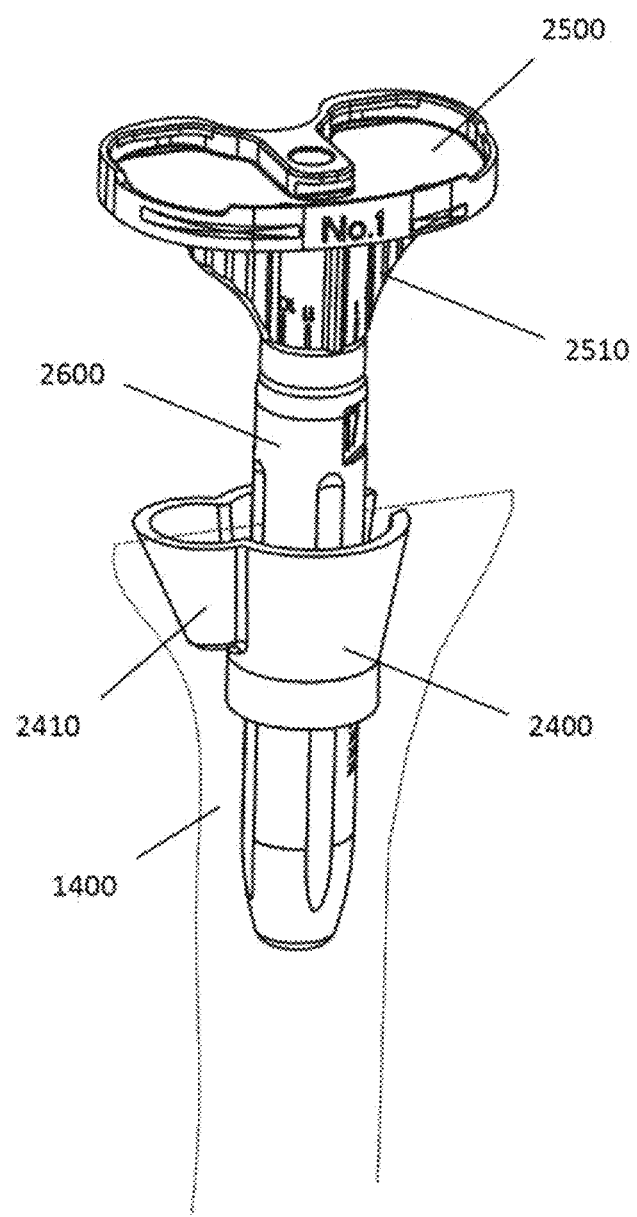
FIG. 23G shows an interrelation between the lobed cone and a stem of a prosthesis.

FIG. 23G shows the prosthesis being inserted into the lobed cone 2400 and bone for final implantation. The stem 2600 passes through the central opening 2450 and into the intramedullary canal. When fully inserted, the baseplate 2500 will rest proximally to the lobed coned 2400 with the baseplate keel 2510 residing partially within the lobed cone 2400. Generally, the lobed cone 2400 will be filled with adhesive to provide further support to the prosthesis.

There are many benefits of performing a revision procedure with the surgical reaming instruments of the present invention. For example, all bone removal steps may be fully guided without the need for any freehand bone removal. Additionally, the surgeon is left with the option to create an offset bone cavity by reaming the bone in three steps or broaching the bone in only two steps. Importantly, because of the precision of control allowed when using these instruments, the shape of the cavity can be precisely controlled which allows for stock MRDs/cones to accurately fit into the bone void without dependence on the technique of the particular surgeon performing the surgery. Related to this is that the symmetric, geometrically defined shape of an MRD/cone simplifies the setup and machining of void fillers. The MRDs/cones described herein can be made of any biocompatible material such as polymer, titanium, and stainless steel, for example.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims. For example, although embodiments of the invention have generally been described in reference to a femoral implant in a femur or with respect to a tibia, the principles described herein are equally applicable to bones of other joints.

The invention claimed is:

1. A broaching system comprising:
a shaft; and
a broach disposable over the shaft such that the shaft passes through a lumen of the broach, the broach having a head with a length extending from a trailing end to a leading end, a first outer surface that defines a conical shape that tapers from the trailing end toward the leading end, a second outer surface circumferentially separate from the first outer surface, the second outer surface including a first subpart and a second subpart separate from the first subpart, the first subpart having a first surface contour and the second subpart having a second surface contour different from the first surface contour.

2. The broaching system of claim 1, wherein the second subpart is shorter than the first subpart along a direction of the length.

3. The broaching system of claim 1, wherein the second subpart has a width dimension that changes along the direction of the length.

4. The broaching system of claim 1, wherein the conical shape of the first outer surface is different from the first surface contour.

5. The broaching system of claim 1, wherein the second subpart is non-conically shaped.

6. The broaching system of claim 5, wherein the second subpart has a non-tapered surface along a direction of the length.

7. The broaching system of claim 1, wherein the lumen of the broach has a first diameter at the leading end and a second diameter spaced apart from the leading end, the second diameter being less than the first diameter.

8. The broaching system of claim 1, wherein the broach includes a central longitudinal axis and the broach is asymmetric about at least one plane coincident with the central longitudinal axis.

9. The broaching system of claim 1, wherein the shaft includes an enlarged portion along its length, the enlarged portion configured to limit advancement of the broach relative to the shaft.

10. A broaching system comprising:
a shaft; and
a broach arranged such that the shaft passes into the broach, the broach comprising:
a cannulated head defined by an enclosed outer wall, the outer wall including a first outer wall portion and a second outer wall portion circumferentially separate from the first outer wall portion, the first outer wall portion having a first length along a length direction of the broach, the first outer wall portion being tapered from a first end of the first length to a second end of the first length, and the second outer wall portion having a second length along the length direction of the broach, the second outer wall portion being tapered from a first end of the second length to a second end of the second length, the second length being shorter than the first length,
wherein the enclosed outer wall includes a pair of wall portions separate from each other that are at different taper angles relative to a central longitudinal axis of the cannulated head.

11. The broaching system of claim 10, wherein each wall of the pair of wall portions are circumferentially separate from each other.

12. The broaching system of claim 10, wherein each wall of the pair of wall portions has a curved profile in a plane passing through the pair of wall portions where the plane is orthogonal to the central longitudinal axis.

13. The broaching system of claim 12, wherein the walls of the pair of wall portions have different curved profiles in the plane.

14. The broaching system of claim 10, wherein one end of the first outer wall portion and one end of the second outer wall portion are aligned with a single longitudinal location along the central longitudinal axis.

15. The broaching system of claim 10, wherein the first outer wall portion is conically shaped.

16. The broaching system of claim 10, wherein a cannulation of the cannulated head flares outward from an interior location of the cannulation to the second end of the cannulated head.

17. The broaching system of claim 10, wherein an end surface of the cannulated head at the second end of the cannulated head is circular.

* * * * *